United States Patent
Ito et al.

(10) Patent No.: US 9,273,002 B2
(45) Date of Patent: Mar. 1, 2016

(54) BENZO[K]FLUORANTHENE DERIVATIVE AND ORGANIC ELECTROLUMINESCENCE DEVICE CONTAINING THE SAME

(75) Inventors: Hirokatsu Ito, Sodegaura (JP);
Masahiro Kawamura, Sodegaura (JP);
Yuichiro Kawamura, Sodegaura (JP);
Yumiko Mizuki, Sodegaura (JP);
Hiroyuki Saito, Sodegaura (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 671 days.

(21) Appl. No.: 13/504,575

(22) PCT Filed: Oct. 7, 2011

(86) PCT No.: PCT/JP2011/073202
§ 371 (c)(1),
(2), (4) Date: Apr. 27, 2012

(87) PCT Pub. No.: WO2012/046839
PCT Pub. Date: Apr. 12, 2012

(65) Prior Publication Data
US 2012/0211743 A1 Aug. 23, 2012

(30) Foreign Application Priority Data
Oct. 8, 2010 (JP) .................................. 2010-229070

(51) Int. Cl.
*H01L 51/54* (2006.01)
*C07D 471/04* (2006.01)
(Continued)

(52) U.S. Cl.
CPC ............ *C07D 213/22* (2013.01); *C07D 401/04* (2013.01); *C07D 471/04* (2013.01);
(Continued)

(58) Field of Classification Search
CPC .. C07D 213/22; C07D 401/04; C07D 471/04; H05B 33/20; H01L 51/0067; H01L 51/0072; H01L 51/0055; H01L 51/5048
See application file for complete search history.

(56) References Cited

U.S. PATENT DOCUMENTS

2004/0076853 A1* 4/2004 Jarikov .......................... 428/690
2006/0214553 A1* 9/2006 Nagara et al. .................. 313/483
(Continued)

FOREIGN PATENT DOCUMENTS

EP    1990843 A1 * 11/2008
JP    10 189247      7/1998
(Continued)

OTHER PUBLICATIONS

Translation for JP 2005-108552 A (publication date: Apr. 2005).*
(Continued)

*Primary Examiner* — Dawn L. Garrett
(74) *Attorney, Agent, or Firm* — Oblon, McClelland, Maier & Neustadt, L.L.P.

(57) ABSTRACT

A benzo[k]fluoranthene derivative represented by the following formula (1):

(1)

wherein $R_1$ to $R_{12}$ are as defined in the specification. The benzo[k]fluoranthene derivative represented by the formula (1) reduces a driving voltage of an organic electroluminescence device and makes it possible to realize light emission with high efficiency and long lifetime.

19 Claims, 2 Drawing Sheets

| Cathode | 40 |
| Electron Transporting Zone | 30 |
| Light Emitting Layer | 20 |
| Hole Transporting Zone | 50 |
| Anode | 10 |

(51) Int. Cl.
- *C07D 401/04* (2006.01)
- *C07D 213/22* (2006.01)
- *C09K 11/06* (2006.01)
- *H01L 51/00* (2006.01)
- *H05B 33/20* (2006.01)
- *H01L 51/50* (2006.01)

(52) U.S. Cl.
CPC ........... *C09K 11/06* (2013.01); *H01L 51/0055* (2013.01); *H01L 51/0067* (2013.01); *H01L 51/0072* (2013.01); *H05B 33/20* (2013.01); *H01L 51/5048* (2013.01)

(56) References Cited

U.S. PATENT DOCUMENTS

| | | | |
|---|---|---|---|
| 2007/0063189 A1* | 3/2007 | Schwalm et al. | 257/40 |
| 2007/0104977 A1* | 5/2007 | Arakane et al. | 428/690 |
| 2008/0007160 A1* | 1/2008 | Sado et al. | 313/504 |
| 2008/0032123 A1* | 2/2008 | Spindler et al. | 428/336 |
| 2008/0161574 A1* | 7/2008 | Ohrui et al. | 546/85 |
| 2009/0015144 A1 | 1/2009 | Takashima et al. | |
| 2009/0278118 A1* | 11/2009 | Ohrui et al. | 257/40 |
| 2009/0278447 A1* | 11/2009 | Saitoh et al. | 313/504 |
| 2010/0117519 A1* | 5/2010 | Begley et al. | 313/504 |
| 2010/0117520 A1* | 5/2010 | Begley et al. | 313/504 |

FOREIGN PATENT DOCUMENTS

| | | |
|---|---|---|
| JP | 2003 123983 | 4/2003 |
| JP | 2005 068087 | 3/2005 |
| JP | 2005 108552 | 4/2005 |
| JP | 2005-108552 A * | 4/2005 |
| JP | 2005 108556 | 4/2005 |
| JP | 2008 156315 | 7/2008 |
| JP | 2008-222624 A | 9/2008 |
| WO | 2008 059713 | 5/2008 |

OTHER PUBLICATIONS

Derwent abstract for WO 2007/099983 A1 (Sep. 7, 2007) and patent family equivalent document EP 1990843 A1 (Nov. 12, 2008).*
International Search Report Issued Dec. 20, 2011 in PCT/JP11/73202 Filed Oct. 7, 2011.
Japanese Office Action issued on Jun. 23, 2015 in corresponding Japanese Patent Application No. 2012-516424. 3 pp.

* cited by examiner

BENZO[K]FLUORANTHENE DERIVATIVE AND ORGANIC ELECTROLUMINESCENCE DEVICE CONTAINING THE SAME

This application is a 371 of PCT/JP2011/073202, filed Oct. 7, 2011. Priority to Japanese patent application 2010-229070, filed Oct. 8, 2010, is claimed.

TECHNICAL FIELD

The present invention relates to a benzo[k]fluoranthene derivative and an organic electroluminescence device (organic EL device) containing the benzo[k]fluoranthene derivative.

BACKGROUND ART

In order to realize an organic EL device with excellent luminous efficiency, driving voltage and luminous lifetime, there have hitherto been developed a variety of compounds. For the purpose of enhancing electron injection properties from a cathode, there are proposed compounds containing a heterocyclic structure of every sort as an electron transporting material.

Patent Document 1 discloses compounds having a 1,10-phenanthroline structure or a bipyridine structure. However, luminance, half-lifetime and luminous efficiency of organic EL devices containing these compounds described in the working examples are merely relative values on the basis of organic EL devices using comparative compounds. Actual measured values which enable one to decide whether or not these compounds realize a practically effective EL device performance are not shown.

Patent Documents 2 and 3 disclose anthracene compounds having two 2,2'-bipyridin-5-yl groups. Though the compounds disclosed in Patent Document 3 improve the lifetime, a driving voltage thereof tends to become high.

Though Patent Document 4 discloses anthracene compounds having a 1,10-phenanthrolinyl group, a more improvement in the lifetime is desired.

Patent Documents 5 and 6 describe that benzo[k]fluoranthene compounds having a benzoimidazolyl group or a substituent analogous thereto are used as an electron transporting material.

[Patent Document 1] JP-A-2003-123983
[Patent Document 2] WO2007/086552
[Patent Document 3] JP-A-2009-275013
[Patent Document 4] WO2007/018004
[Patent Document 5] WO2009/148269
[Patent Document 6] KR-A-2009-0059849

DISCLOSURE OF THE INVENTION

An object of the present invention is to solve the problems of the compounds as described above and to provide a novel compound which reduces a driving voltage of an organic EL device and which makes it possible to realize light emission with high efficiency and long lifetime.

The present inventors made extensive and intensive investigations. As a result, it has been found that a benzo[k]fluoranthene derivative as described below achieves the foregoing object, leading to accomplishment of the present invention. That is, the present invention relates to a benzo[k]fluoranthene derivative, a device for organic electroluminescence device, and an organic EL device containing the subject derivative as described below.

1. A benzo[k]fluoranthene derivative represented by the following formula (1).

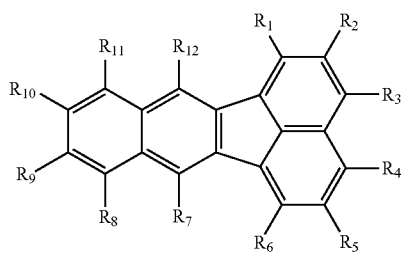

In the formula, each of $R_1$ to $R_{12}$ independently represents a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms, or a substituted or unsubstituted heterocyclic group having 5 to 30 ring atoms, provided that at least one of $R_1$ to $R_{12}$ is a group represented by the following formula (1a).

In the formula, L represents a single bond, a divalent to tetravalent residue of a substituted or unsubstituted aromatic hydrocarbon ring having 6 to 30 ring carbon atoms, a divalent to tetravalent residue of a substituted or unsubstituted heterocyclic ring having 5 to 30 ring atoms, or a divalent to tetravalent residue of a ring formed through bonding of from 2 to 3 rings selected from the foregoing aromatic hydrocarbon ring and heterocyclic ring via a single bond; n represents an integer of from 1 to 3; and HAr represents a group represented by the following formula (2).

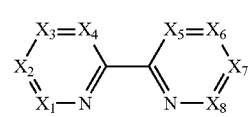

In the formula, each of $X_1$ to $X_8$ independently represents a nitrogen atom or $CR_{13}$, and at least one of $X_1$ to $X_8$ is $CR_{13}$; and each of $R_{13}$s independently represents a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted mono- or dialkylamino group having 1 to 20 carbon atoms, a substituted or unsubstituted aryl group having 6 to 30 ring carbon atoms, a substituted or unsubstituted heterocyclic group having 5 to 30 ring atoms, a substituted or unsubstituted arylthio group having 6 to 20 ring carbon atoms, or a substituted or unsubstituted mono- or diarylamino group having 6 to 40 ring carbon atoms, provided that one of $R_{13}$s is a single bond and is bonded to L; two or more of $R_{13}$s may be bonded to each other to form a substituted or unsubstituted, saturated or unsaturated group; and the case where each of $X_4$ and $X_5$ is $C_{13}$, and the $R_{13}$s are bonded to each other to form a substituted or unsubstituted methylene group is excluded.

2. The benzo[k]fluoranthene derivative as set forth in Item 1, wherein HAr is one of nitrogen-containing heterocyclic rings represented by the following formulae (3) to (7).

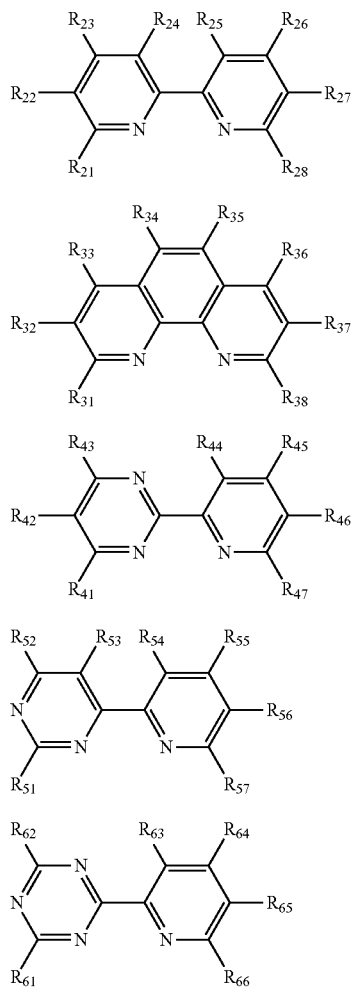

In the formulae, each of $R_{21}$ to $R_{66}$ independently represents a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, substituted or unsubstituted mono- or dialkylamino group having 1 to 20 carbon atoms, a substituted or unsubstituted aryl group having 6 to 30 ring carbon atoms, a substituted or unsubstituted heterocyclic group having 5 to 30 ring atoms, a substituted or unsubstituted arylthio group having 6 to 20 ring carbon atoms, or a substituted or unsubstituted mono- or diarylamino group having 6 to 40 ring carbon atoms;

in the formula (3), two or more of $R_{21}$ to $R_{28}$ may be bonded to each other to form a ring-forming substituted or unsubstituted, saturated or unsaturated group, provided that any one of $R_{21}$ to $R_{28}$ is a single bond and is bonded to L, and the case where $R_{24}$ and $R_{25}$ are bonded to each other to form a substituted or unsubstituted methylene group is excluded;

in the formula (4), two or more of $R_{31}$ to $R_{38}$ may be bonded to each other to form a ring-forming substituted or unsubstituted, saturated or unsaturated group, provided that any one of $R_{31}$ to $R_{38}$ is a single bond and is bonded to L;

in the formula (5), two or more of $R_{41}$ to $R_{47}$ may be bonded to each other to form a ring-forming substituted or unsubstituted, saturated or unsaturated group, provided that any one of $R_{41}$ to $R_{47}$ is a single bond and is bonded to L;

in the formula (6), two or more of $R_{51}$ to $R_{57}$ may be bonded to each other to form a ring-forming substituted or unsubstituted, saturated or unsaturated group, provided that any one of $R_{51}$ to $R_{57}$ is a single bond and is bonded to L, and the case where $R_{53}$ and $R_{54}$ are bonded to each other to form a substituted or unsubstituted methylene group is excluded; and in the formula (7), two or more of $R_{61}$ to $R_{66}$ may be bonded to each other to form a ring-forming substituted or unsubstituted, saturated or unsaturated group, provided that any one of $R_{61}$ to $R_{66}$ is a single bond and is bonded to L.

3. The benzo[k]fluoranthene derivative as set forth in Item 1 or 2, which is represented by the following formula (8).

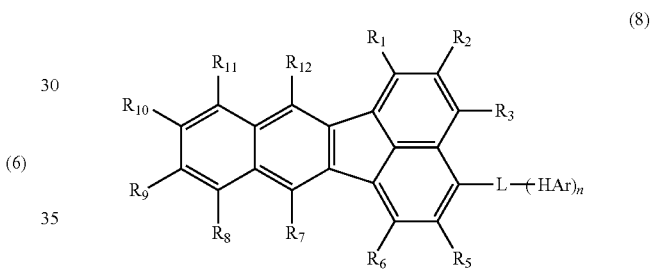

In the formula, $R_1$ to $R_3$, $R_5$ to $R_{12}$, HAr, L, and n are the same as defined above.

4. The benzo[k]fluoranthene derivative as set forth in any of Items 1 to 3, wherein n is 1.

5. A material for organic electroluminescence device containing the benzo[k]fluoranthene derivative as set forth in any of Items 1 to 4.

6. The material for organic electroluminescence device as set forth in Item 5, wherein the material for organic electroluminescence device is an electron injecting material or an electron transporting material.

7. An organic electroluminescence device comprising one or more organic thin film layers which comprise a light emitting layer and are interposed between a cathode and an anode, wherein at least one layer of the organic thin film layers comprises one or more kinds of the benzo[k]fluoranthene derivative as set forth in any of Items 1 to 4.

8. The organic electroluminescence device as set forth in Item 7, wherein the organic thin film layers comprises an electron injecting layer or an electron transporting layer, and the electron injecting layer or electron transporting layer comprises one or more kinds of the benzo[k]fluoranthene derivative.

9. The organic electroluminescence device as set forth in Item 8, wherein the electron injecting layer or electron transporting layer containing the benzo[k]fluoranthene derivative further comprises a reducing dopant.

10. The organic electroluminescence device as set forth in Item 9, wherein the reducing dopant is one or more kinds selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex of an alkali metal, an organic complex of an alkaline earth metal, and an organic complex of a rare earth metal.

The organic EL device containing the benzo[k]fluoranthene derivative of the present invention is low in a driving voltage and exhibits light emission with high efficiency and long lifetime.

BEST MODES FOR CARRYING OUT THE INVENTION

Figure 1:
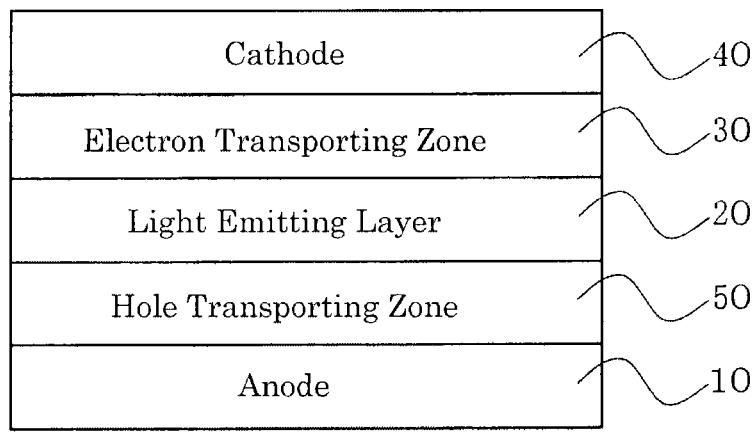
FIG. 1 is a view showing an example of embodiments of the present invention.

The benzo[k]fluoranthene derivative of the present invention is represented by the following formula (1).

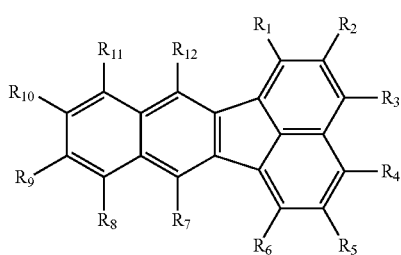

In the formula, each of $R_1$ to $R_{12}$ independently represents a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms, or a substituted or unsubstituted heterocyclic group having 5 to 30 ring atoms. However, at least one of $R_1$ to $R_{12}$ is a group represented by the following formula (1a).

In the formula (1), $R_1$ to $R_{12}$ may be the same as or different from each other, and the respective groups represented by each of them are as follows.

The halogen atom is selected from a fluorine atom, a chlorine atom, a bromine atom, and an iodine atom, with a fluorine atom being preferable.

As the alkyl group having 1 to 10 (preferably 1 to 6, and more preferably 1 to 4) carbon atoms, an ethyl group, a methyl group, an isopropyl group, an n-propyl group, an n-butyl group, an s-butyl group, a t-butyl group, an isobutyl group, a pentyl group (inclusive of structural isomerism), a hexyl group (inclusive of structural isomerism), and the like are preferable. Examples of the substituted alkyl group include alkyl groups having a substituent as described later.

As the cycloalkyl group having 3 to 8 (preferably 3 to 6) ring carbon atoms, a cyclopropyl group, a cyclobutyl group, a cyclopentyl group, and a cyclohexyl group are preferable. Examples of the substituted cycloalkyl group include cycloalkyl groups having a substituent as described later.

The substituted silyl group having 3 to 30 carbon atoms includes an alkylsilyl group having 3 to 30 carbon atoms (inclusive of mono-, di- and trialkylsilyl groups) and an arylsilyl group having 8 to 30 carbon atoms (inclusive of an aryldialkylsilyl group, a diarylalkylsilyl group, and a triarylsilyl group). Examples of the alkylsilyl group having 3 to 30 (preferably 3 to 20, and more preferably 3 to 10) carbon atoms include a trimethylsilyl group, a triethylsilyl group, a t-butyldimethylsilyl group, a vinyldimethylsilyl group, a propyldimethylsilyl group, and so on. Examples of the arylsilyl group having 8 to 30 carbon atoms include a triphenylsilyl group, a phenyldimethylsilyl group, a t-butyldiphenylsilyl group, a tritolylsilyl group, a trixylylsilyl group, a trinaphthylsilyl group, and so on.

The alkoxy group having 1 to 20 (preferably 1 to 10, and more preferably 1 to 6) carbon atoms is a group represented by —OY, and specific examples, preferred examples, and more preferred examples of Y are selected from the groups described above regarding the alkyl group. Examples of the substituted alkoxy include alkoxy groups having a substituent as described later.

Examples of the aryl group having 6 to 30 (preferably 6 to 20, and more preferably 6 to 12) ring carbon atoms include a phenyl group, a naphthyl group, a phenanthryl group, a biphenyl group, a terphenyl group, an anthryl group, a pyrenyl group, a chrysenyl group, a benzophenanthryl group, a benzanthryl group, a benzochrysenyl group, a fluorenyl group, a fluoranthenyl group, a naphthacenyl group, and so on. A phenyl group, a 1-naphthyl group, a 2-naphthyl group, a 2-biphenyl group, a 3-biphenyl group, a 4-biphenyl group, a 9-phenanthryl group, and a 1-pyrenyl group are more preferable, with a phenyl group being especially preferable. Examples of the substituted aryl group include aryl groups having a substituent as described later. A 4-tolyl group, a 4-fluorophenyl group, a 4-trifluoromethylphenyl group, a 4-t-butylphenyl group, a 4-trimethylsilylphenyl group, a 4-methoxyphenyl group, a 4-cyanophenyl group, a 3-tolyl group, a 3-fluorophenyl group, a 3-trifluoromethylphenyl group, a 3-t-butylphenyl group, a 3-trimethylsilylphenyl group, a 3-methoxyphenyl group, a 3-cyanophenyl group, a 2-tolyl group, a 2-fluorophenyl group, a 2-trifluoromethylphenyl group, a 2-t-butylphenyl group, a 2-trimethylsilylphenyl group, a 2-methoxyphenyl group, a 2-cyanophenyl group, and the like are preferable. The substituted or unsubstituted aryl group is especially preferably a phenyl group.

The aryloxy group having 6 to 20 (preferably 6 to 10) ring carbon atoms is a group represented by —OAr, and Ar is selected from the groups and preferred groups described above regarding the aryl group. Examples of the substituted aryloxy group include aryloxy groups having a substituent as described later.

Examples of the heterocyclic group having 5 to 30 (preferably 5 to 20, and more preferably 5 to 12) ring atoms include a pyridyl group, a pyrazinyl group, a pyrimidinyl group, a pyridazinyl group, a triazinyl group, an indolyl group, a quinolinyl group, an isoquinolinyl group, a quinoxalinyl group, an acridinyl group, a pyrrolidinyl group, a dioxanyl group, a piperidinyl group, a morpholyl group, a piperazinyl group, a carbazolyl group, a furanyl group, a thiophenyl group, an oxazolyl group, an isoxazolyl group, an oxadiazolyl group, a furazanyl group, a benzoxazolyl group, a thiazolyl group, an isothiazolyl group, a thiadiazolyl group, a benzothiophenyl group, a benzothiazolyl group, a triazolyl group, an imidazolyl group, a benzoimidazolyl group, a benzofuranyl group, a dibenzofuranyl group, a dibenzothiophenyl group, a pyrazolyl group, an indazolyl group, an imidazopyridyl group, a tetrazolyl group, and so on, with a pyridyl group, a pyrazinyl group, a pyrimidinyl group, a triazinyl group, a quinolinyl group, and an isoquinolinyl group being preferable. Examples of the substituted heterocyclic group include heterocyclic groups having a substituent as described later.

As $R_1$ to $R_{12}$ in the formula (1), a hydrogen atom, a halogen atom, a substituted or unsubstituted alkyl having 1 to 10 carbon atoms, a substituted or unsubstituted cycloalkyl group having 3 to 8 ring carbon atoms, and a substituted or unsubstituted aryl group having 6 to 30 ring carbon atoms are preferable.

In the derivative of the formula (1), it is preferable that both of $R_7$ and $R_{12}$ are a hydrogen atom or the substituent described above. The substituent is preferably a group selected from a phenyl group, a 1-naphthyl group, a 2-naphthyl group, a 2-biphenyl group, a 3-biphenyl group, a 4-biphenyl group, a 9-phenanthryl group, a 1-pyrenyl group, a 4-tolyl group, a 4-fluorophenyl group, a 4-trifluoromethylphenyl group, a 4-t-butylphenyl group, a 4-trimethylsilylphenyl group, a 4-methoxyphenyl group, a 4-cyanophenyl group, a 3-tolyl group, a 3-fluorophenyl group, a 3-trifluoromethylphenyl group, a 3-t-butylphenyl group, a 3-trimethylsilylphenyl group, a 3-methoxyphenyl group, a 3-cyanophenyl group, a 2-tolyl group, a 2-fluorophenyl group, a 2-trifluoromethylphenyl group, a 2-t-butylphenyl group, a 2-trimethylsilylphenyl group, a 2-methoxyphenyl group, a 2-cyanophenyl group, and so on. It is especially preferable that both of $R_7$ and $R_{12}$ are a hydrogen atom or a phenyl group.

In the formula (1), the respective groups of the formula (1a) are as follows.

-L-(-HAr)$_n$     (1a)

In the formula (1a), L represents a single bond, a divalent to tetravalent residue of a substituted or unsubstituted aromatic hydrocarbon ring having 6 to 30 ring carbon atoms, a divalent to tetravalent residue of a substituted or unsubstituted heterocyclic ring having 5 to 30 ring atoms, or a divalent to tetravalent residue of a ring formed through bonding of 2 to 3 rings selected from the foregoing aromatic hydrocarbon ring and heterocyclic ring via a single bond.

The divalent to tetravalent (preferably divalent or trivalent, and more preferably divalent) residue of an aromatic hydrocarbon ring having 6 to 30 (preferably 6 to 20, and more preferably 6 to 12) ring carbon atoms is a divalent to tetravalent group obtained by eliminating 1 to 3 hydrogen atoms from the aryl group having 6 to 30 ring carbon atoms as described regarding $R_1$ to $R_{12}$. A divalent to tetravalent residue of a ring selected from benzene, naphthalene, biphenyl, pyrene, phenanthrene, fluoranthene, chrysene, p-terphenyl, m-terphenyl, and 9,9-dimethylfluorene is preferable; a phenylene group, a benzenetriyl group, a naphthalenediyl group, a biphenyldiyl group, a pyrenediyl group, a phenanthrenediyl group, a fluoranthenediyl group, a chrysenediyl group, p-terphenyldiyl group, an m-terphenyldiyl group, an m-terphenyltriyl group, and a 9,9-dimethylfluorenediyl group are more preferable; a 1,2-phenylene group, a 1,3-phenylene group, a 1,4-phenylene group, a 2,6-naphthalenediyl group, a 1,4-naphthalenediyl group, a biphenyl-4,4'-diyl group, a biphenyl-3,3'-diyl group, a biphenyl-4,3'-diyl group, a biphenyl-3,4'-diyl group, a biphenyl-3,5-diyl group, a pyrene-1,6-diyl group, a phenanthrene-3,9-diyl group, a fluoranthene-3,8-diyl group, a chrysene-6,12-diyl group, a p-terphenyl-4,4"-diyl group, a p-terphenyl-3,5-diyl group, an m-terphenyl-3,5'-diyl group, an m-terphenyl-4,5'-diyl group, an m-terphenyl-4,4"-diyl group, an m-terphenyl-3,4"-diyl group, an m-terphenyl-4,3"-diyl group, a 9,9-dimethylfluorene-2,7-diyl group, a benzene-1,3,5-triyl group, and an m-terphenyl-4,5',4"-triyl group are still more preferable; and a 1,2-phenylene group, a 1,3-phenylene group, a 1,4-phenylene group, a 2,6-naphthalenediyl group, a biphenyl-4,4'-diyl group, a biphenyl-3,3'-diyl group, a biphenyl-4,3'-diyl group, a biphenyl-3,4'-diyl group, and a biphenyl-3,5-diyl group are especially preferable.

The divalent to tetravalent (preferably divalent or trivalent, and more preferably divalent) residue of a heterocyclic ring having 5 to 30 (preferably 5 to 20, and more preferably 5 to 12) ring atoms is a divalent to tetravalent group obtained by eliminating 1 to 3 hydrogen atoms from the heterocyclic group having 5 to 30 ring atoms as described regarding $R_1$ to $R_{12}$. A divalent to tetravalent residue of a ring selected from pyridine, pyrimidine, pyridazine, pyrazine, quinoline, isoquinoline, and triazine is preferable; a pyridinediyl group, a pyrimidinediyl group, a pyridazinediyl group, a pyrazinediyl group, a quinolinediyl group, and a triazinediyl group are more preferable; and a pyrimidine-2,5-diyl group, a pyrimidine-2,4-diyl group, a pyridazine-3,6-diyl group, a pyrazine-2,5-diyl group, a pyridine-2,4-diyl group, a pyridine-2,5-diyl group, a pyridine-2,6-diyl group, a quinoline-5,8-diyl group, a quinoline-4,7-diyl group, and a triazine-2,4-diyl group are still more preferable.

The divalent to tetravalent residue of a ring formed through bonding of 2 to 3 rings selected from the aromatic hydrocarbon ring and heterocyclic ring via a single bond is preferably a divalent to tetravalent residue of the following compounds. Two to four free bonds may be bounded to any position of the aromatic hydrocarbon ring and the heterocyclic ring.

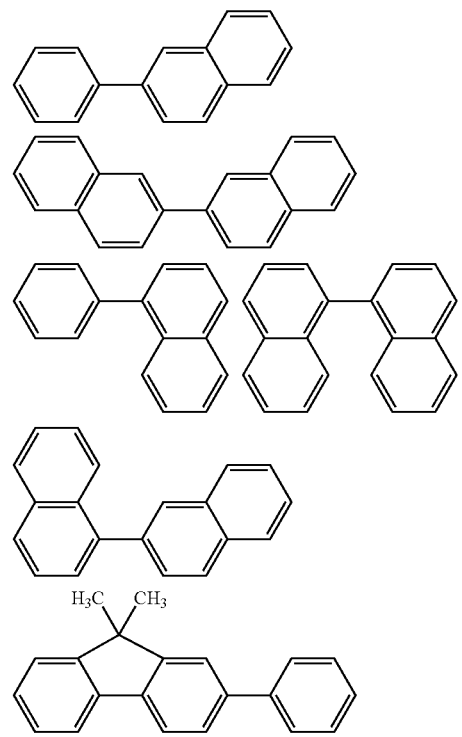

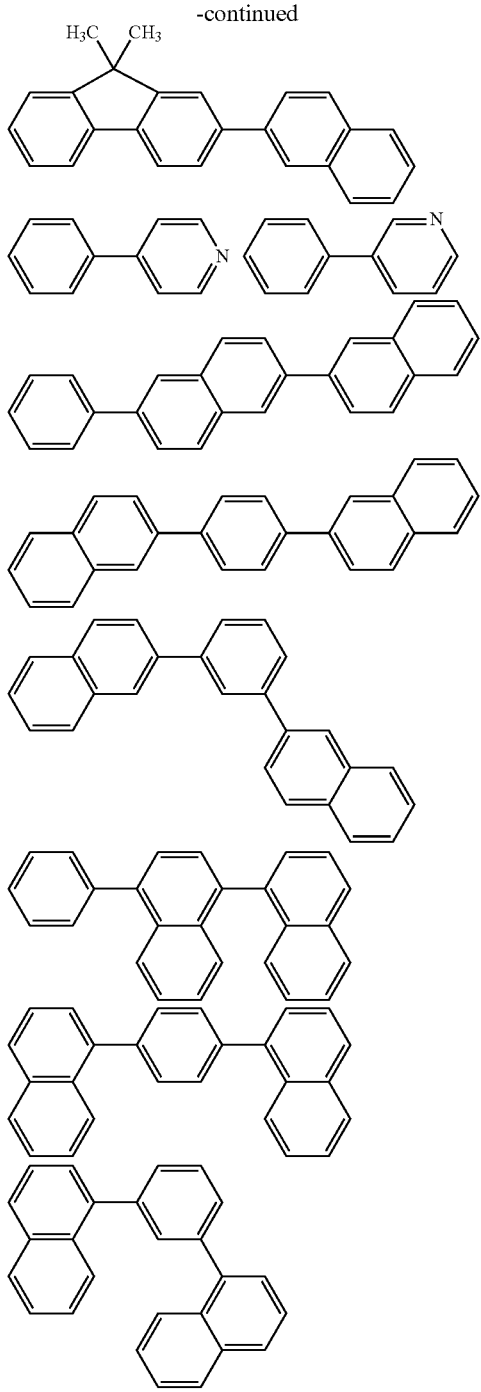
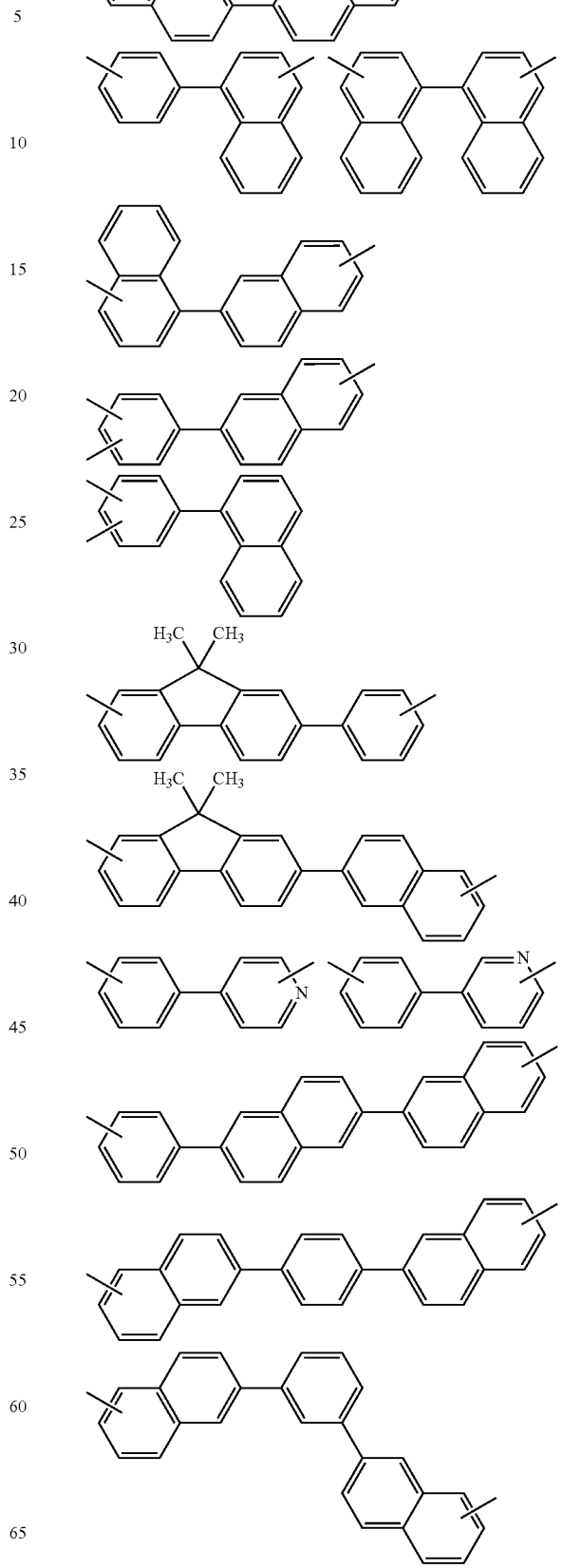
The following residues are preferable as the divalent residue. Each of the two free bonds may be bonded at any position of the benzene ring in which each free bond is contained, and either of the two free bonds may be bonded to the benzofluoranthene skeleton or may be bonded to HAr.
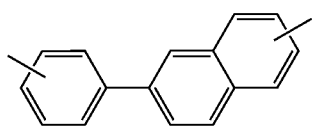

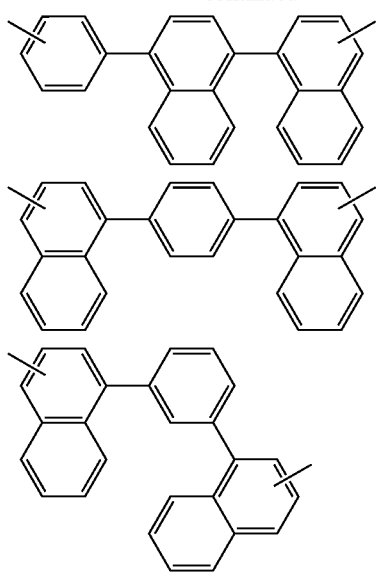
More preferred divalent residues are shown below. Either of the two free bonds may be bonded to the benzofluoranthene skeleton or may be bonded to HAr.
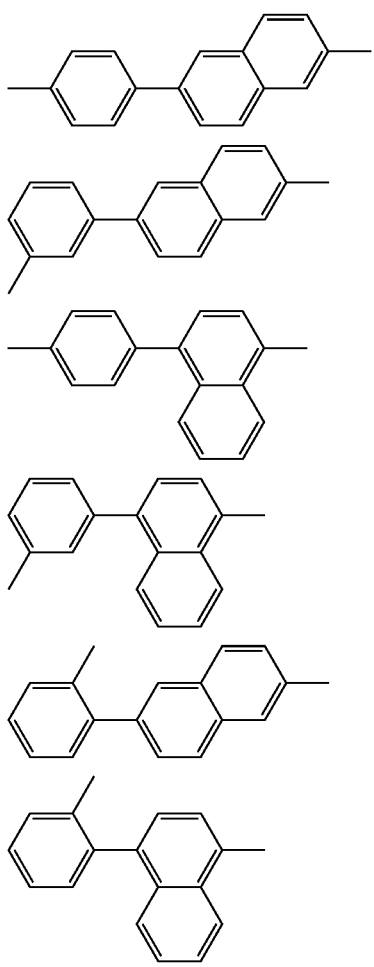
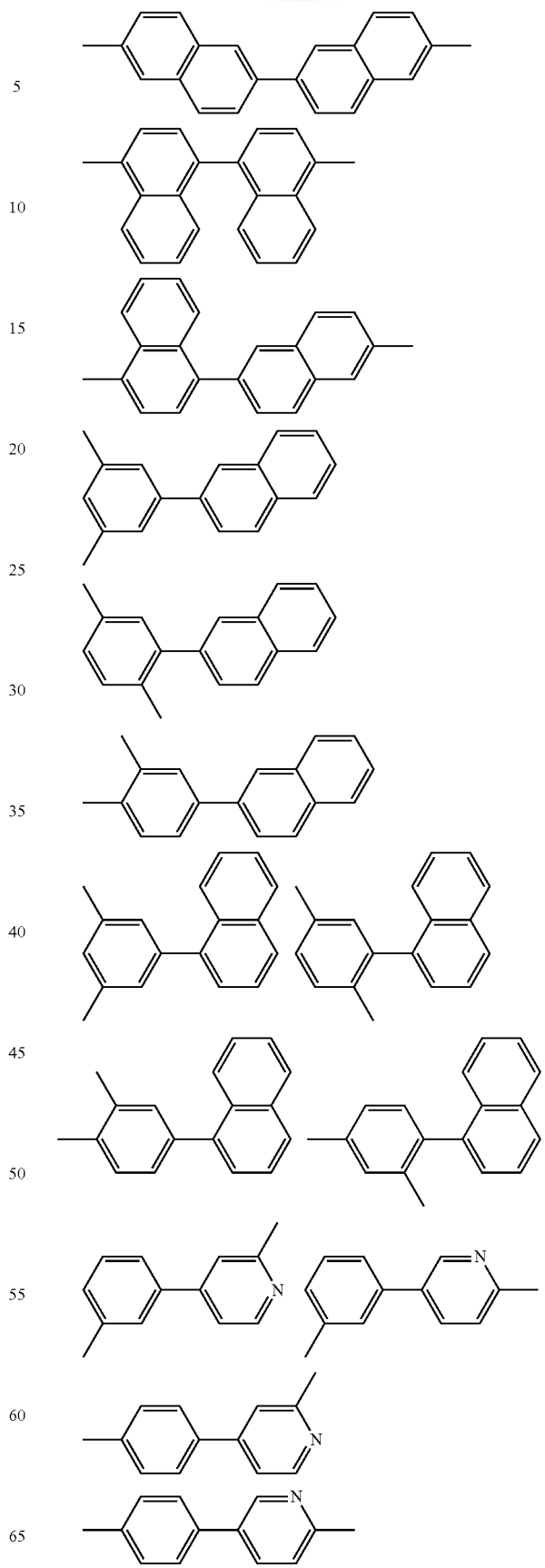

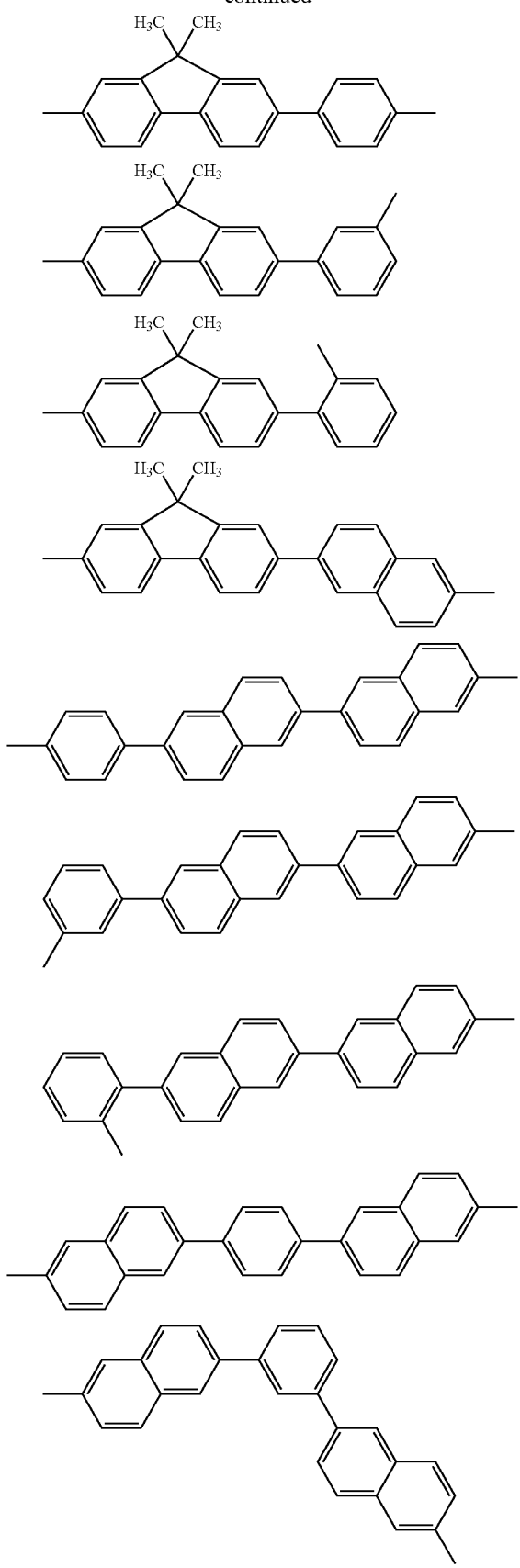

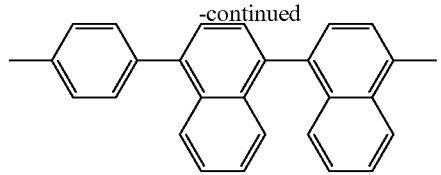

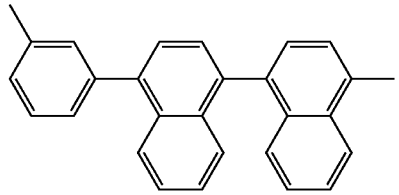

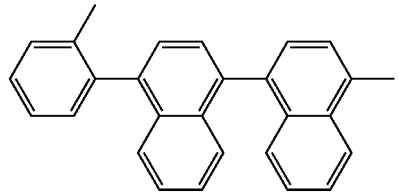

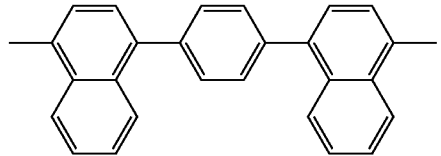

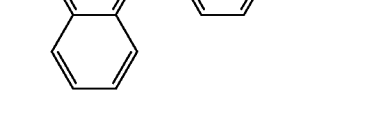

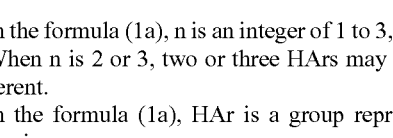

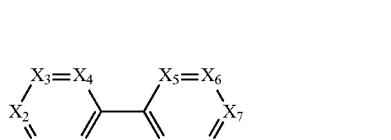

In the formula (1a), n is an integer of 1 to 3, and preferably 1. When n is 2 or 3, two or three HArs may be the same or different.

In the formula (1a), HAr is a group represented by the following

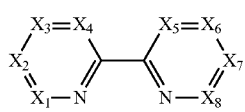

(2)

Each of $X_1$ to $X_8$ independently represents a nitrogen atom or $CR_{13}$, and at least one of $X_1$ to $X_8$ is $CR_{13}$; and each of $R_{13}$s independently represents a hydrogen atom, a halogen atom, a substituted or unsubstituted alkyl group having 1 to 10 carbon atoms, a substituted or unsubstituted cycloalkyl group having 3 to 8 ring carbon atoms, a substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted mono- or dialkylamino group having 1 to 20 carbon atoms, a substituted or unsubstituted aryl group having 6 to 30 ring carbon atoms, a substituted or unsubstituted heterocyclic group having 5 to 30 ring atoms, a substituted or unsubstituted arylthio group having 6 to 20 ring carbon atoms, or a substituted or unsubstituted mono- or diarylamino group having 6 to 40 ring carbon atoms, provided that one of $R_{13}$s is a single bond and is bonded to L.

Examples of the halogen atom, the substituted or unsubstituted alkyl group having 1 to 10 carbon atoms, the substituted or unsubstituted cycloalkyl group having 3 to 8 ring carbon atoms, the substituted silyl group having 3 to 30 carbon atoms, the cyano group, the substituted or unsubstituted alkoxy group having 1 to 20 carbon atoms, the substituted or unsubstituted aryloxy group having 6 to 20 ring carbon atoms, the substituted or unsubstituted aryl group having 6 to 30 ring carbon atoms, and the substituted or unsubstituted heterocyclic group having 5 to 30 ring atoms are the same as those described above regarding $R_1$ to $R_{12}$.

The alkylthio group having 1 to 20 carbon atoms is represented by $—SY^1$, and the mono- or dialkylamino group having 1 to 20 carbon atoms is represented by $—NHY^2$ or $—NY^2Y^3$, respectively. $Y^1$, $Y^2$, and $Y^3$ are the same as Y described above. Examples of the optional substituent of the alkylthio group or the mono- or dialkylamino group include substituents as described later.

The arylthio group having 6 to 20 (preferably 6 to 10) ring carbon atoms is a group represented by $—SAr^1$, and $Ar^1$ is the same as Ar described above. Examples of the substituted arylthio group include aryloxy groups having a substituent as described later.

The mono- or diarylamino group having 6 to 40 (preferably 6 to 20) ring carbon atoms is represented by $—NHAr^1$ or $—NAr^2Ar^3$, respectively. $Ar^1$, $Ar^2$, and $Ar^3$ are the same as Ar described above. Examples of the substituted mono- or diarylamino group include mono- or diarylamino groups having a substituent as described later.

As $R_{13}$, a hydrogen atom, a substituted or unsubstituted aryl group having 6 to 30 ring carbon atoms, and a substituted or unsubstituted heterocyclic group having 5 to 30 ring atoms are preferable; and a hydrogen atom, a phenyl group, a 2-, 3- or 4-methoxyphenyl group, a 2-, 3- or 4-trimethylsilylphenyl group, a 2-, 3- or 4-trifluoromethylphenyl group, a 2-, 3- or 4-cyanophenyl group, a 2-, 3- or 4-fluorophenyl group, a 1-naphthyl group, a 2-naphthyl group, a 2-pyridyl group, a 3-pyridyl group, a 4-pyridyl group, a 2-pyrimidinyl group, a 2-triazinyl group, a 2-bipyridyl group, a 9-phenanthryl group, a 1-pyrenyl group, a 3-fluoranthenyl group, and an 8-fluoranthenyl group are especially preferable.

Two or more $R_{13}$s may be bonded to each other to form a substituted or unsubstituted, saturated or unsaturated group capable of forming a part of the ring. However, the case where each of $X_4$ and $X_5$ is $CR_{13}$, and the $R_{13}$s are bonded to each other to form a substituted or unsubstituted methylene group is excluded. Two or more $R_{13}$s may not be adjoined to each other, and for example, in the case where each of $X_1$ and $X_4$ is $CR_{13}$, the two $R_{13}$s may be bonded to each other to form a ring-forming substituted or unsubstituted, saturated or unsaturated divalent group. Also, in the case where each of $X_1$, $X_2$, and $X_3$ is $CR_{13}$, the three $R_{13}$s may be bonded to each other to form a ring-forming substituted or unsubstituted, saturated or unsaturated trivalent group.

The case where two $R_{13}$ bonded to the adjoining two carbon atoms, respectively are bonded to each other, and the case where each of $X_4$ and $X_5$ is $CR_{13}$, and the $R_{13}$s are bonded to each other (provided that the case where the $R_{13}$s form a substituted or unsubstituted methylene group is excluded) are especially preferable. Also, the ring-forming substituted or unsubstituted, saturated or unsaturated group may contain one or two or more hetero atoms selected from a nitrogen atom, an oxygen atom, and a sulfur atom in a main skeleton thereof.

Examples of the ring in which two or more $R_{13}$s are bonded to each other include a carbon 6-membered ring, a carbon 7-membered ring, a hetero 5-membered ring containing one oxygen atom, with the other being carbon atoms, a hetero 6-membered ring containing one oxygen atom, with the other being carbon atoms, a hetero 7-membered ring containing one oxygen atom, with the other being carbon atoms, a hetero 5-membered ring containing one nitrogen atom, with the other being carbon atoms a hetero 6-membered ring containing one nitrogen atom, with the other being carbon atoms, a hetero 5-membered ring containing one sulfur atom, with the other being carbon atoms, a hetero 5-membered ring containing one oxygen atom and one nitrogen atom, with the other being carbon atoms, and so on.

In the case where two or more $R_{13}$s are bonded to each other to form a ring, a ring number is preferably 1 to 8, more preferably 1 to 4, and especially preferably 1 or 2. In the case where two or more rings are formed, these rings may be the same or different.

Examples of the group represented by the formula (2) in the case where two or more $R_{13}$s are bonded to each other to form a ring (optional substituents are omitted) include residues of the following compounds.

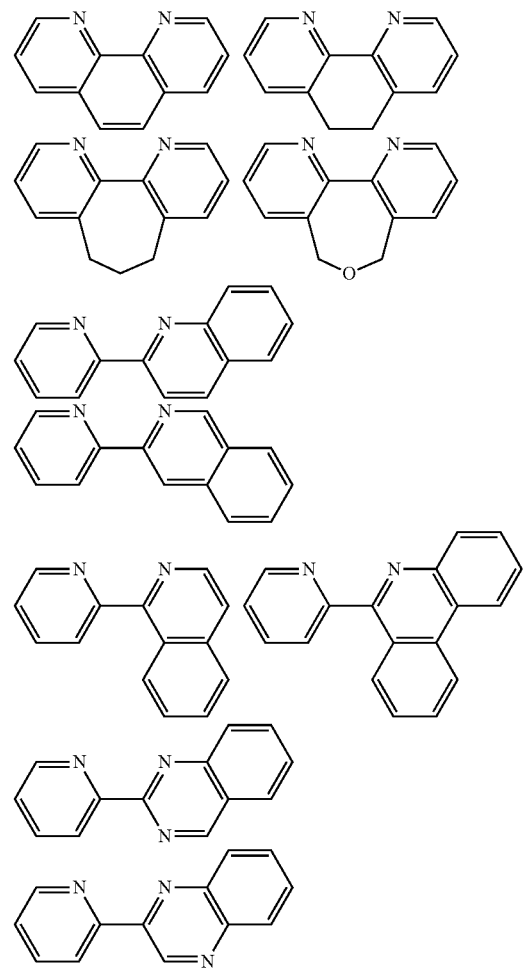

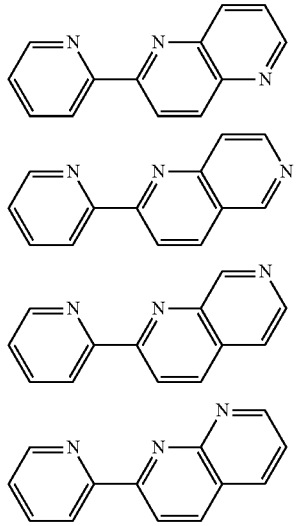
The above residues are preferably the following residues. The free bond may be bonded at any position of the aromatic ring containing it (provided that a nitrogen atom is excluded).
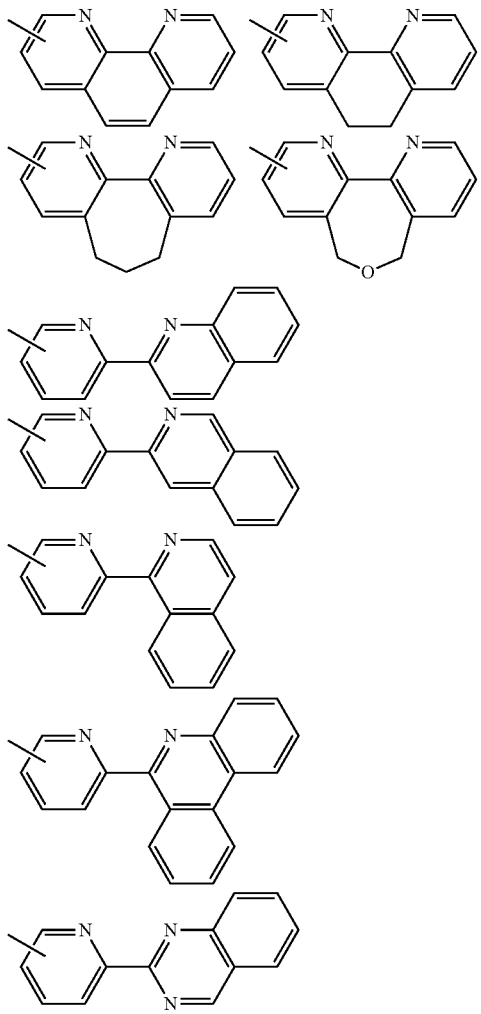
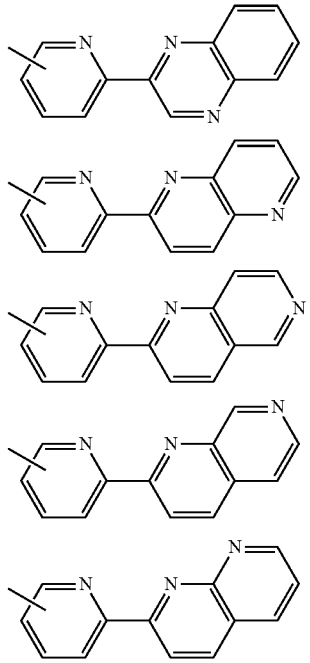
More preferred residues are as follows.
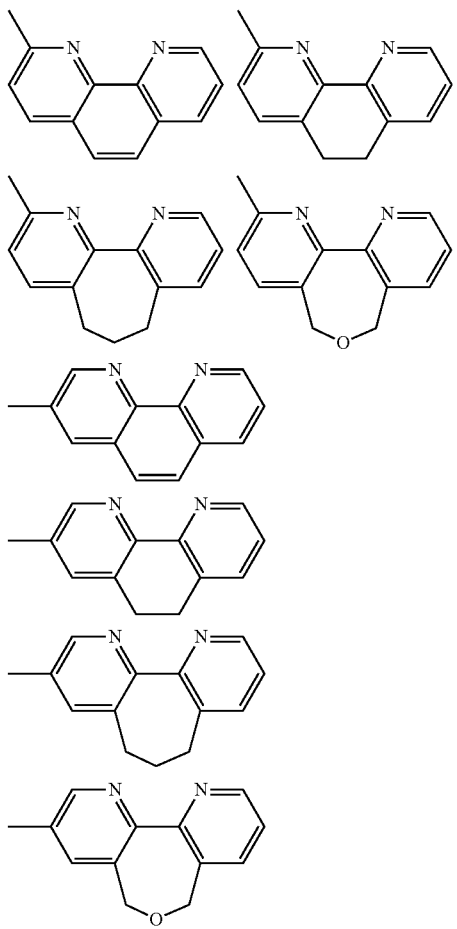

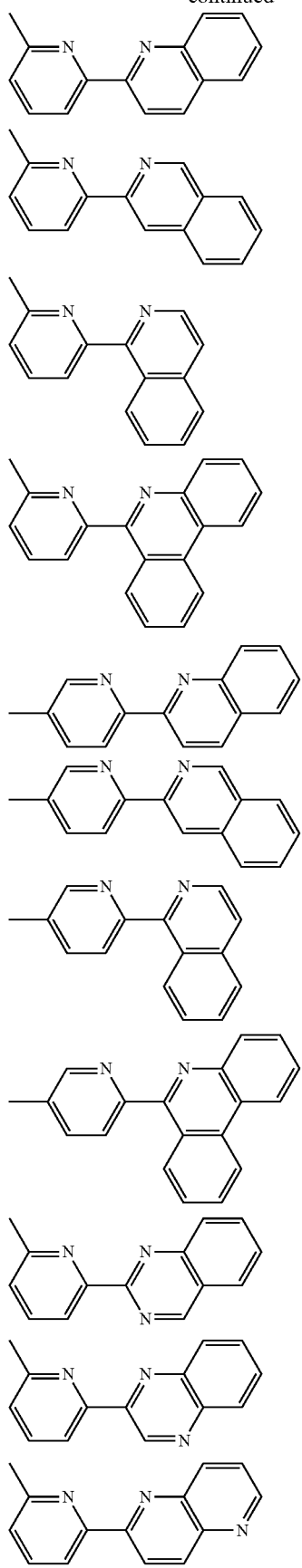
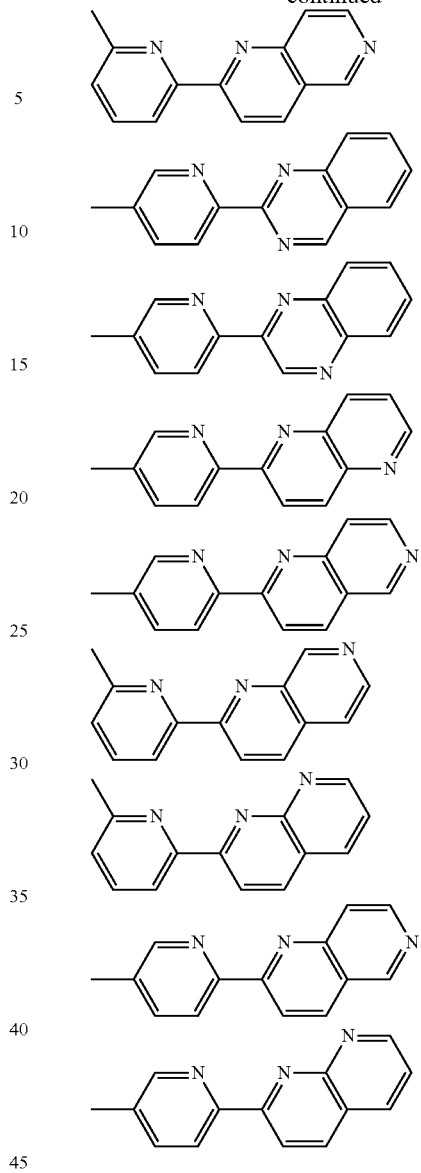
HAr in the formula (2) is preferably represented by any of the following formulae (3) to (7).
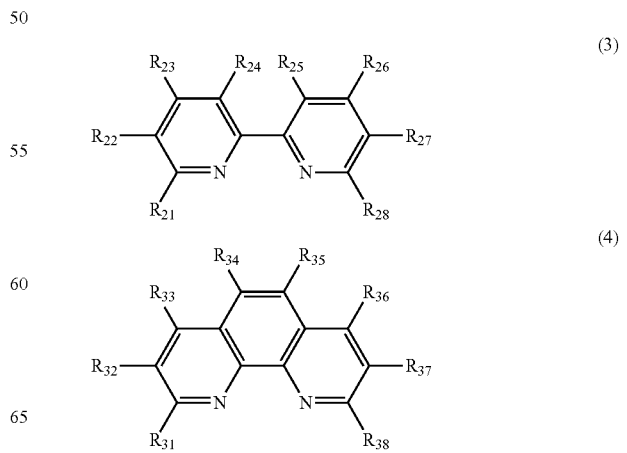

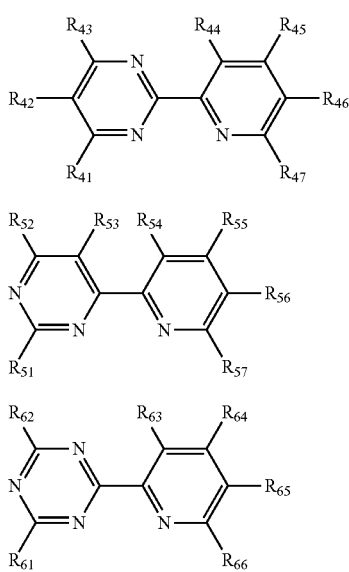

(5)

(6)

(7)

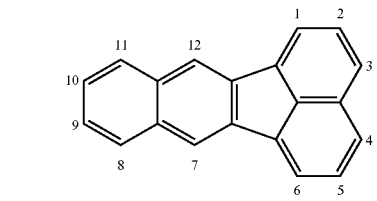 [SMILES: c1ccc2cc3c(cc2c1)-c1cccc2cccc-3c12]

The benzo[k]fluoranthene derivative represented by the formula (1) is preferably represented by the following formula (8).

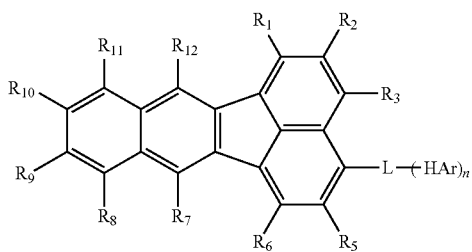

(8)

In the formula, $R_1$ to $R_3$, $R_5$ to $R_{12}$, HAr, L, and n are the same as those in the formula (1).

The benzo[k]fluoranthene derivative represented by the formula (1) is more preferably represented by the following formula (9).

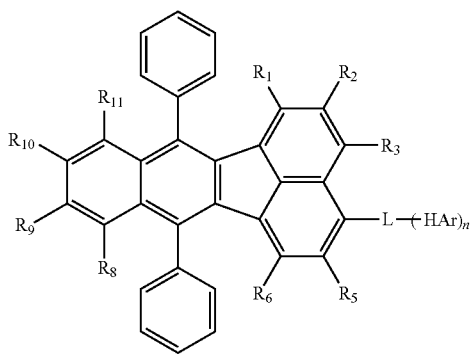

(9)

In the formula, $R_1$ to $R_3$, $R_5$, $R_6$, $R_8$ to $R_{11}$, HAr, L, and n are the same as those in the foregoing formula (1).

In the formulae (3) to (7), each of $R_{21}$ to $R_{66}$ is a hydrogen atom, a halogen atom, or a group selected from the groups described regarding $R_{13}$.

In the formula (3), two or more of $R_{21}$ to $R_{28}$ may be bonded to each other to form a ring-forming substituted or unsubstituted, saturated or unsaturated group, provided that any one of $R_{21}$ to $R_{28}$, preferably one of $R_{21}$, $R_{22}$, $R_{24}$, $R_{25}$, $R_{27}$, and $R_{28}$, and more preferably one of $R_{21}$, $R_{22}$, $R_{27}$, and $R_{28}$ is a single bond and is bonded to L, and the case where $R_{24}$ and $R_{25}$ are bonded to each other to form a substituted or unsubstituted methylene group is excluded.

In the formula (4), two or more of $R_{31}$ to $R_{38}$ may be bonded to each other to form a ring-forming substituted or unsubstituted, saturated or unsaturated group, provided that any one of $R_{31}$ to $R_{38}$, and preferably one of $R_{31}$ and $R_{38}$ is a single bond and is bonded to L.

In the formula (5), two or more of $R_{41}$ to $R_{47}$ may be bonded to each other to form a ring-forming saturated or unsaturated group, provided that any one of $R_{41}$ to $R_{47}$, and preferably one of $R_{41}$, $R_{43}$, and $R_{47}$ is a single bond and is bonded to L.

In the formula (6), two or more of $R_{51}$ to $R_{57}$ may be bonded to each other to form a ring-forming substituted or unsubstituted, saturated or unsaturated group, provided that any one of $R_{51}$ to $R_{57}$, and more preferably one of $R_{51}$, $R_{52}$, and $R_{57}$ is a single bond and is bonded to L, and the case where $R_{53}$ and $R_{54}$ are bonded to each other to form a substituted or unsubstituted methylene group is excluded.

In the formula (7), two or more of $R_{61}$ to $R_{66}$ may be bonded to each other to form a ring-forming substituted or unsubstituted, saturated or unsaturated group, provided that any one of $R_{61}$ to $R_{66}$, and preferably one of $R_{61}$, $R_{62}$, and $R_{66}$ is a single bond and is bonded to L.

In the formulae (3) to (7), details of the case where two or more $R_x$s are bonded to each other to form a substituted or unsubstituted, saturated or unsaturated group are those described regarding $R_{13}$.

-L-(HAr)$_n$ represented by the formula (1a) is preferably bonded at any one of the 3-, 4-, 7- and 12-positions, and especially preferably bonded at the 3- or 4-position of the benzo[k]fluoranthene skeleton of the formula (1).

In the benzo[k]fluoranthene derivative represented by the formula (1), when each of $R_3$ and $R_4$ is an active site of the benzo[k]fluoranthene, and $R_3$ or $R_4$ is a substituent, and preferably -L-(HAr)$_n$, the stability of the benzo[k]fluoranthene derivative tends to be enhanced. When the benzo[k]fluoranthene derivative represented by the formula (8) or (9), whose stability has been enhanced, is included, the lifetime of the organic EL device tends to be more enhanced.

In the case where L of the benzo[k]fluoranthene derivative represented by the formula (1), (8) or (9) is a single bond, since a distance between the benzofluoranthene skeleton (charge transporting site) and —(HAr)$_n$ (electron injecting site) is short, it may be considered that the charge transfer in the molecule becomes smooth (the electron can transfer to the charge transport site within a short period of time). In consequence, it may be considered that the driving voltage is reduced.

In the case where L of the benzo[k]fluoranthene derivative of the present invention is a divalent to tetravalent residue of a substituted or unsubstituted aromatic hydrocarbon ring having 6 to 30 ring carbon atoms, a divalent to tetravalent residue of a substituted or unsubstituted heterocyclic ring having 5 to 30 ring atoms, or a divalent to tetravalent residue of a ring formed through bonding of 2 to 3 rings selected from the foregoing aromatic hydrocarbon ring and heterocyclic ring via a single bond, since a distance between the benzo[k]fluoranthene skeleton and —(HAr)$_n$ is long, it may be considered that the electronic participation of the benzofluoranthene skeleton and —(HAr)$_n$ can be reduced. Though there may be the case where it takes a time for the charge transfer is the molecule, it may be considered that a mutual interference of a function between the electron injecting site and the charge transporting site can be reduced. As a result, it may be considered that the interference at the time of intermolecular transfer vanishes, whereby the driving voltage is reduced.

In the benzo[k]fluoranthene derivative represented by the formula (1) or (8), it is preferable that each of $R_7$ and $R_{12}$ independently represents an aryl group having 6 to 30 ring carbon atoms (preferably from 6 to 20, and more preferably from 6 to 12), and it is especially preferable that both of $R_7$ and $R_{12}$ are a phenyl group. When each of $R_7$ and $R_{12}$ is an aryl group, it may be considered that the planarity of the benzo[k]fluoranthene skeleton is enhanced. In the benzo[k]fluoranthene derivative whose planarity has been enhanced, it may be considered that overlap of the molecules each other becomes large, so that the distance between the molecules becomes short, whereby charge transporting properties of the benzo[k]fluoranthene derivative can be more enhanced.

The hydrogen atoms of the benzo[k]fluoranthene derivative of the present invention include light hydrogen and heavy hydrogen. Also, in the present specification, the "ring carbon atoms" means a carbon atom constituting a saturated ring, an unsaturated ring, or an aromatic ring. The "ring atoms" means a carbon atom and a hetero atom constituting a hetero saturated ring, a hetero unsaturated ring, or a hetero aromatic ring.

Examples of the optional substituent in the case of referring to "substituted or unsubstituted ..." include a halogen atom, a substituted or unsubstituted alkyl group having 1 to 10 carbon atoms, a substituted or unsubstituted cycloalkyl group having 3 to 8 ring carbon atoms, a substituted or unsubstituted, substituted silyl group having 3 to 30 carbon atoms, a cyano group, a substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, a substituted or unsubstituted mono- or dialkylamino group having 1 to 20 carbon atoms, a substituted or unsubstituted aryl group having 6 to 30 ring carbon atoms, and a substituted or unsubstituted heterocyclic group having 5 to 30 ring atoms, unless otherwise restricted.

Specific examples thereof include a fluorine atom, a methyl group, a 1-, 2- or 3-pyridyl group, a trimethylsilyl group, a methoxy group, a cyano group, a 1- or 2-naphthyl group, a 2-, 3- or 4-methoxyphenyl group, a 2-, 3- or 4-trimethylsilylphenyl group, a 2-, 3- or 4-cyanophenyl group, a 2-pyrimidyl group, a 2-triazinyl group, a 3- or 4-bipyridyl group, and so on.

It may be considered that the benzo[k]fluoranthene derivative of the present invention as described above in detail has high charge transporting properties because it contains a benzo[k]fluoranthene skeleton having high planarity, and the molecules well overlap each other. In particular, the benzo[k]fluoranthene skeleton has higher charge transporting properties than, for example, a fluoranthene skeleton because of its high planarity.

Also, the benzo[k]fluoranthene skeleton has high charge durability, and in the case of using the benzo[k]fluoranthene derivative of the present invention for an organic EL device, an enhancement of the lifetime can be expected. Though there may be the case where a hole flows to the side of an electron injecting layer, since the benzo[k]fluoranthene derivative of the present invention has hole resistance, it may be considered that it can prevent deterioration of the device.

In view of the fact that the benzo[k]fluoranthene derivative of the present invention has a benzo[k]fluoranthene skeleton, an affinity (Af) becomes large, and for example, in the case where it is used for an electron transporting layer, an interaction with an adjoining metal complex layer or reducing dopant layer becomes high, so that it can be expected that satisfactory electron injecting properties are revealed. From the foregoing reasons, it may be considered that the benzo[k]fluoranthene derivative of the present invention lowers the driving voltage of the organic EL device.

Since a heterocyclic ring, such as a pyridine ring and the like, can coordinate to a metal atom using a lone pair on a nitrogen atom thereof, it may be considered that an affinity with an electrode becomes strong. It may be considered that in the bipyridine structure or phenanthroline structure contained in HAr of the benzo[k]fluoranthene derivative of the present invention, two nitrogen atoms are present at positions at which a chelate with a lithium ion or the like is easily formed. In particular, since two nitrogen atoms of the bipyridine structure are rotatable around the single bond, it may be considered that a distance therebetween can be varied depending upon an ionic radius of a metal ion to be coordinated. In this way, since HAr contains two nitrogen atoms at positions at which a chelate with a metal ion is easily formed, it is easy to capture the metal ion on the cathode side. Therefore, it may be considered that HAr can enhance the electron injecting properties of the organic EL device as compared with a benzoimidazolyl group and other heterocyclic groups.

Also, in the case of having the following diazafluorenyl group:

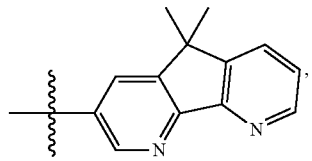 [SMILES: *c1cnc2c(c1)C(C)(C)c1cccnc1-2]

in view of the fact that a 5-membered ring structure connected with a methylene group in the center is taken, it may be considered that a distance between the two nitrogen atoms increases as compared with the case of the bipyridine structure, and for example, it becomes hard to capture an ion having a smaller ionic radius, such as a lithium ion or the like.

In the light of the above, the benzo[k]fluoranthene derivative of the present invention is a compound having a benzo[k]fluoranthene structure and a bipyridine structure or an analogous structure thereto in one molecule, and it is a compound having excellent charge transporting properties, charge durability and electron injecting properties at the same time.

Specific examples of the benzo[k]fluoranthene derivative of the formula (1) of the present invention are shown below, but it should not be construed that the present invention is limited to only the following specific examples.

25 26
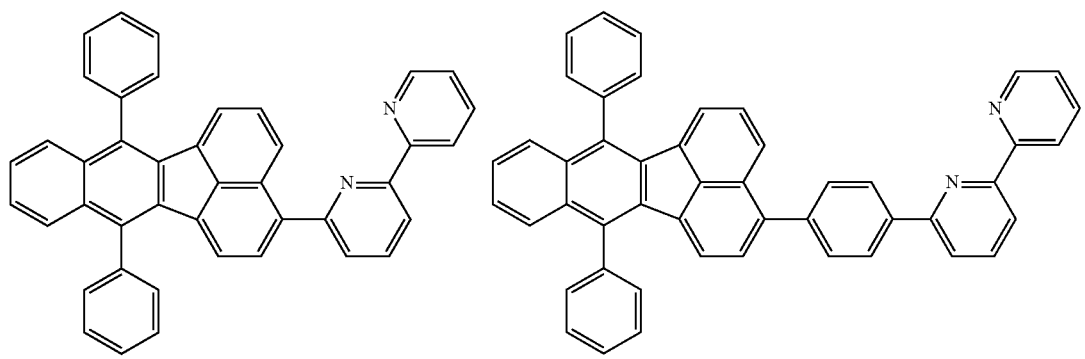
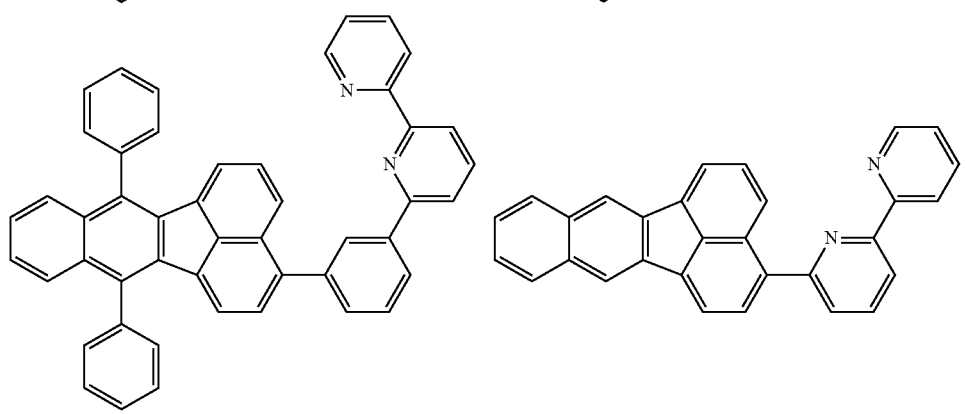
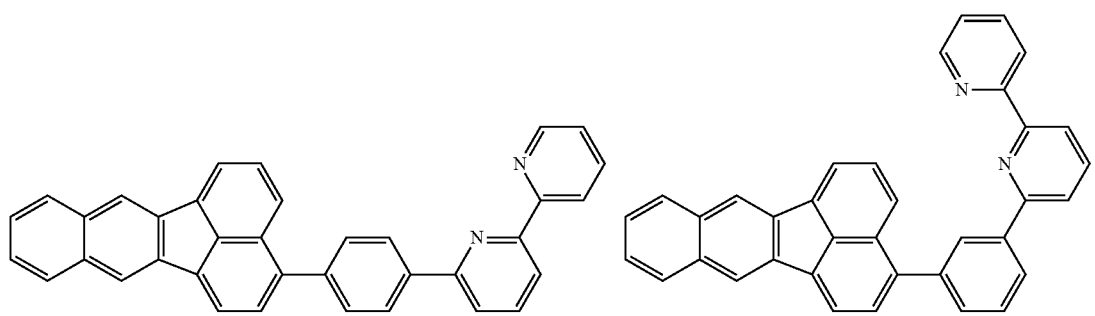
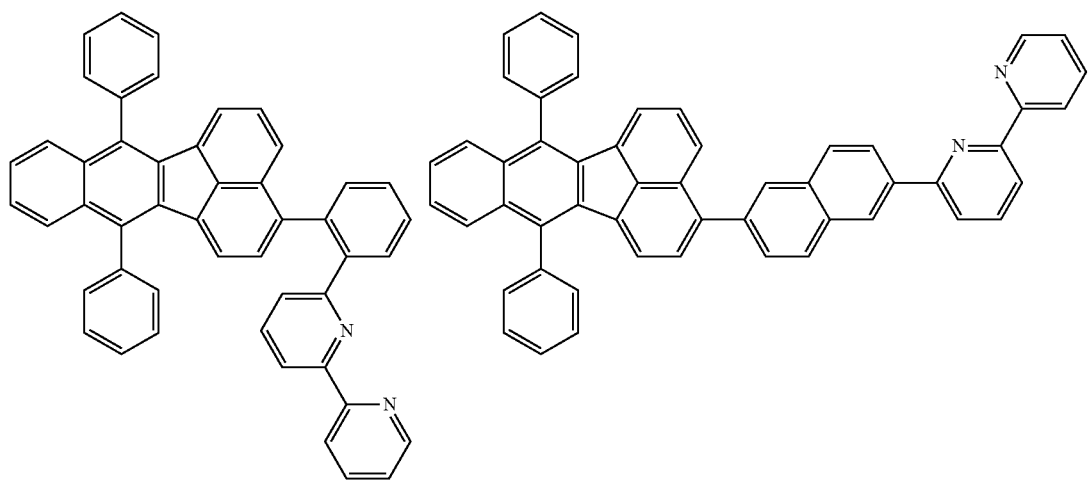

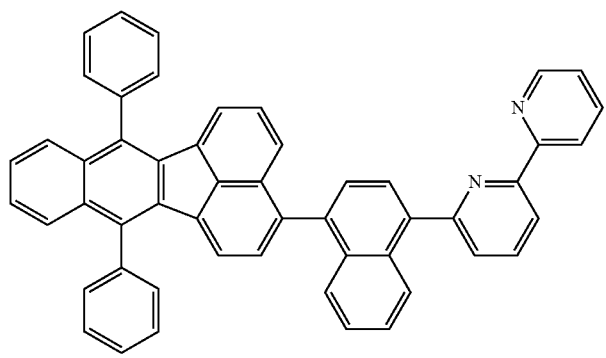
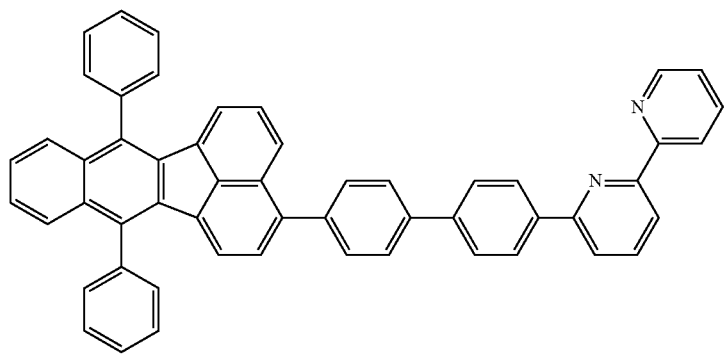
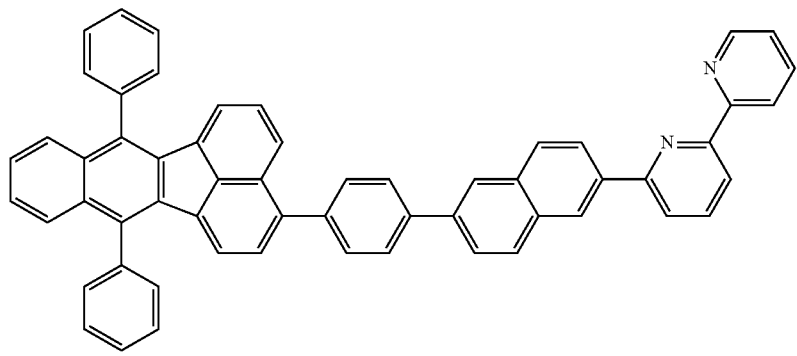
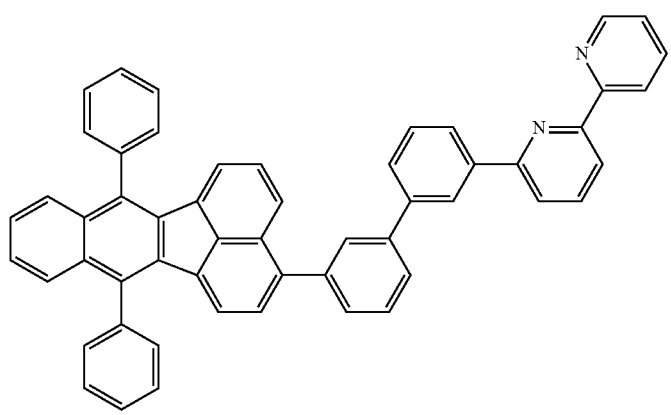

-continued
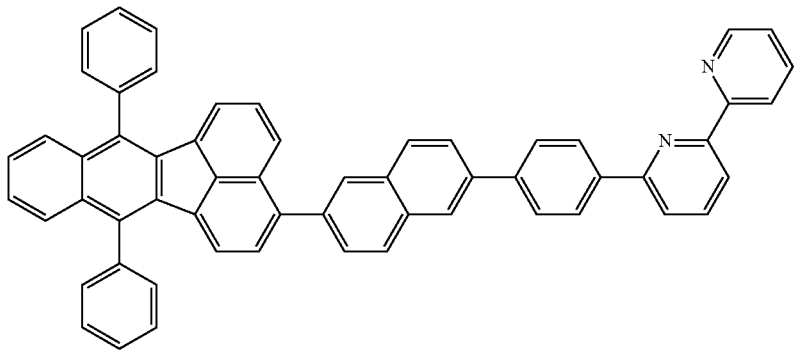
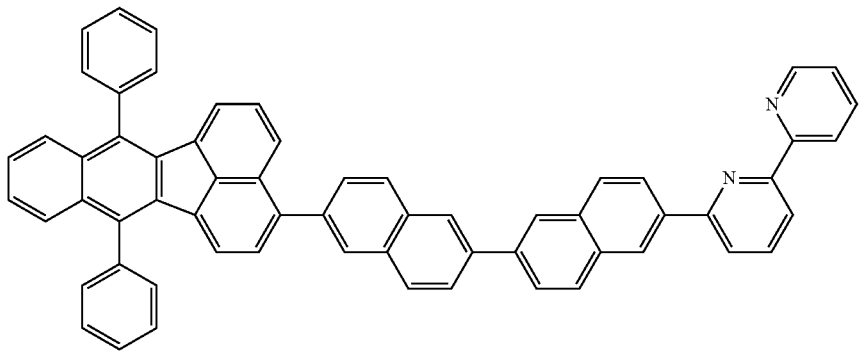
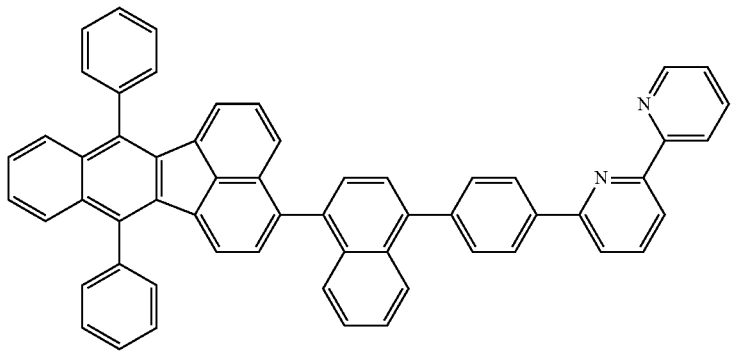
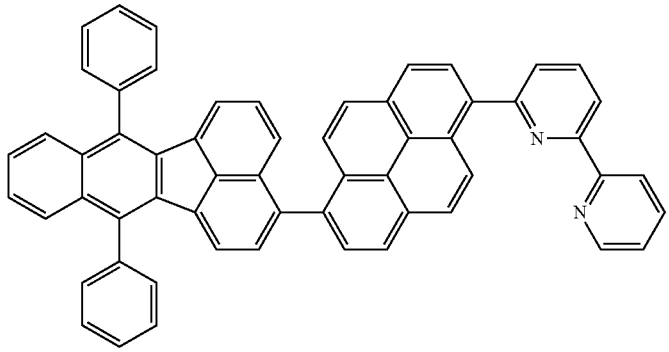

-continued
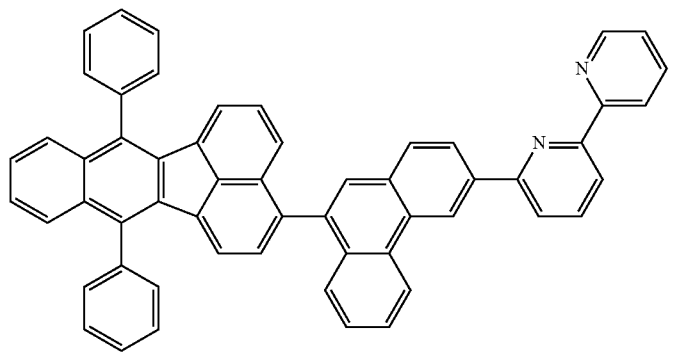
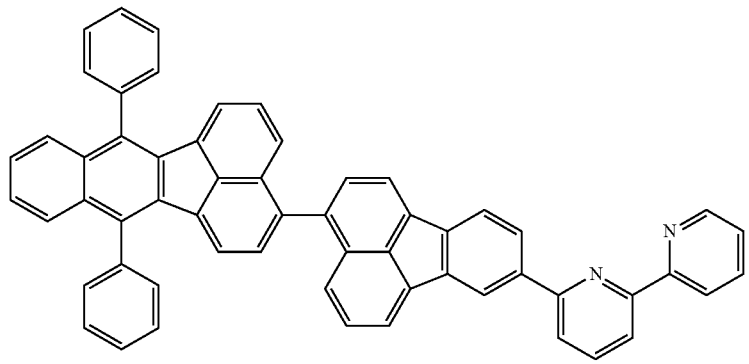
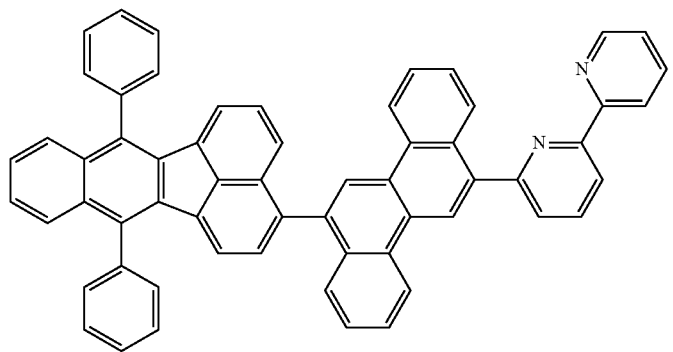
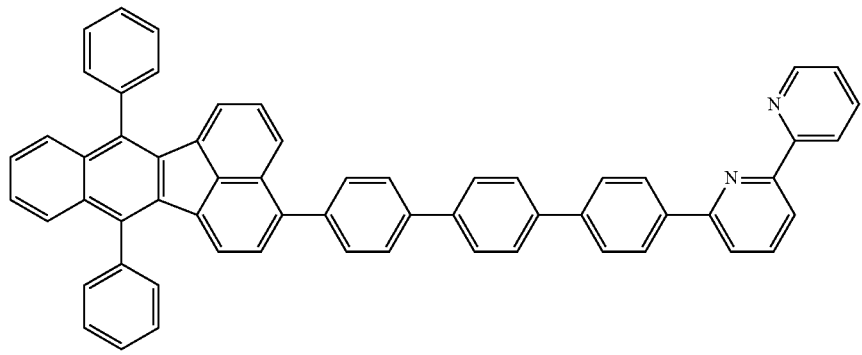

-continued
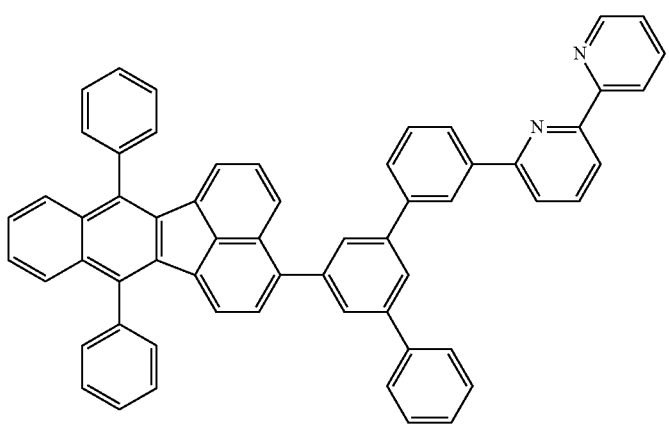
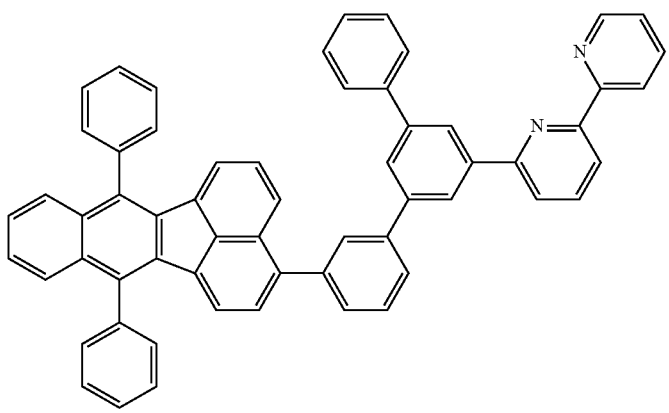
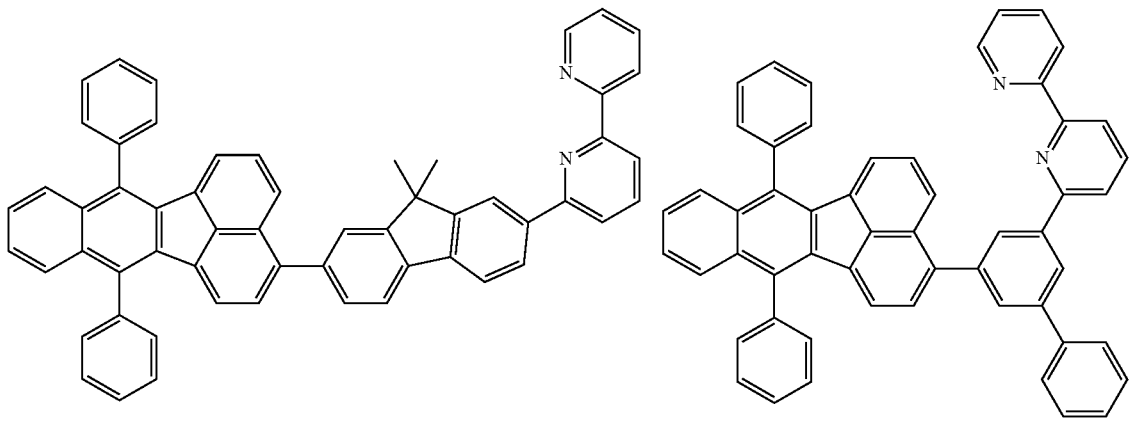

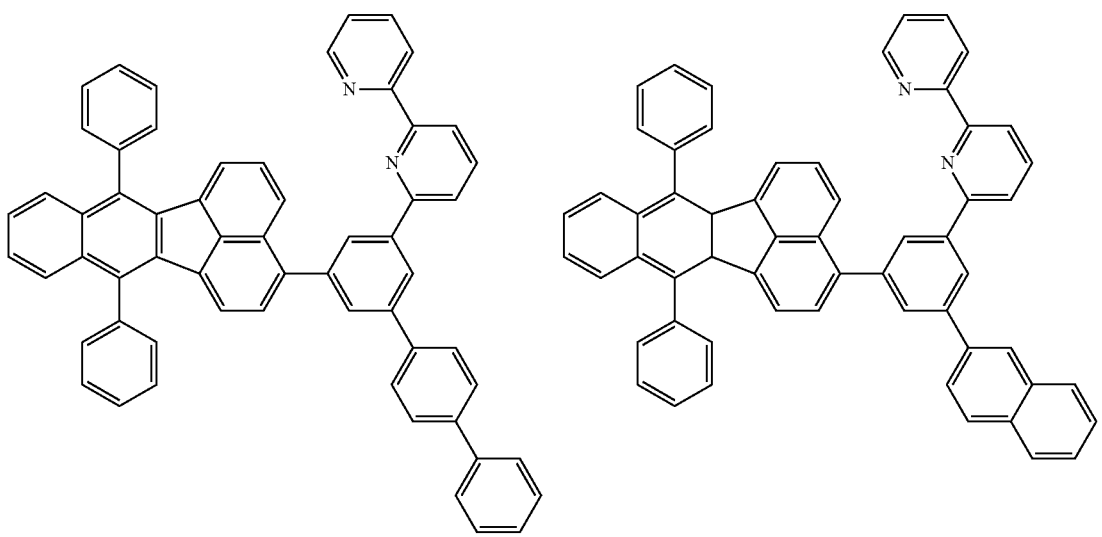
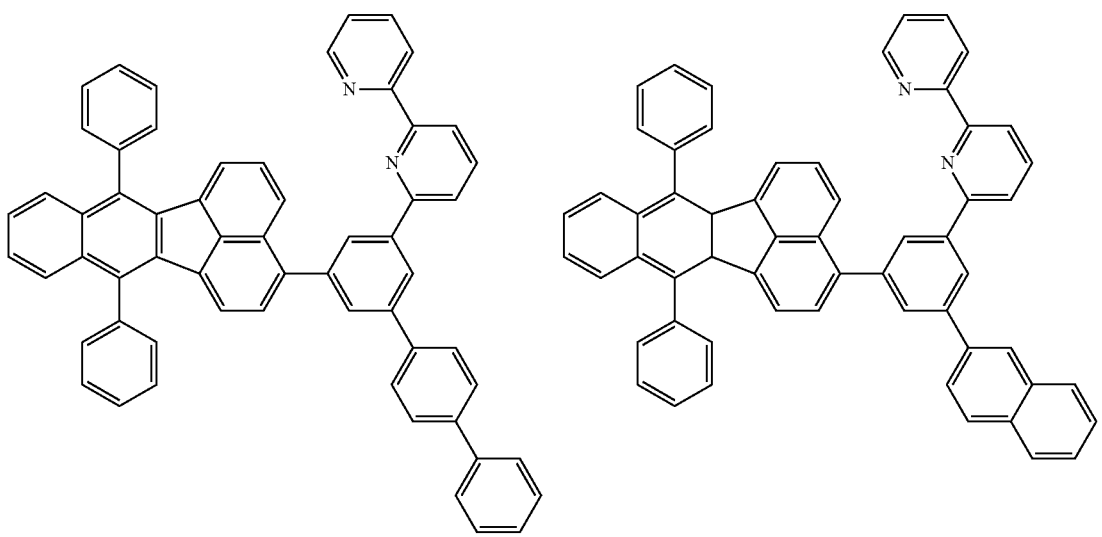
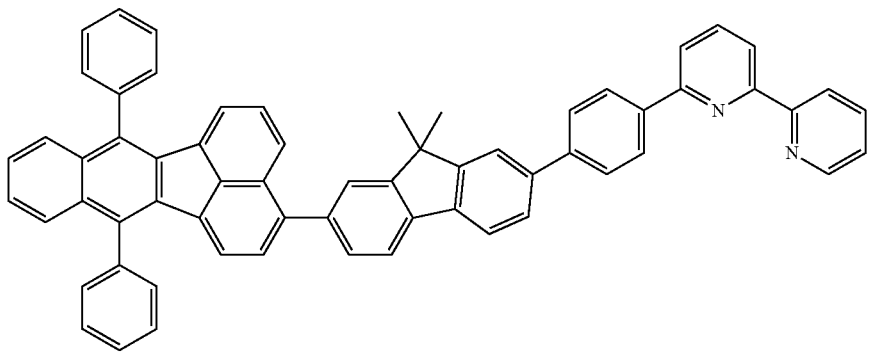
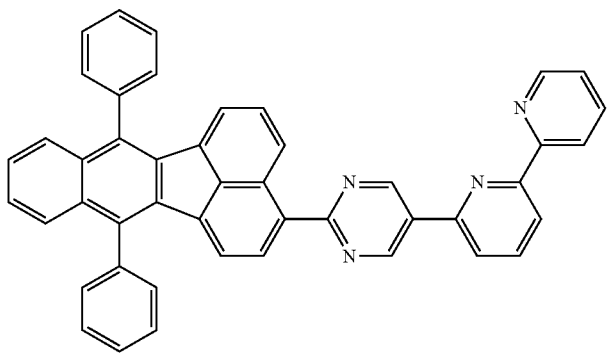
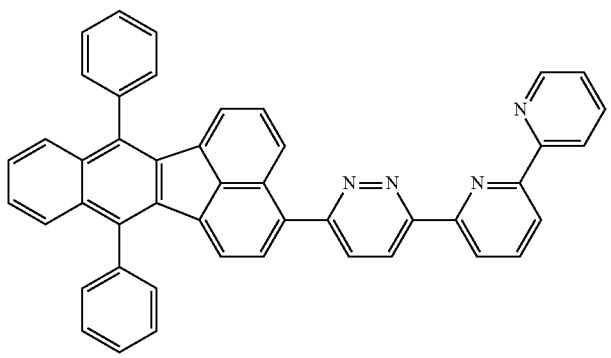

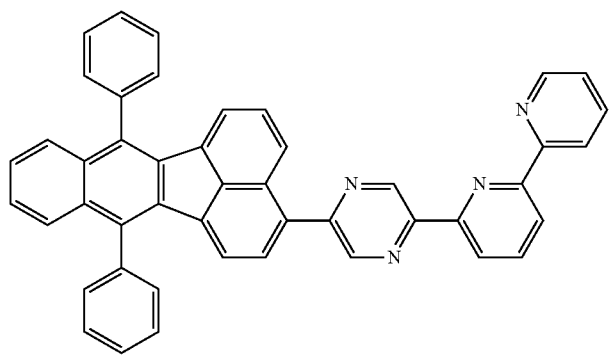
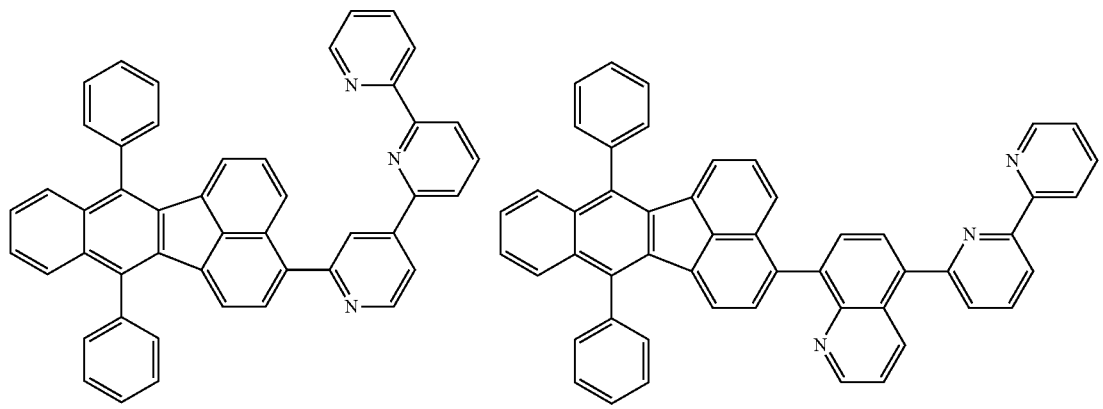
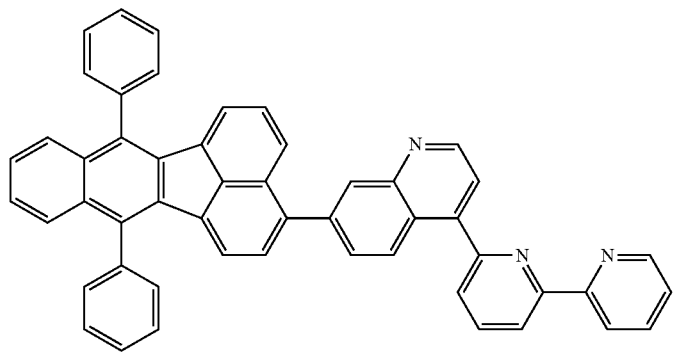
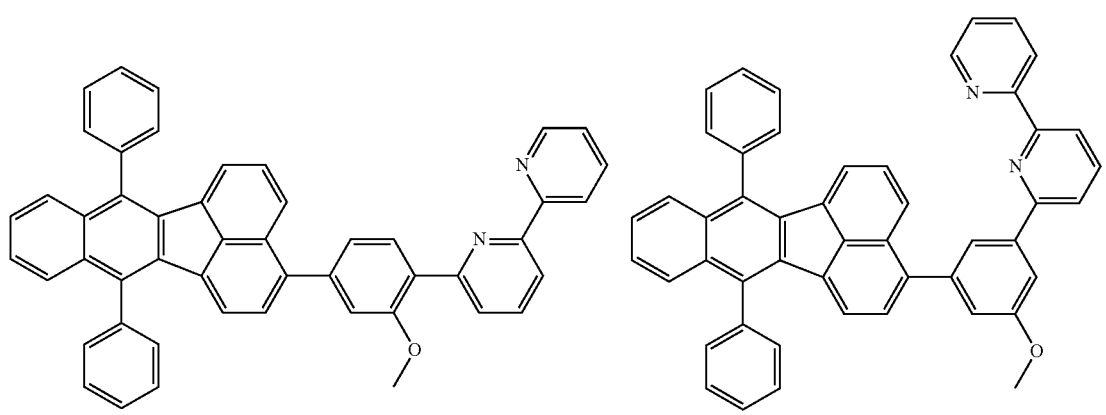

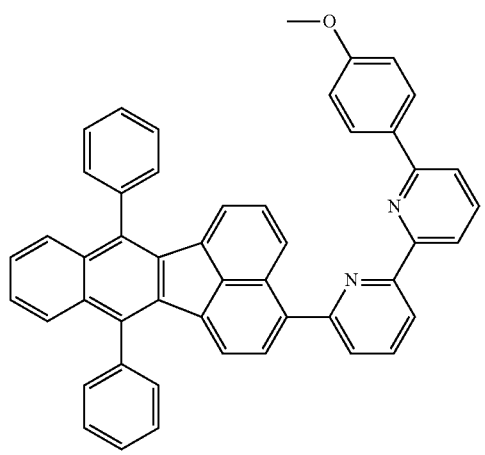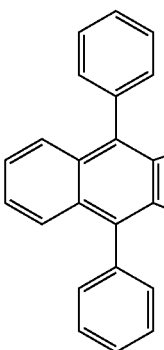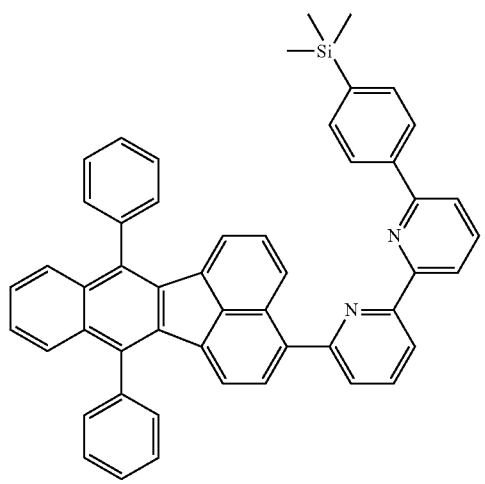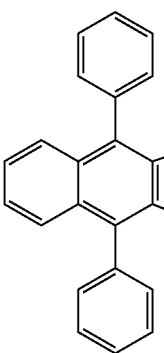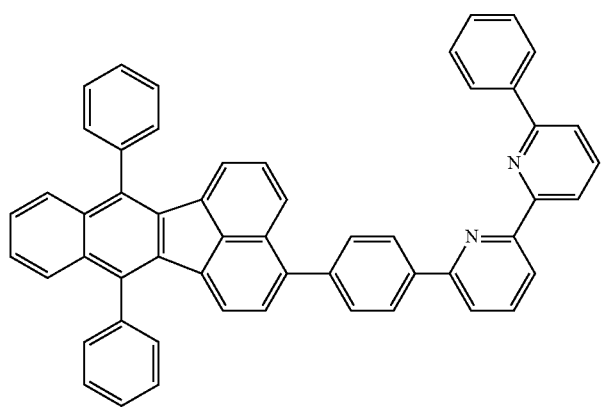

-continued
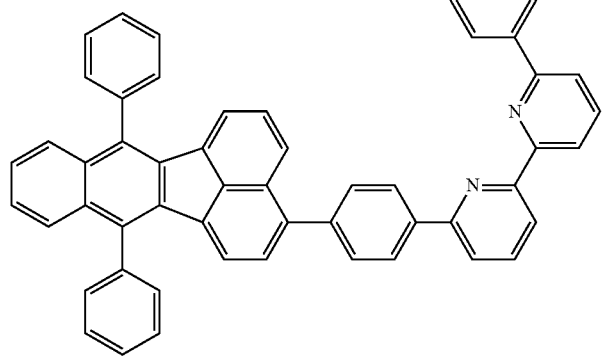
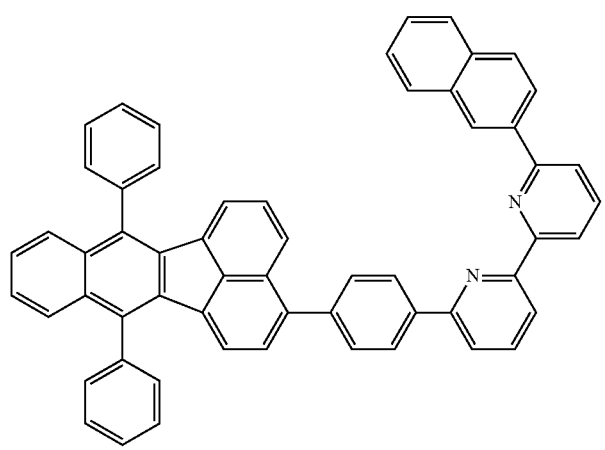
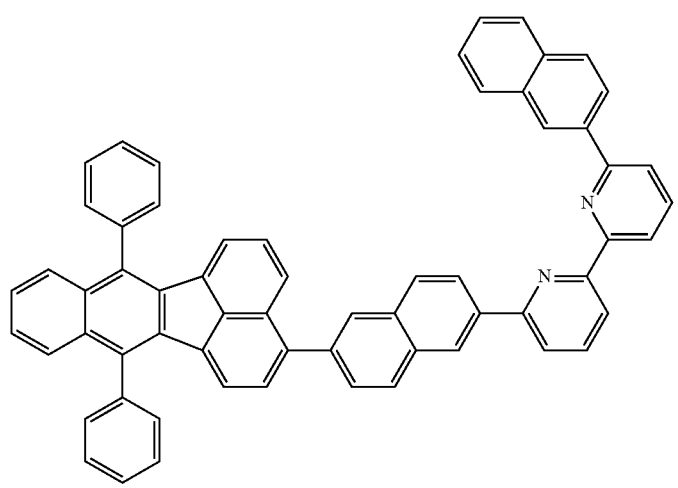

-continued
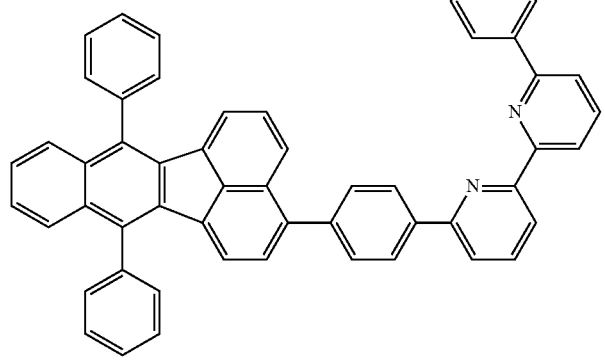
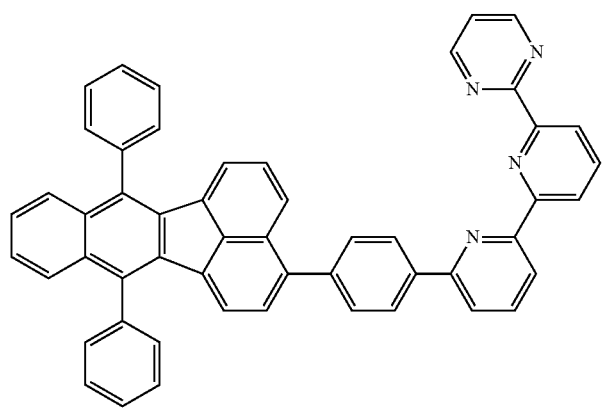
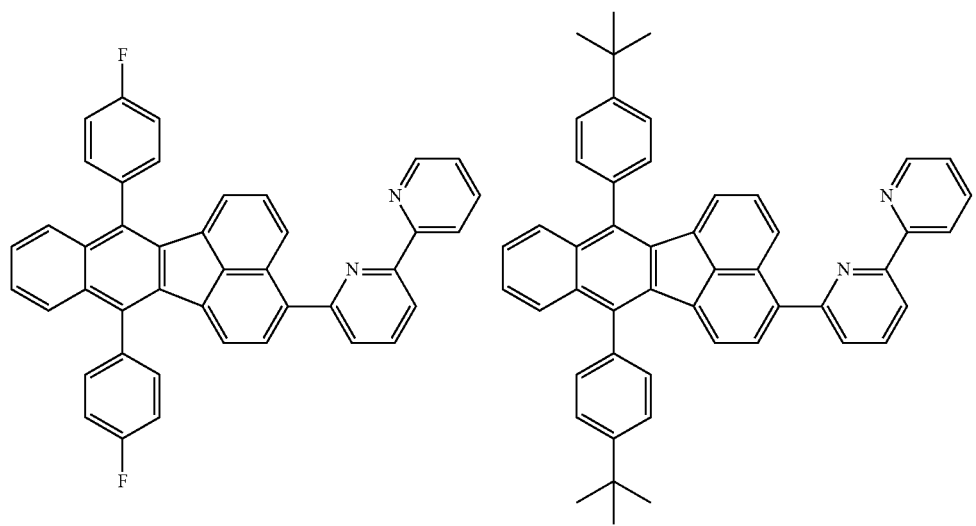

-continued
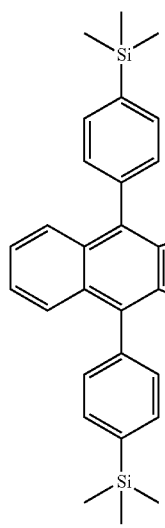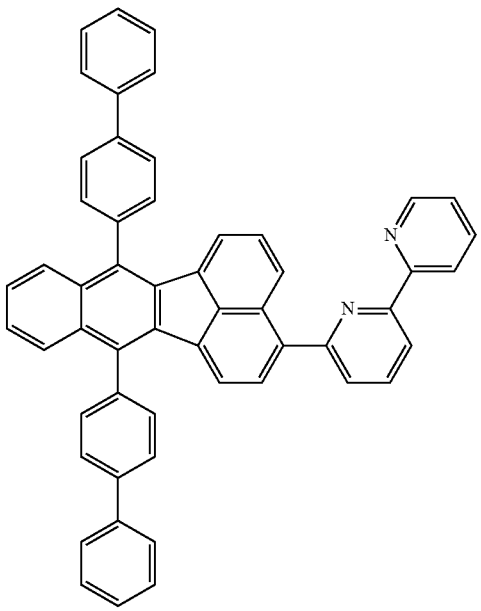
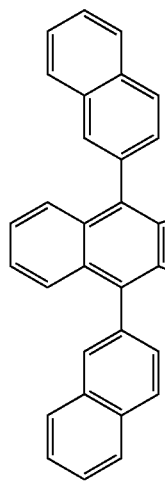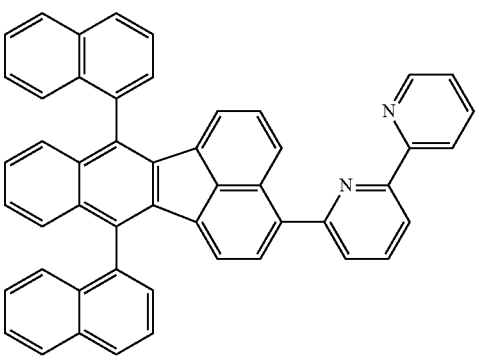
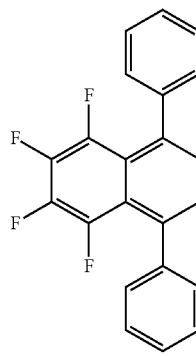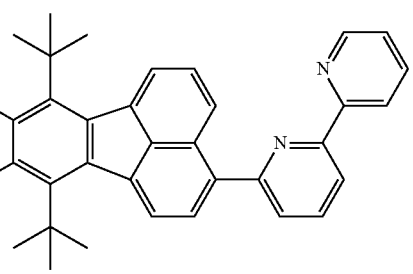

-continued
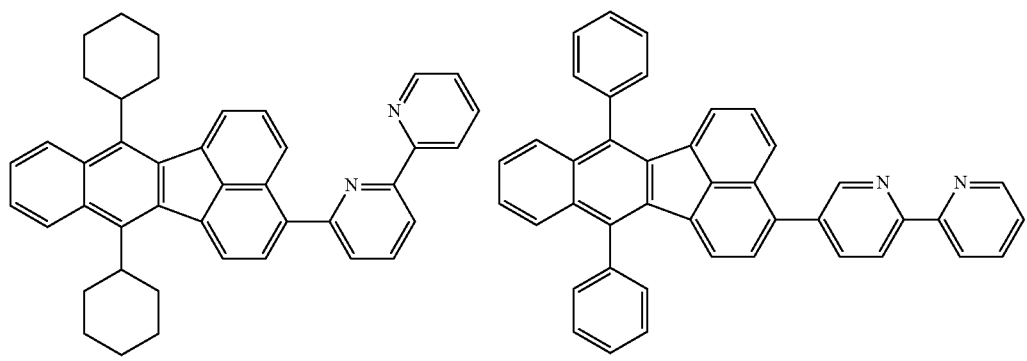
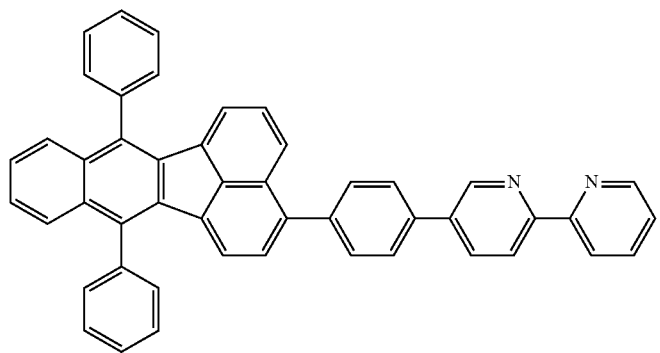
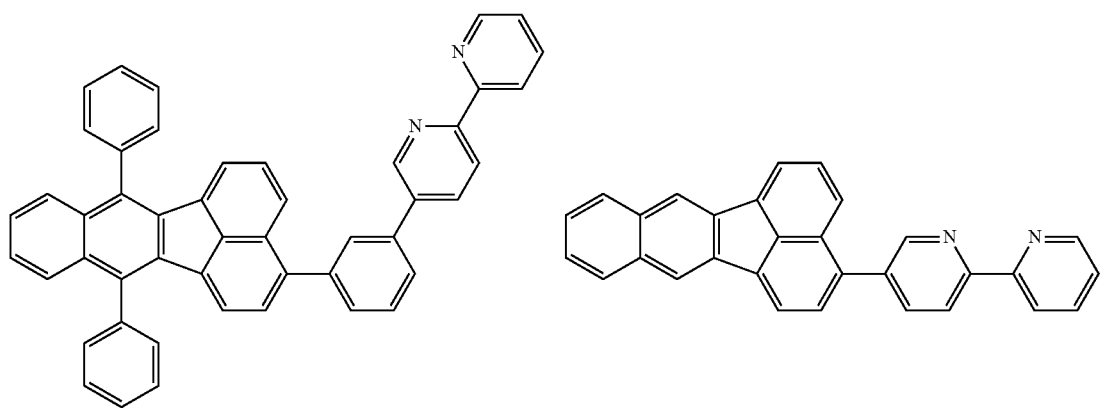
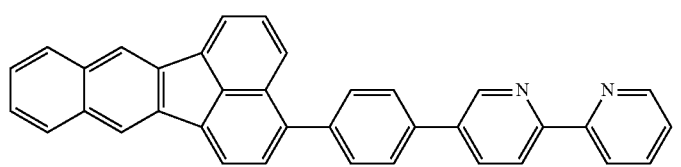

-continued
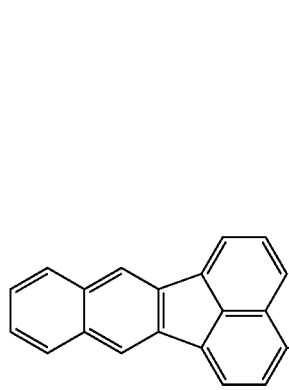
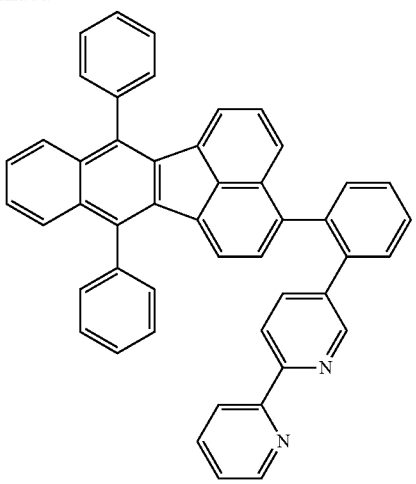
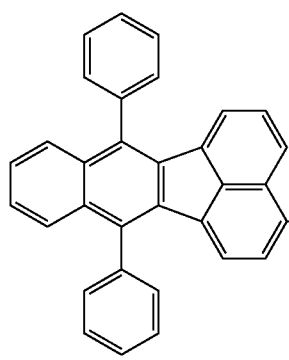
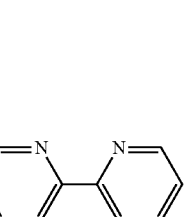
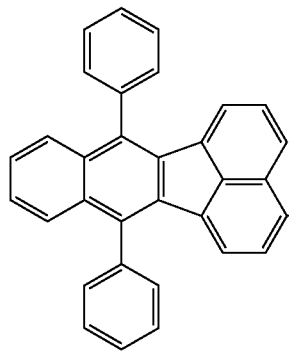
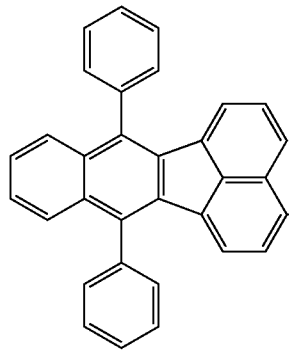
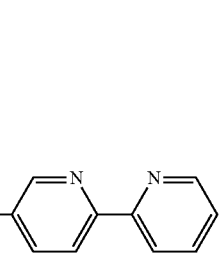

-continued
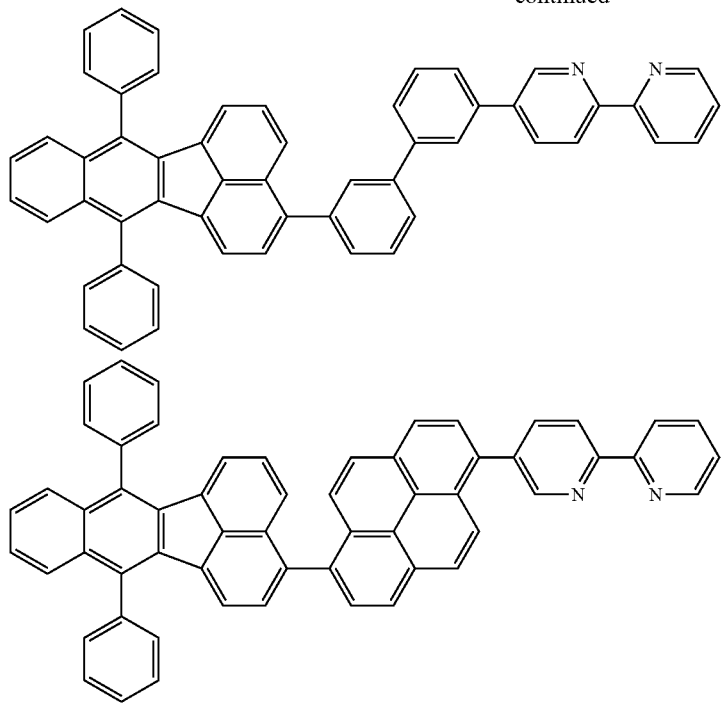
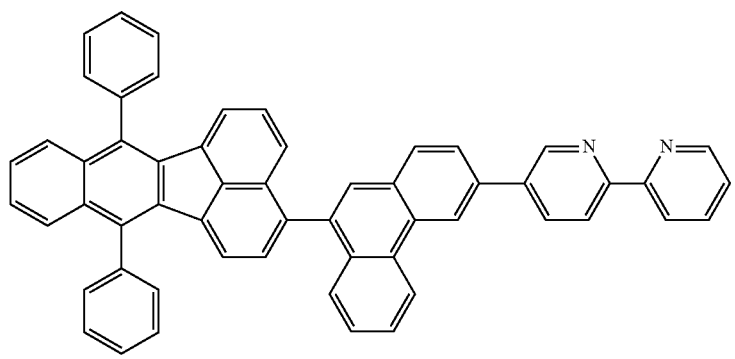
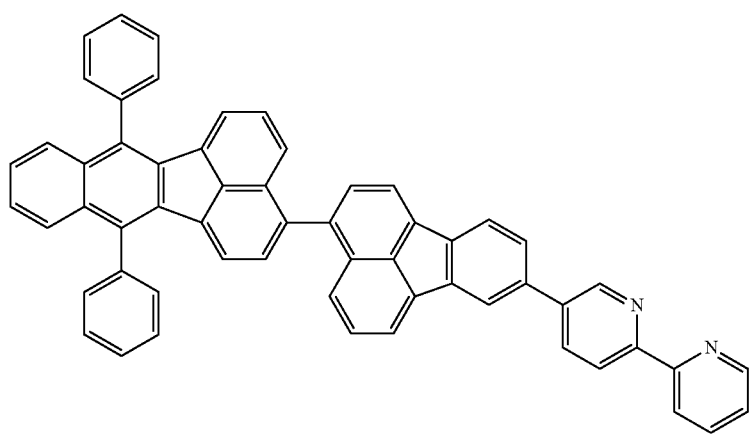

-continued
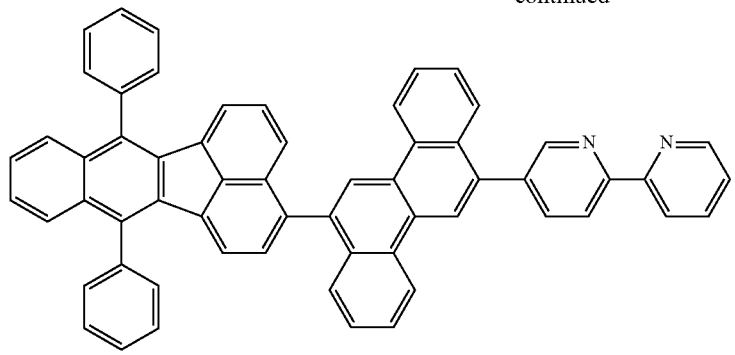
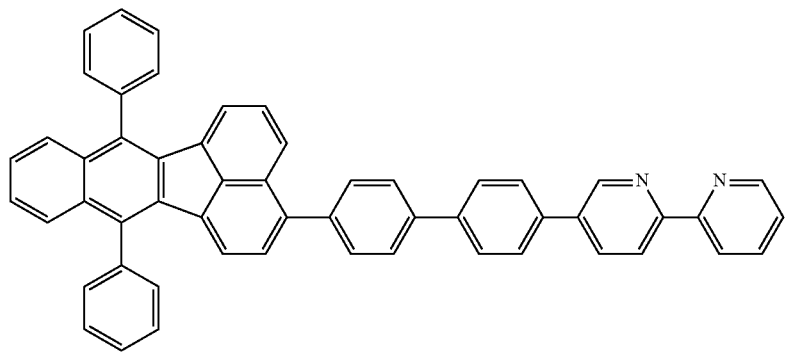
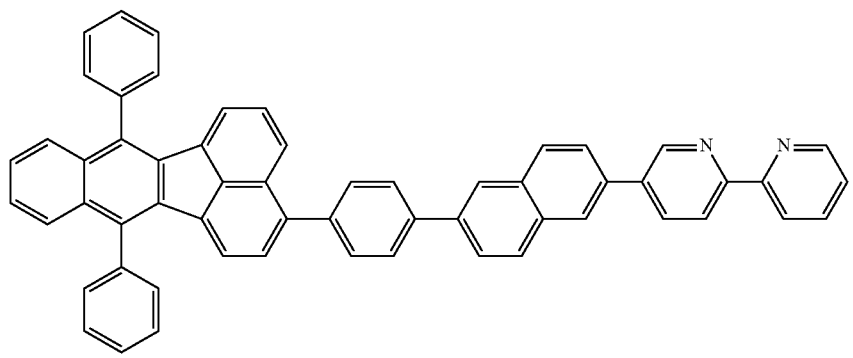
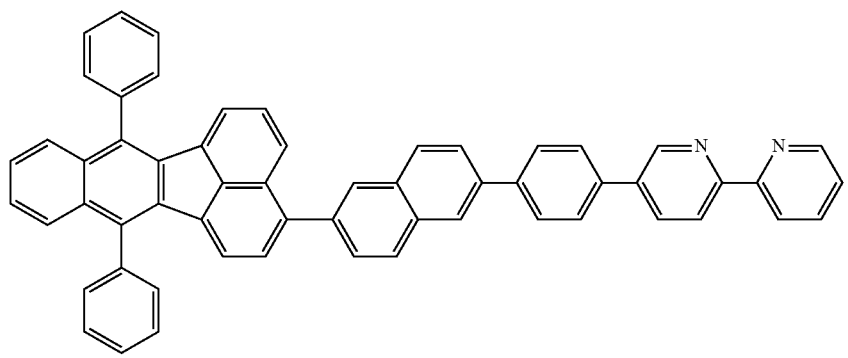

-continued
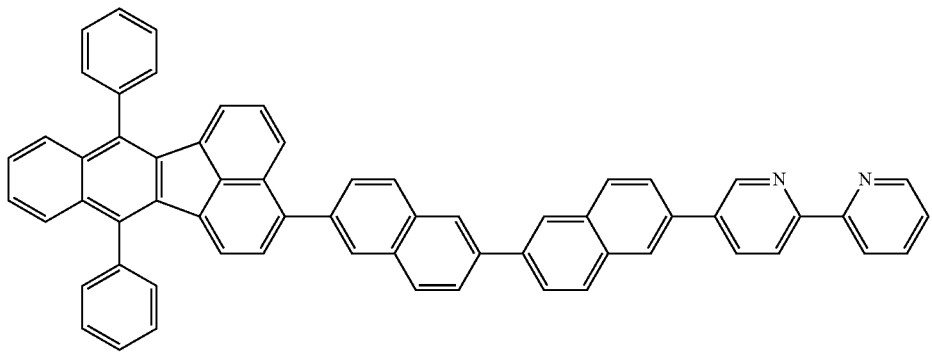
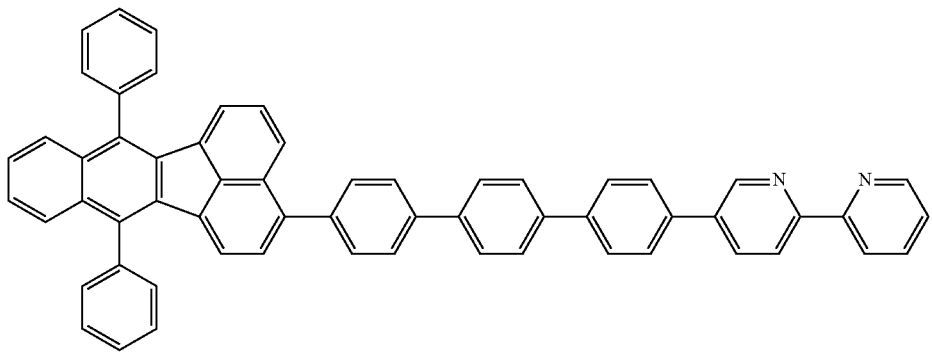
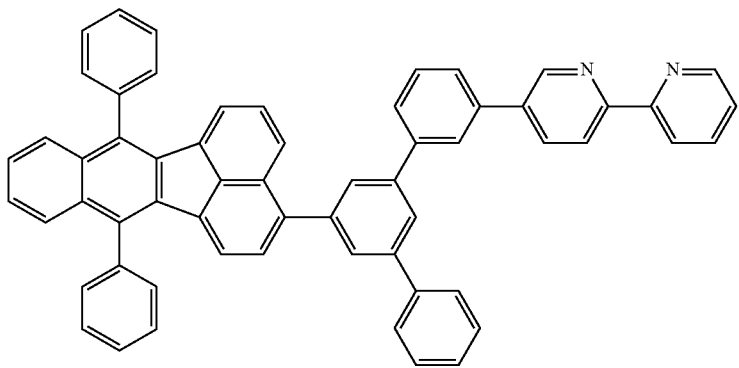
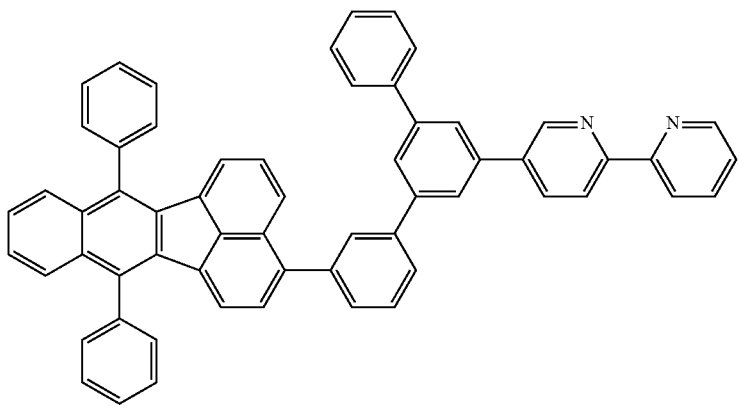

-continued
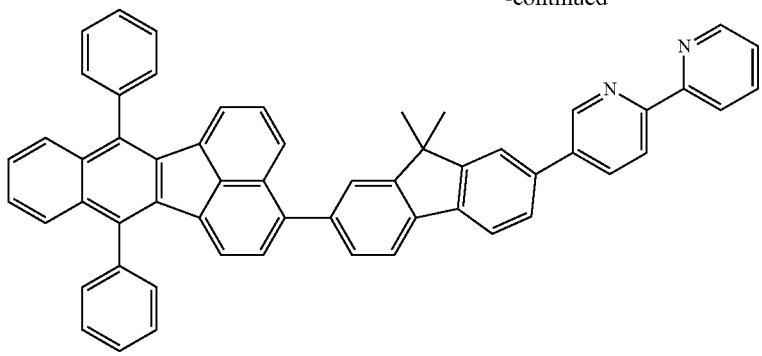
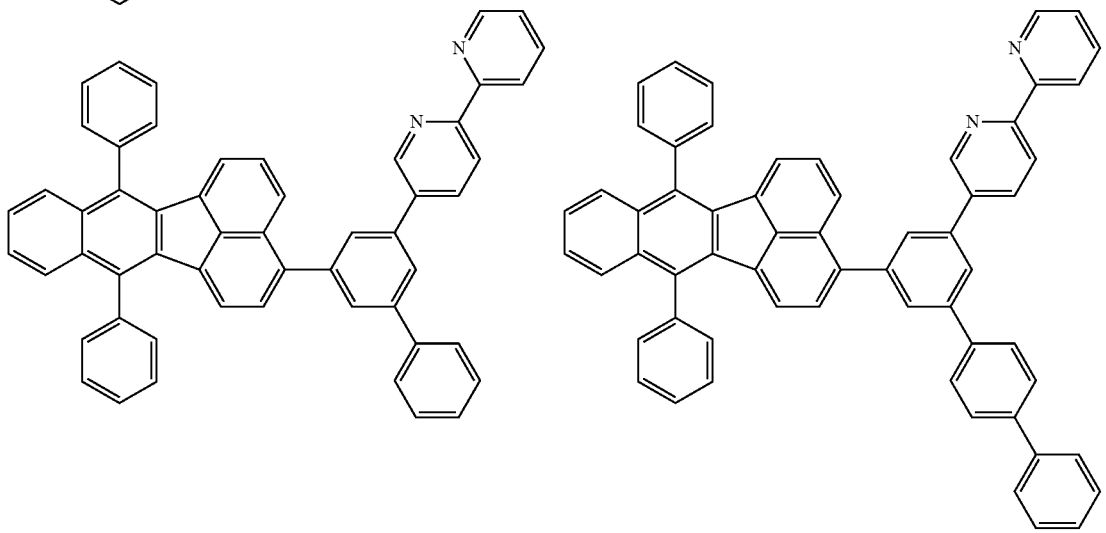
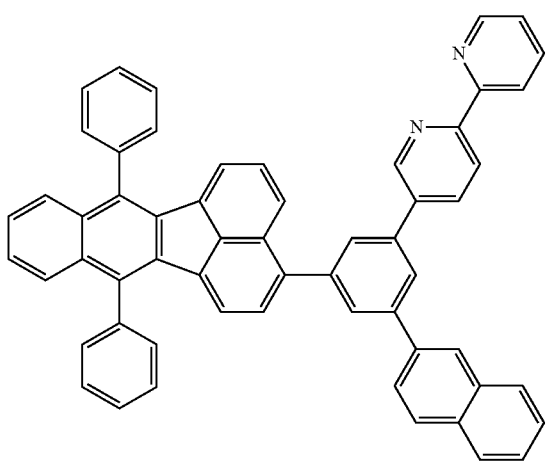
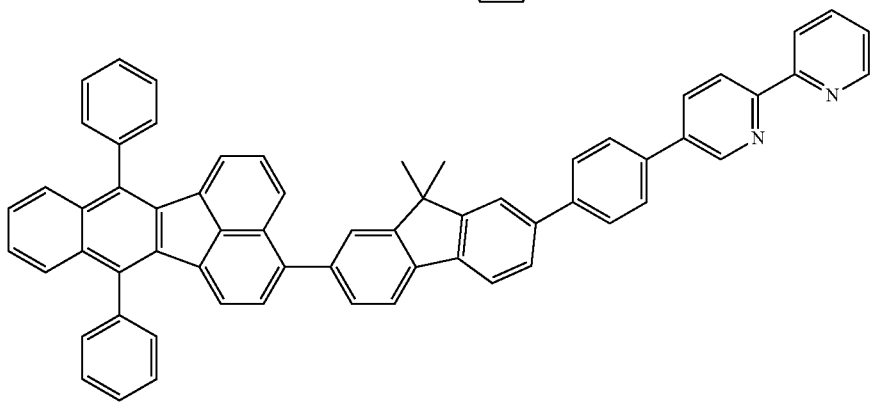

-continued
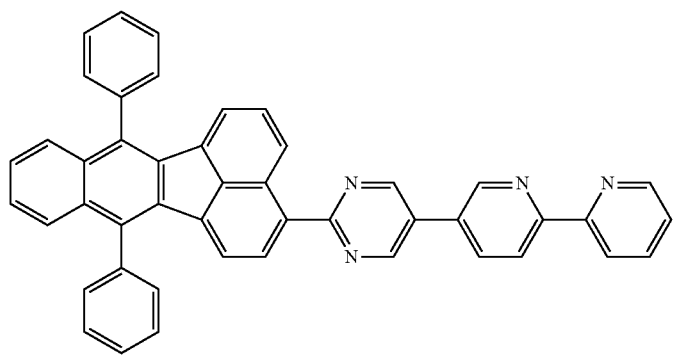
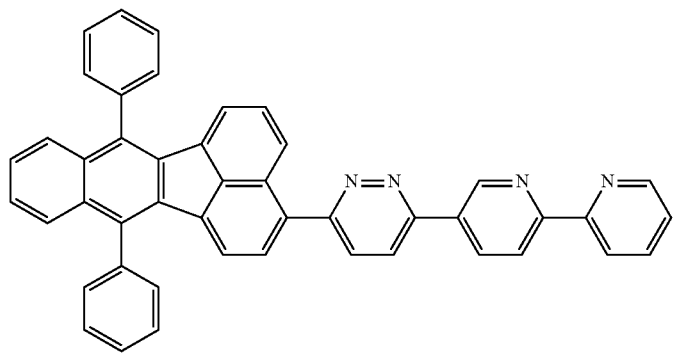
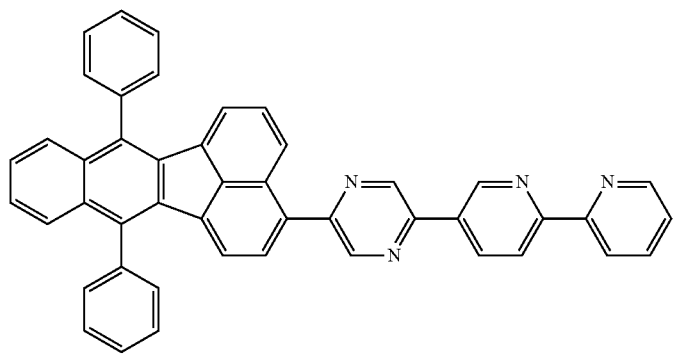
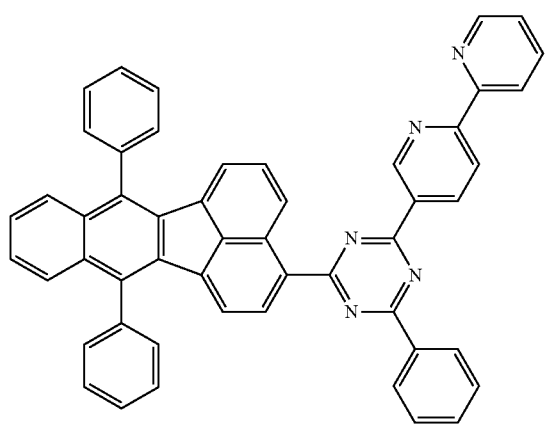

-continued
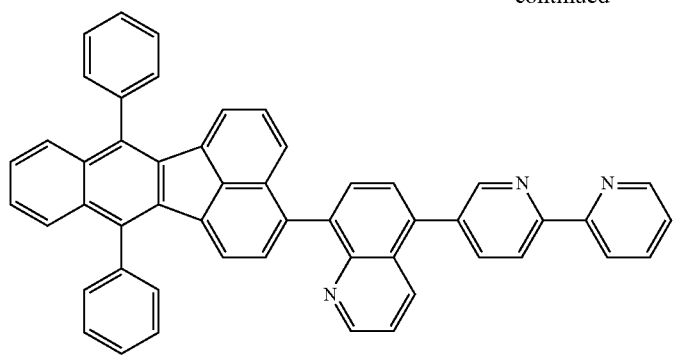
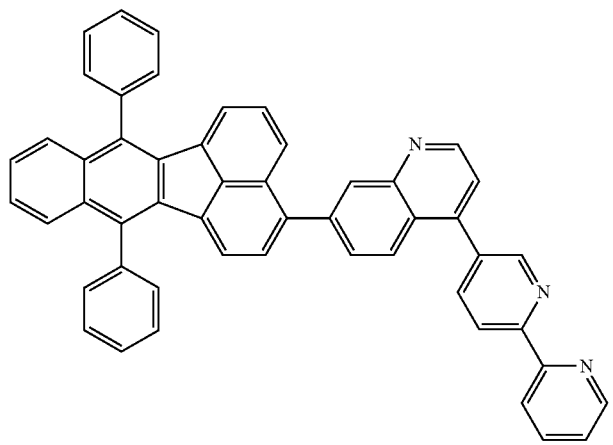
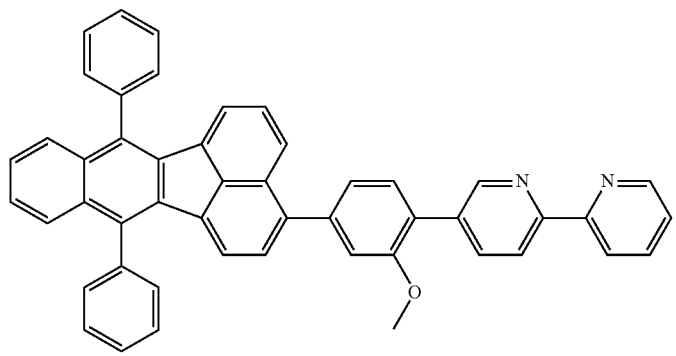
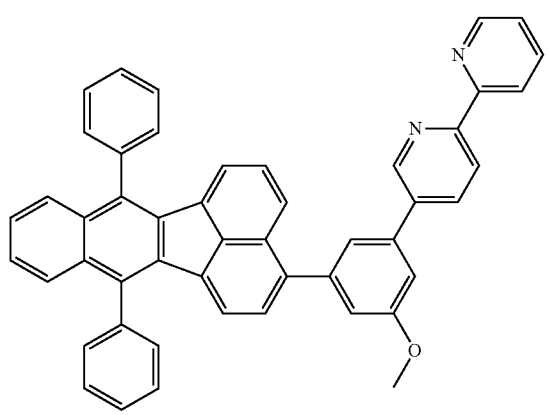

-continued
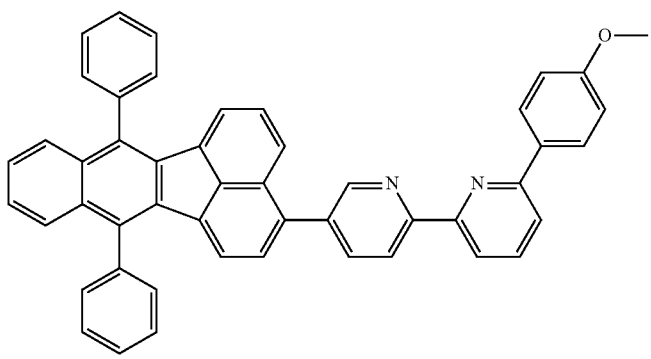
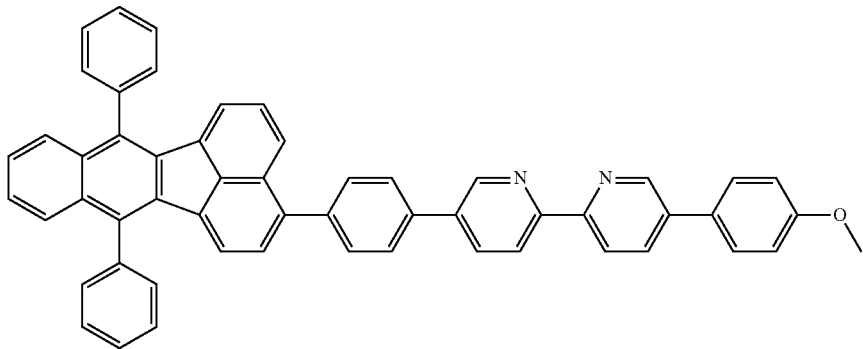
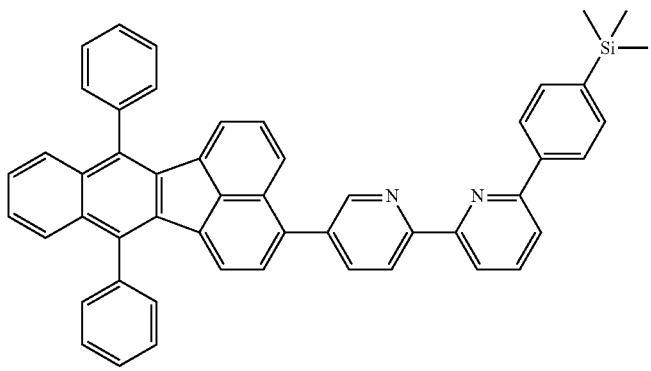
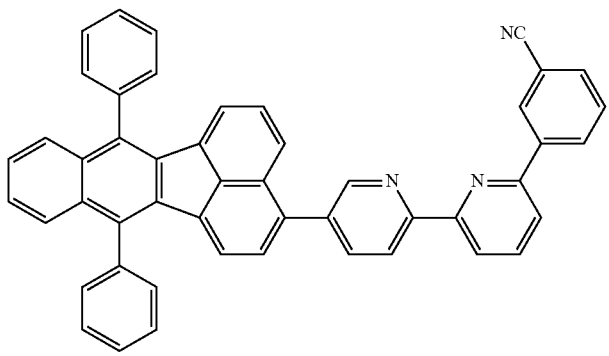

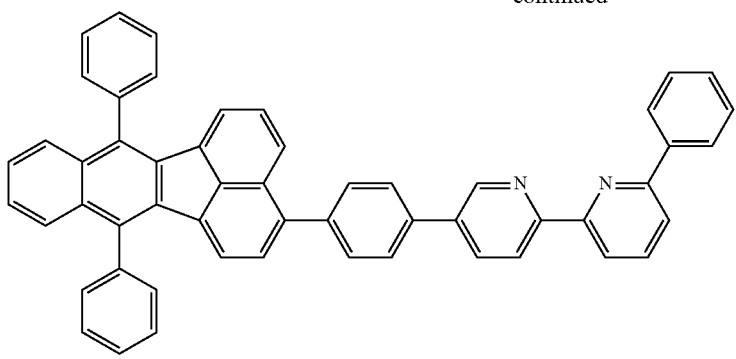

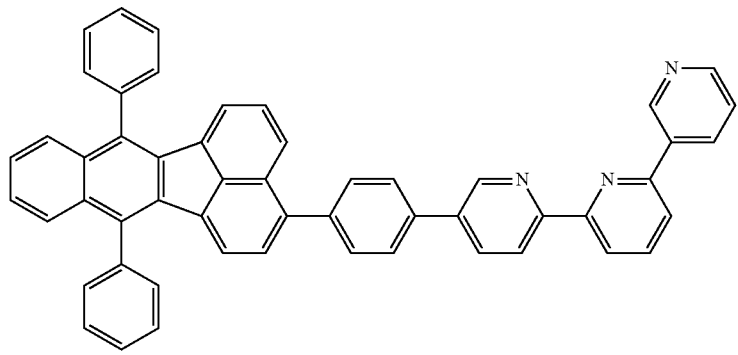
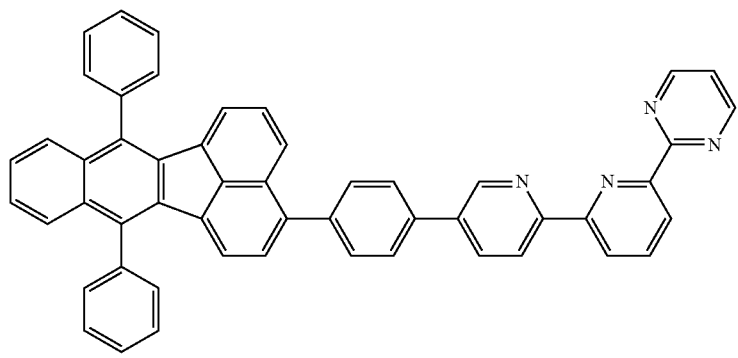
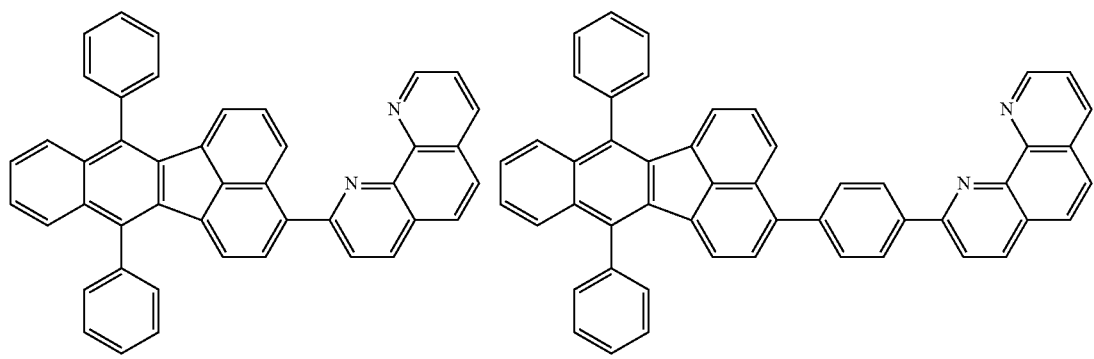
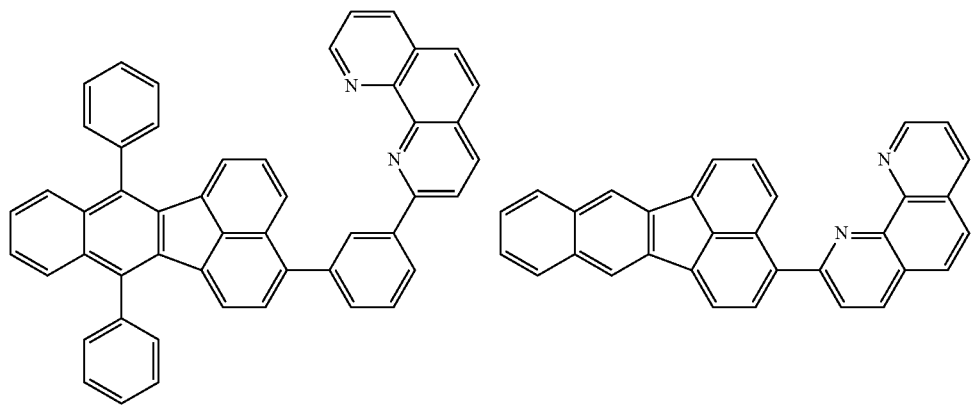

-continued
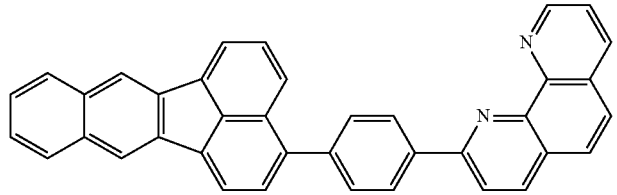
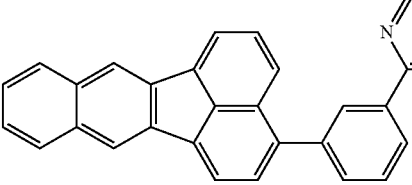
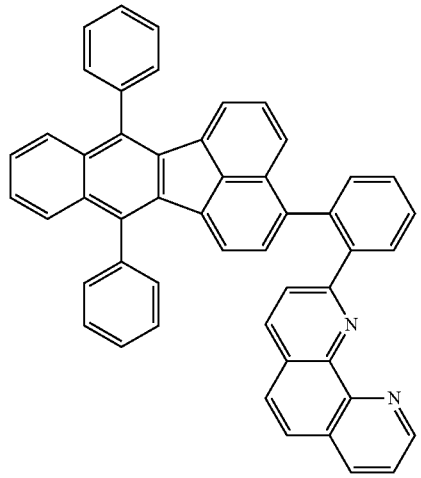
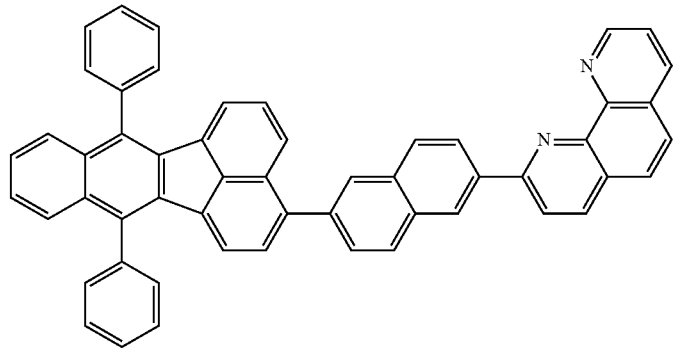
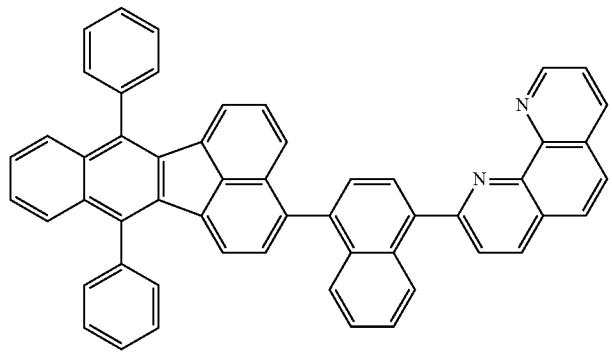
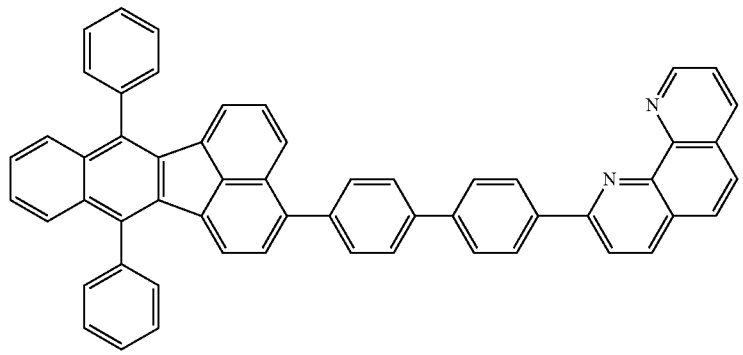

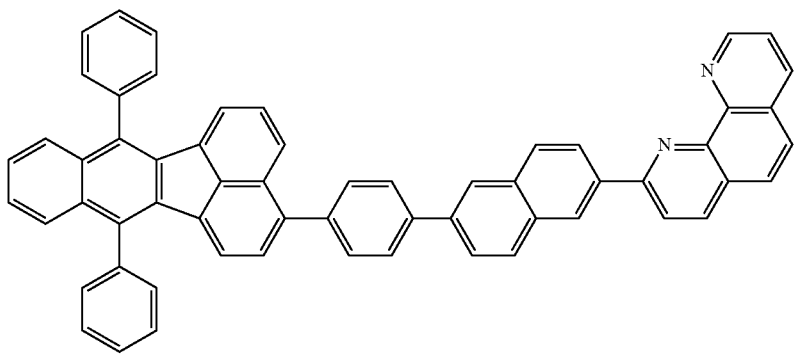
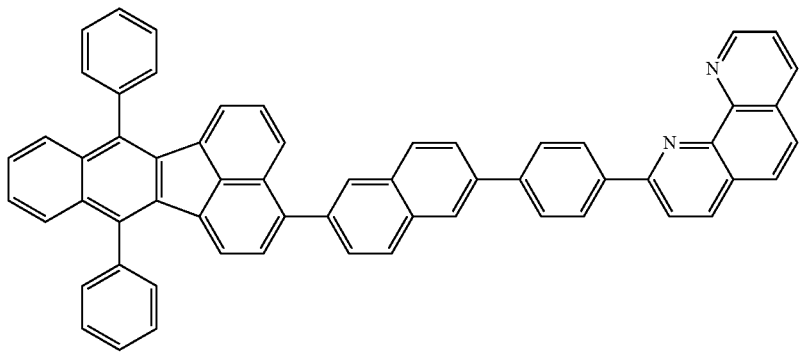
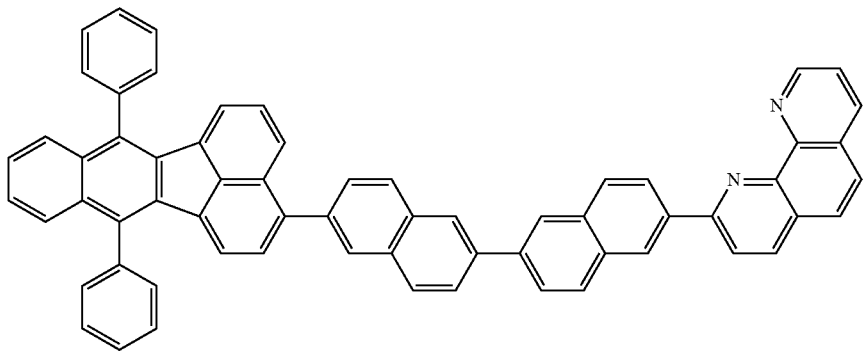
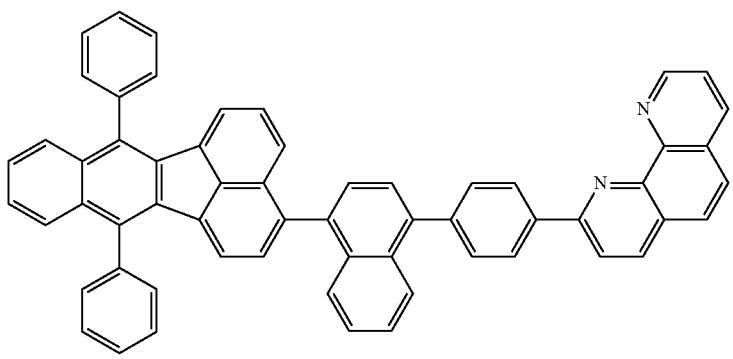

-continued
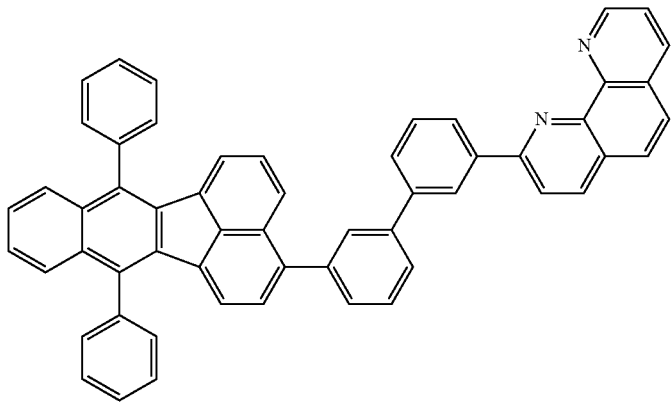
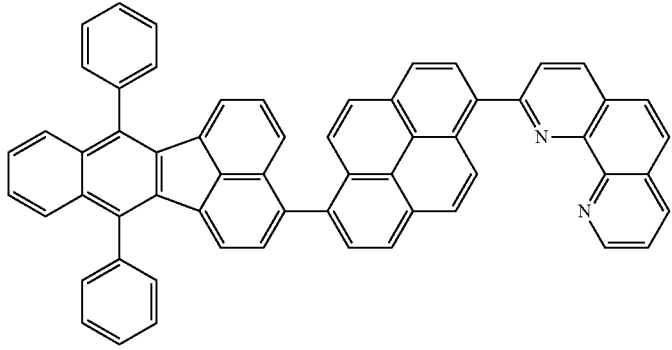
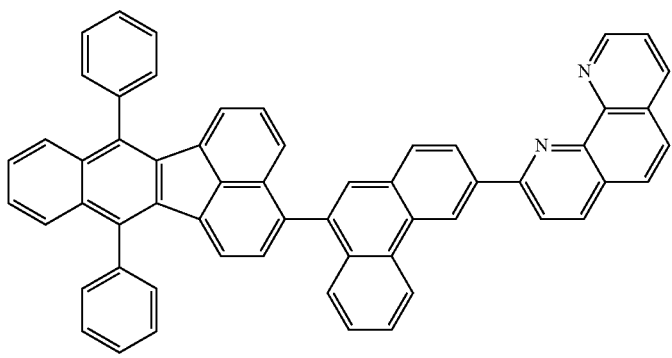
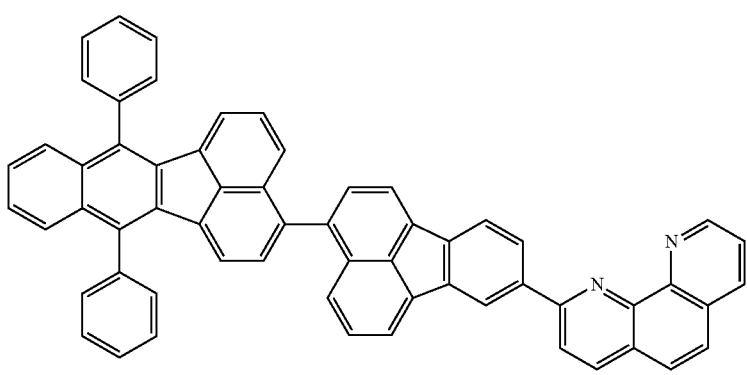

-continued
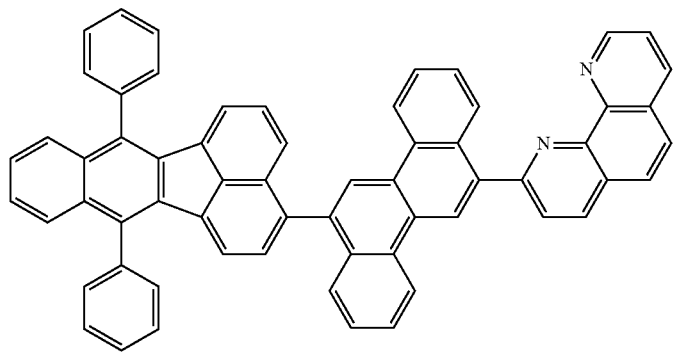
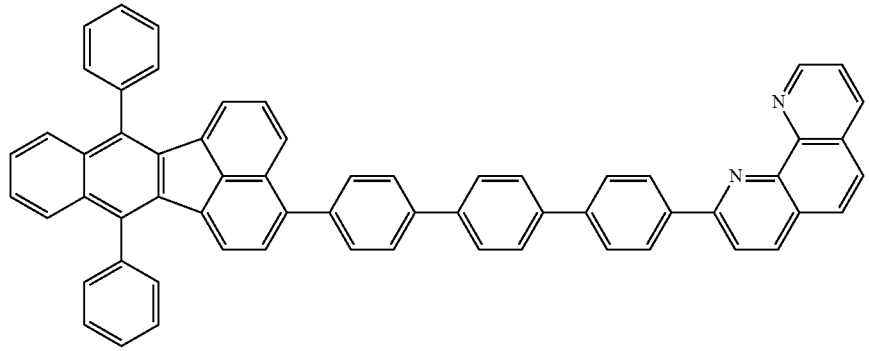
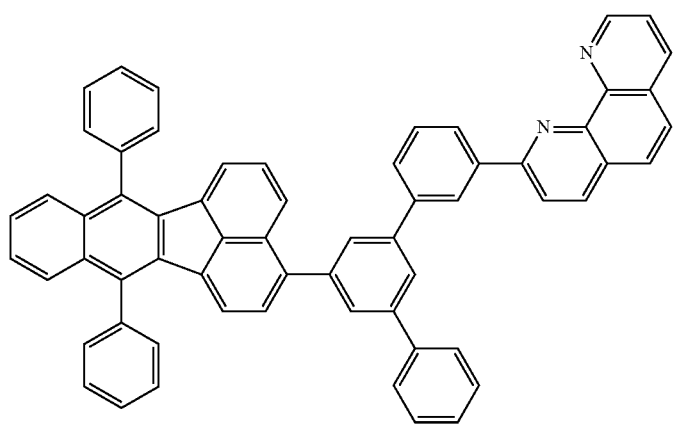
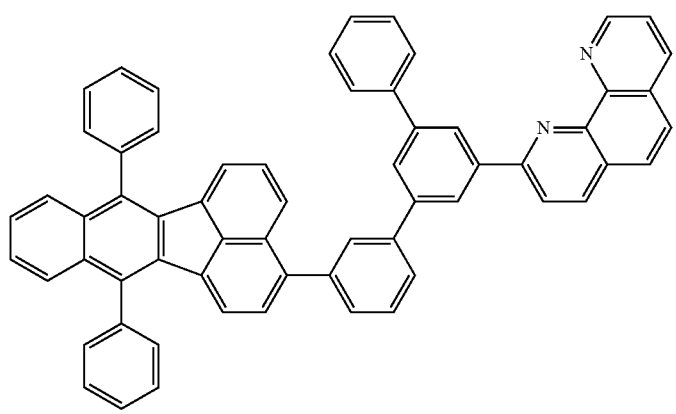

-continued
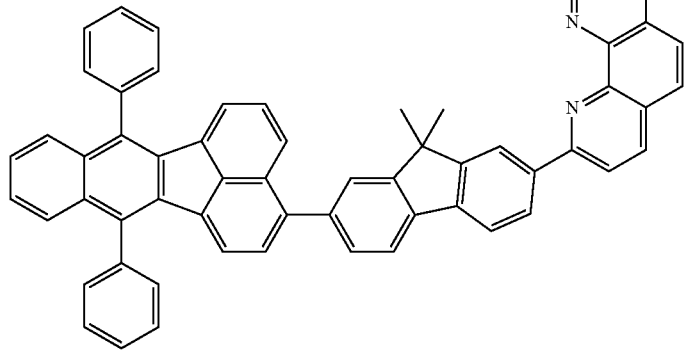
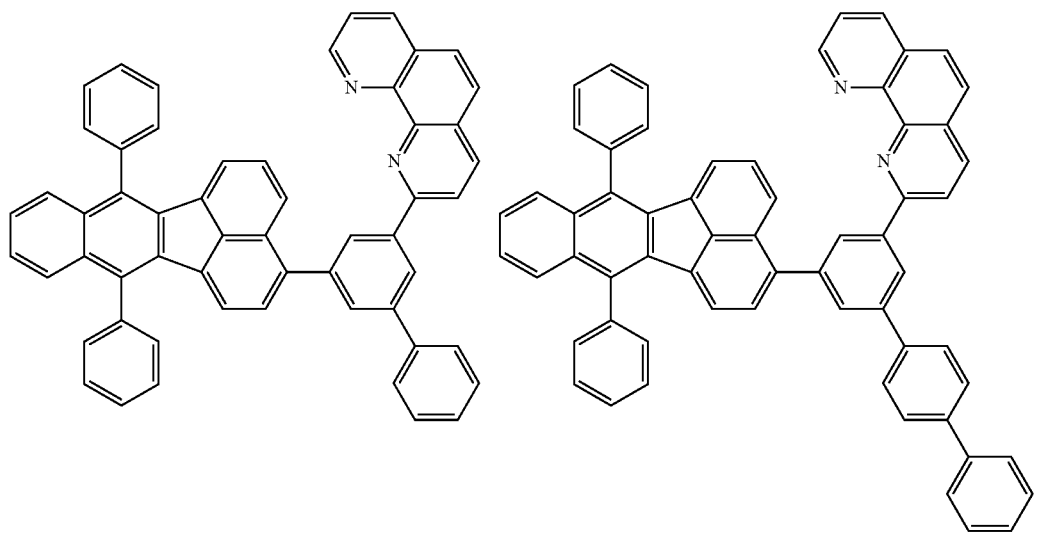
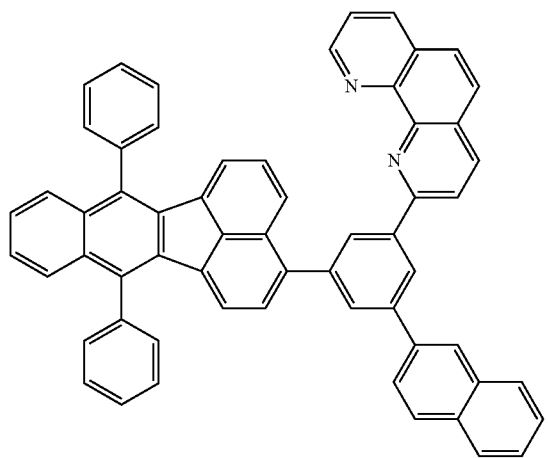

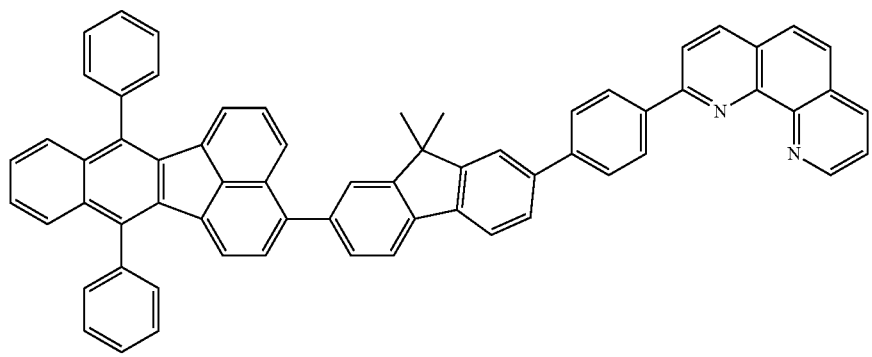
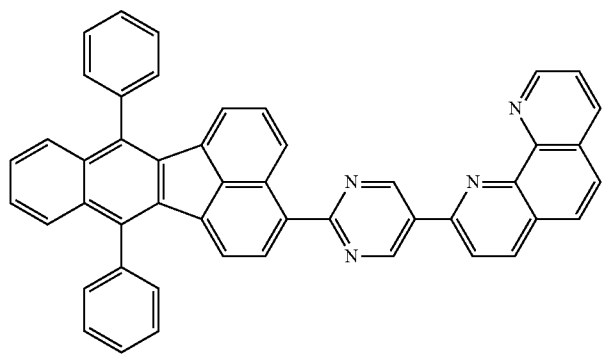
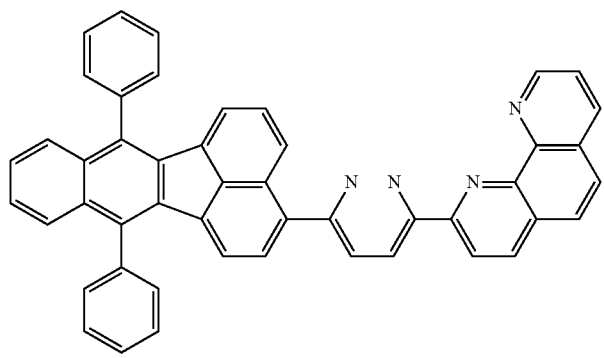
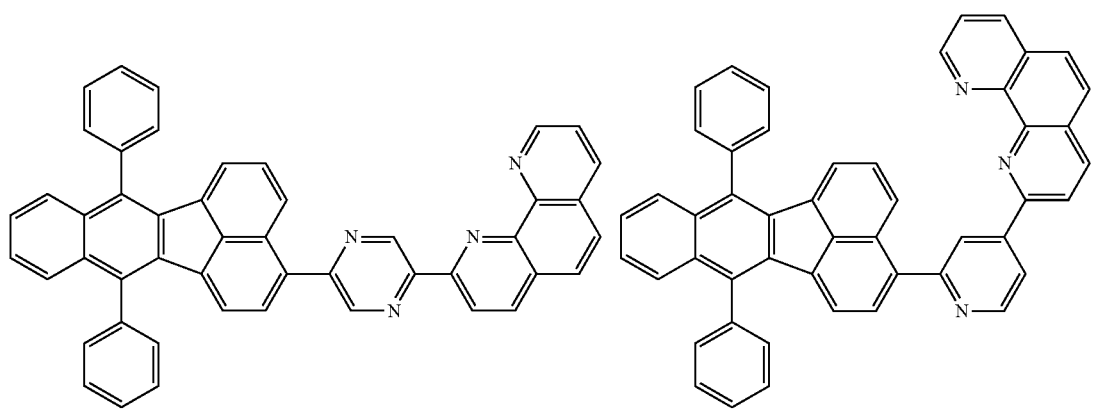

81
-continued
82
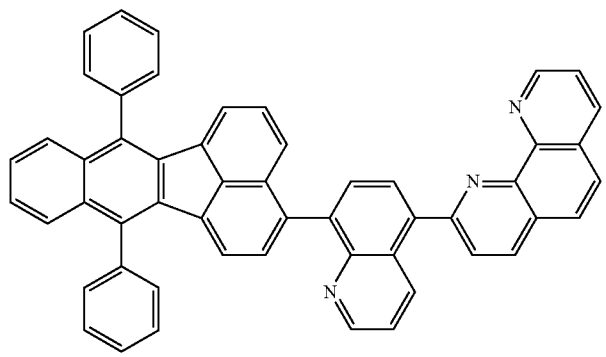
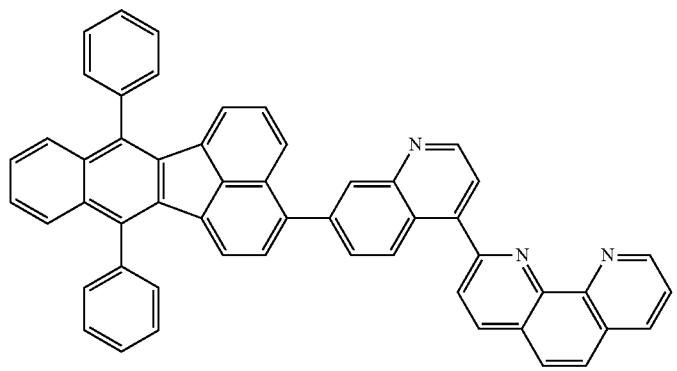
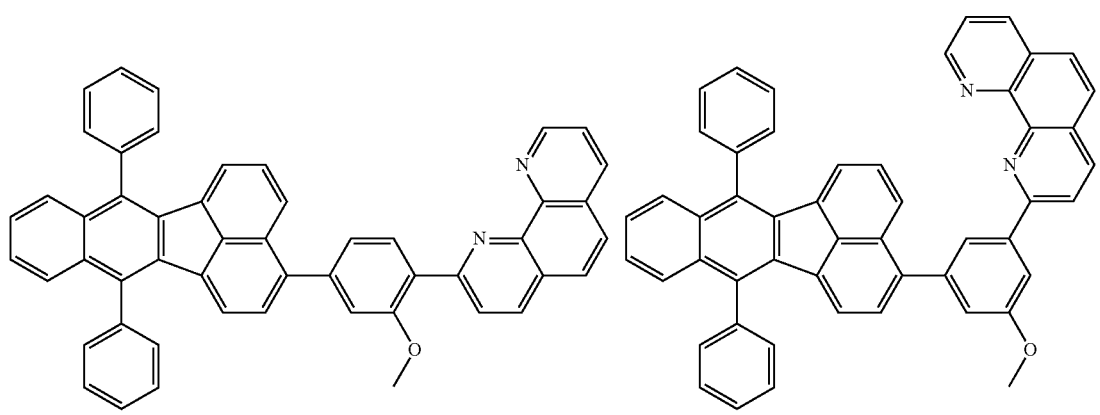
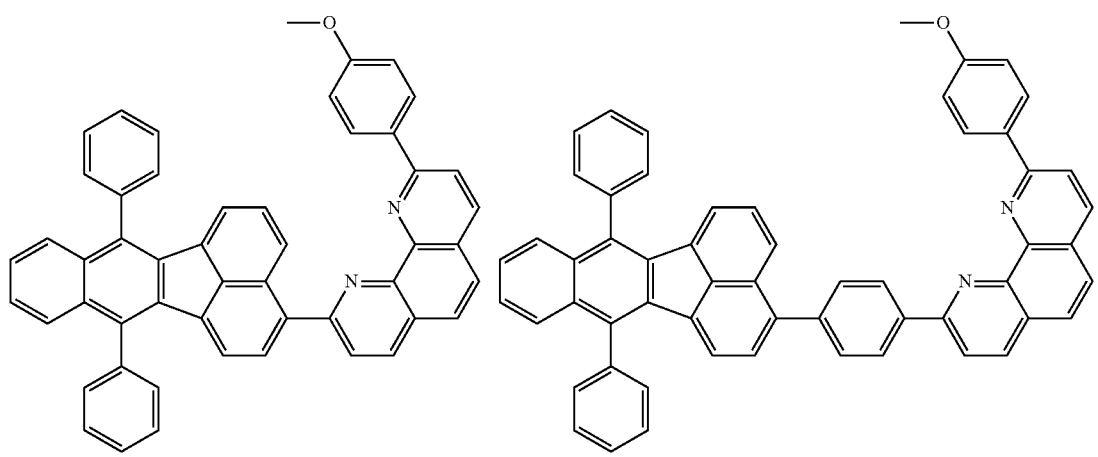

-continued
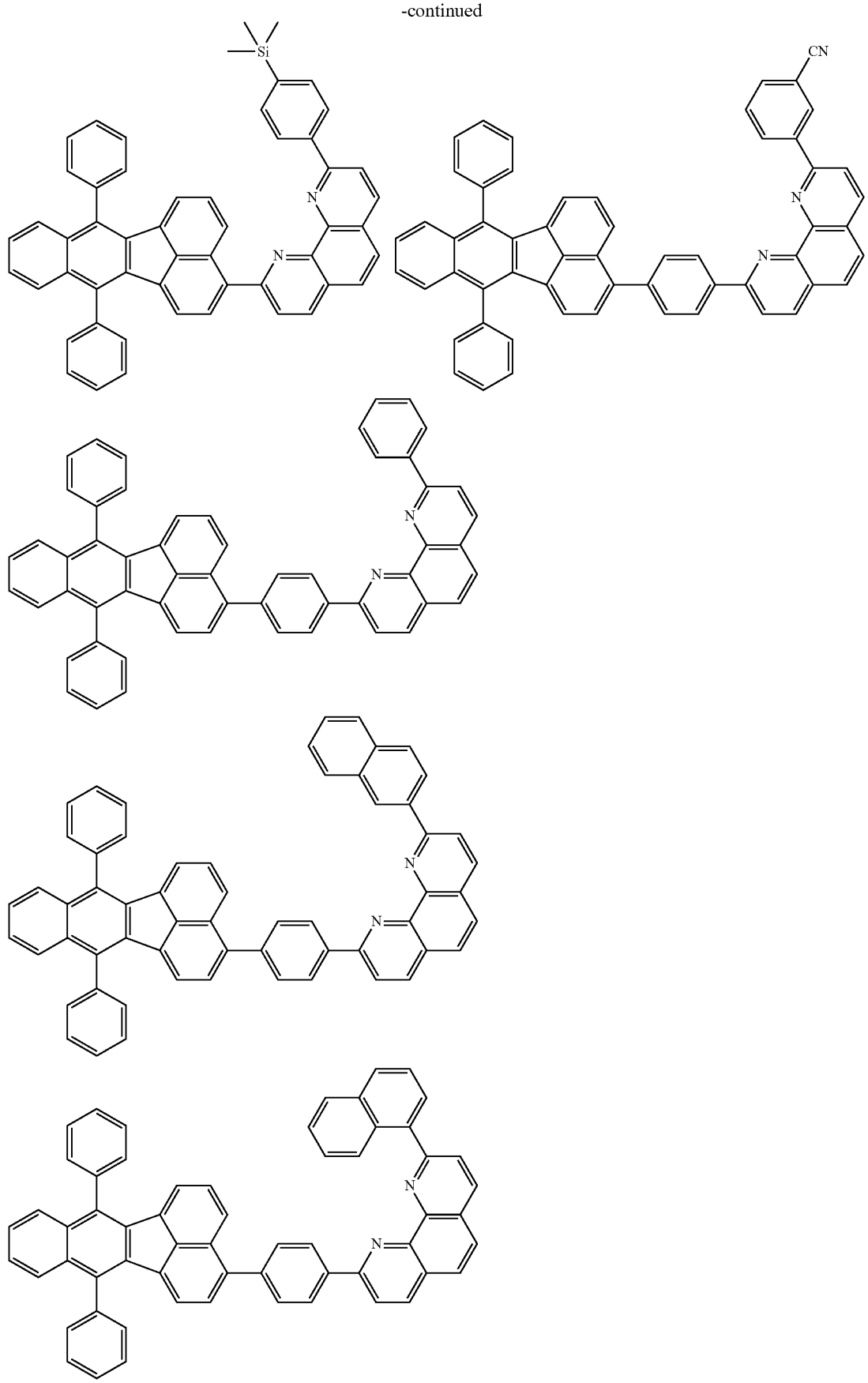

-continued
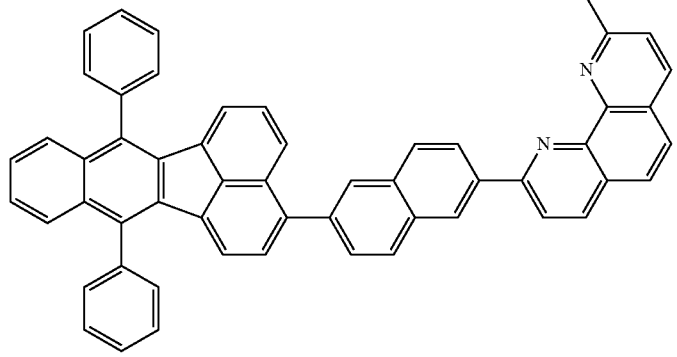
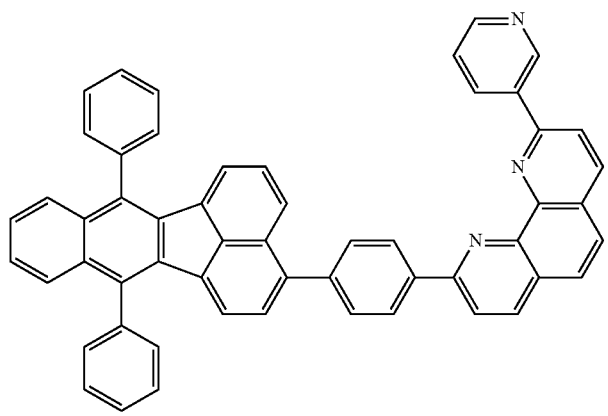
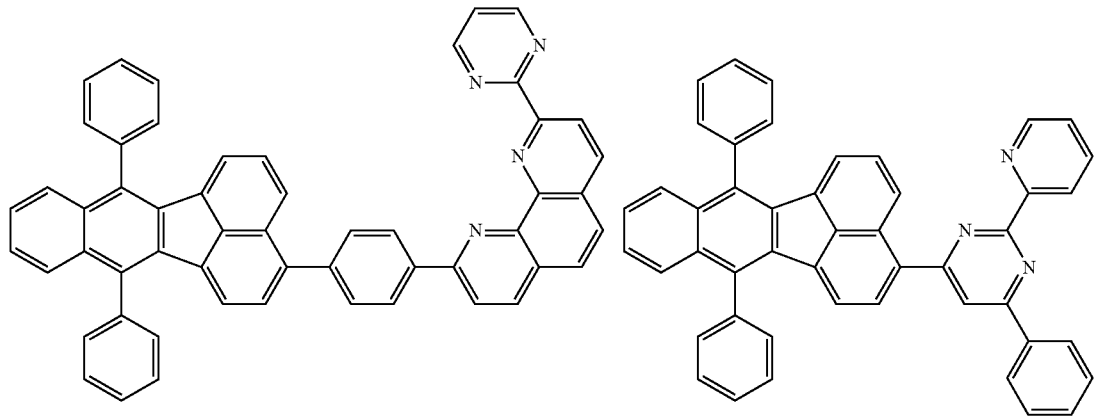
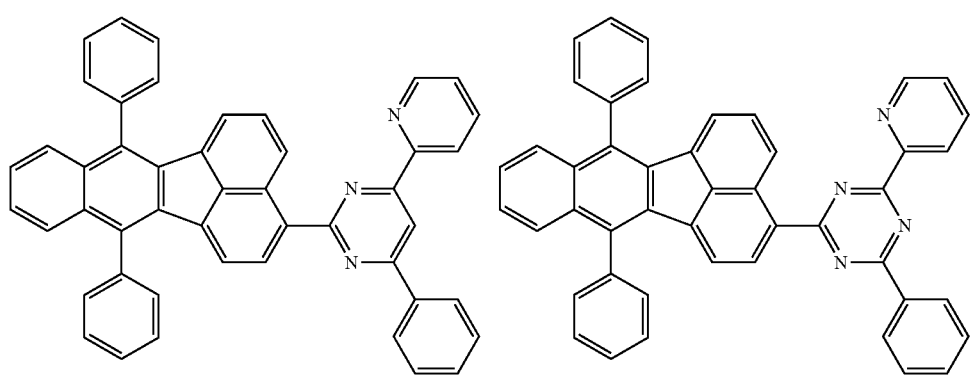

-continued
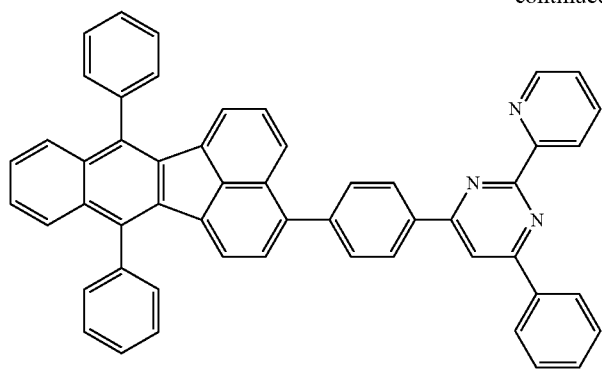
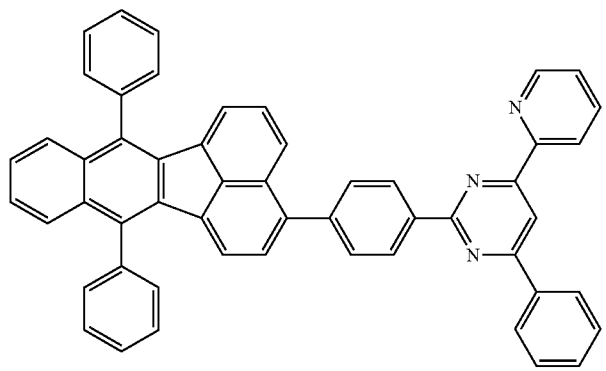
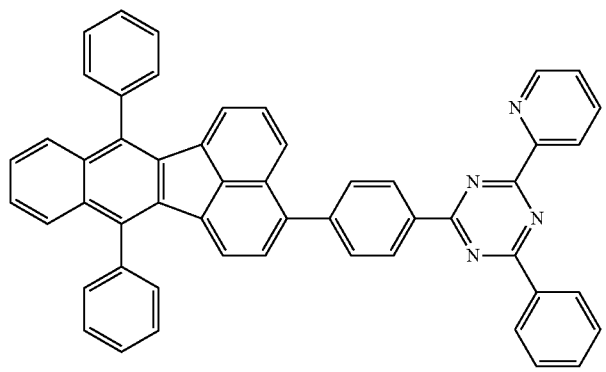
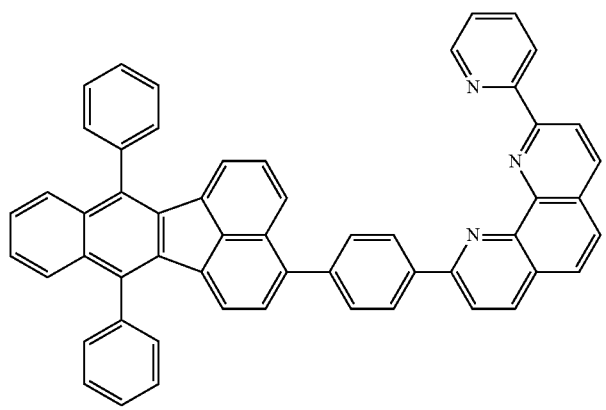

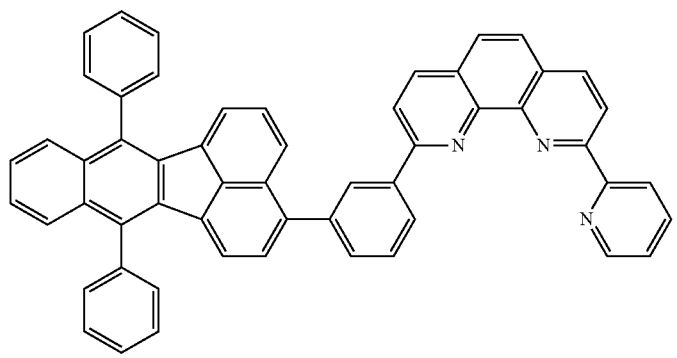
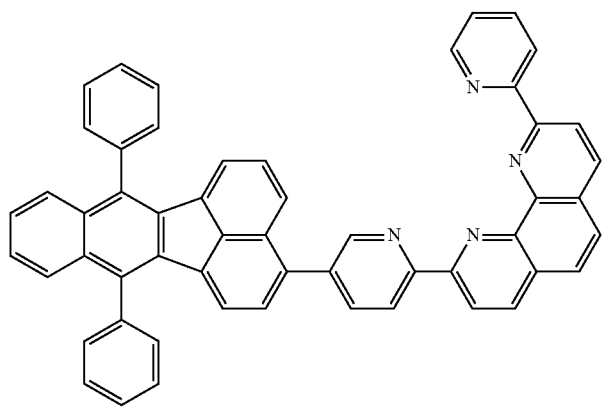
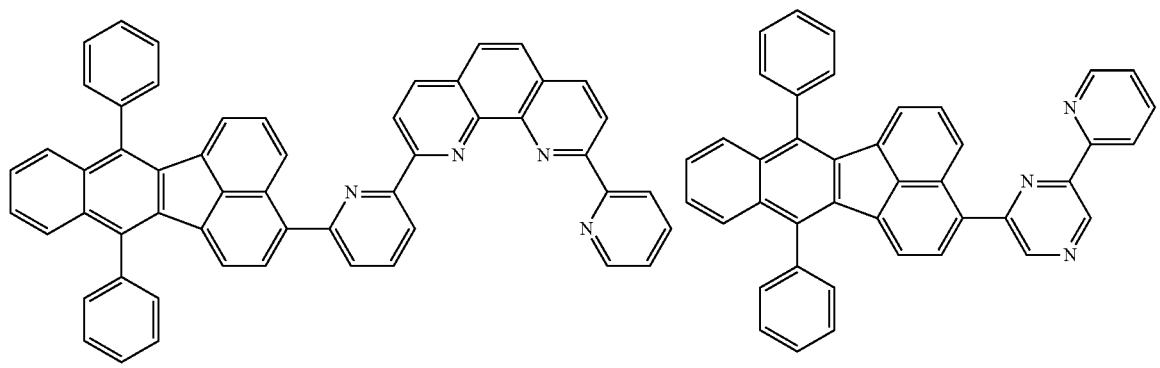
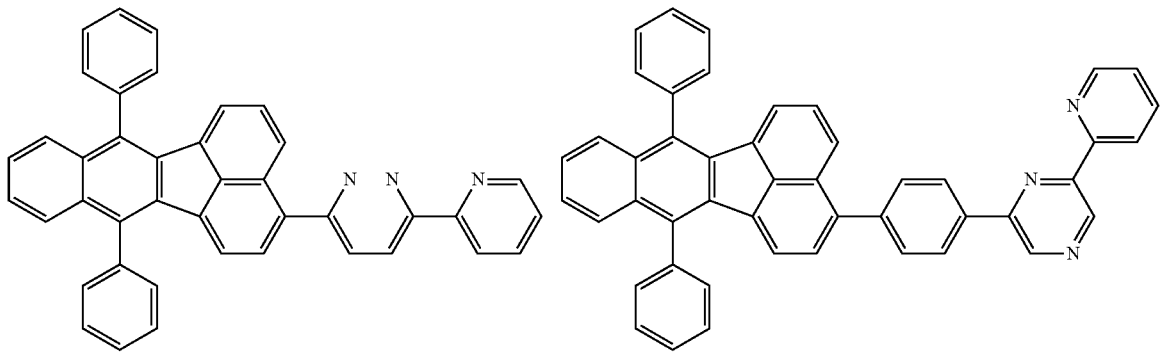

-continued
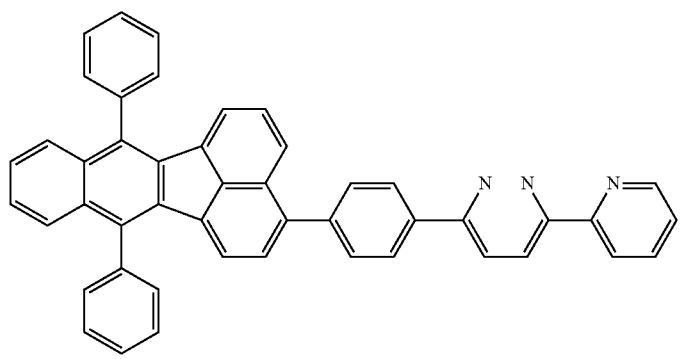
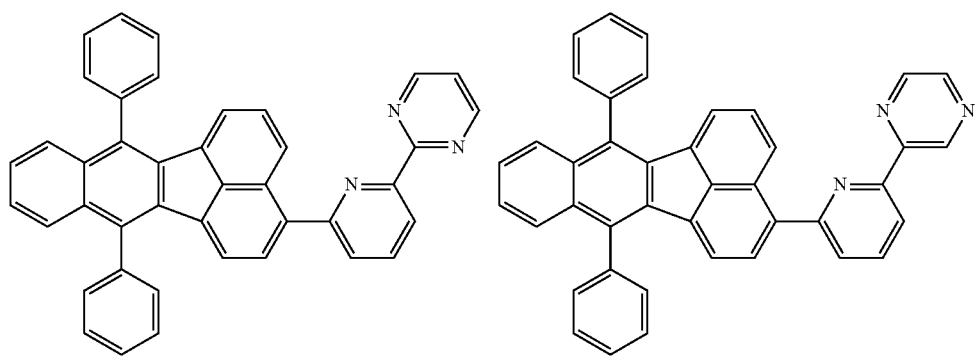
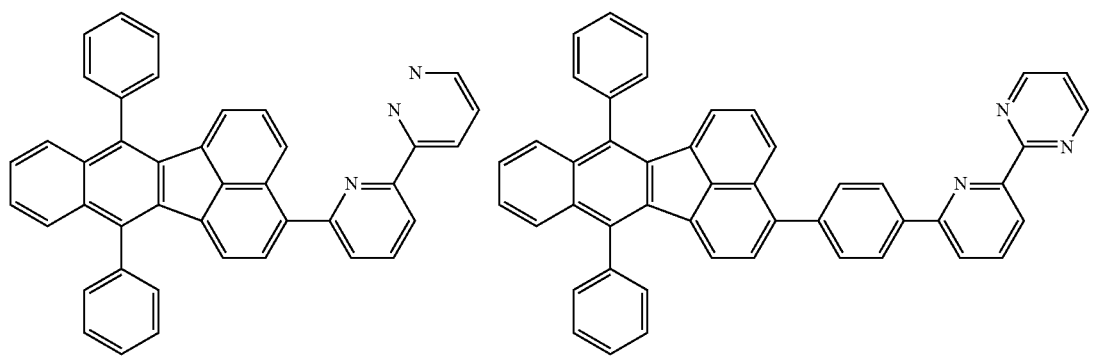
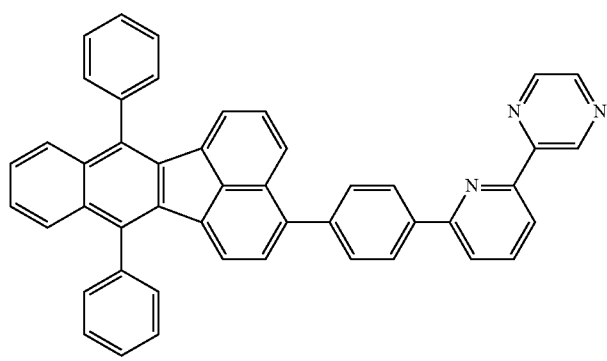

93 94
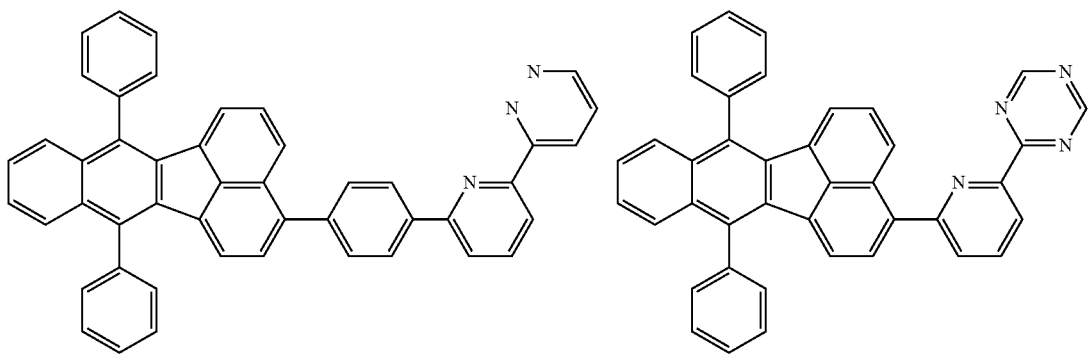
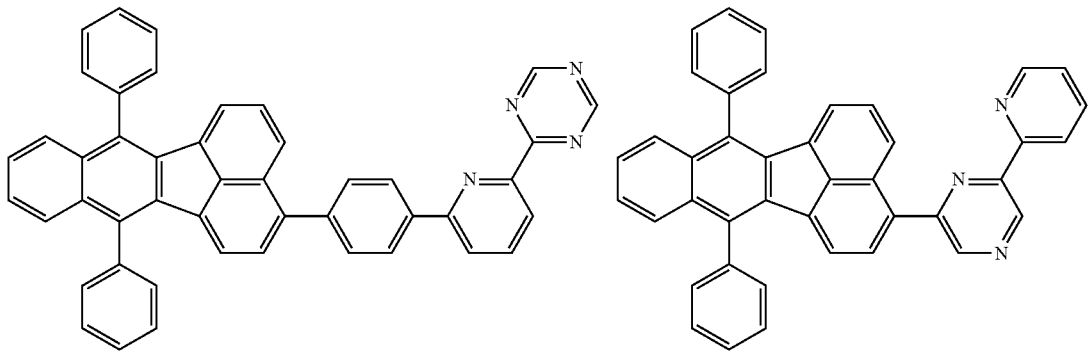
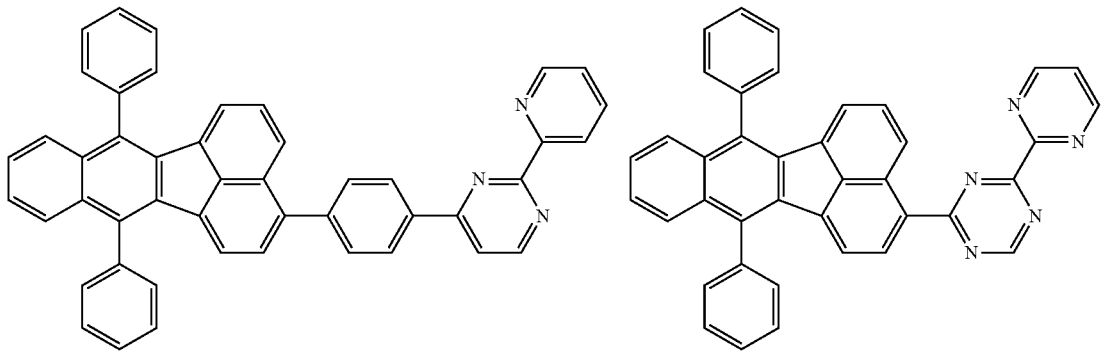
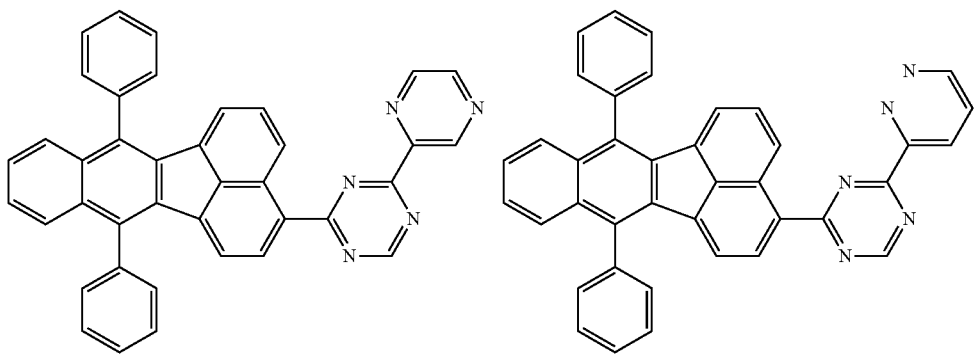

-continued
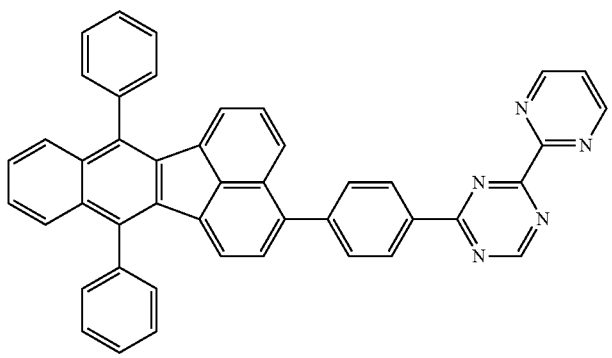
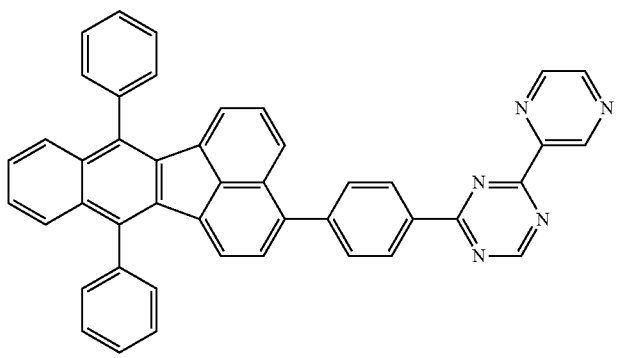
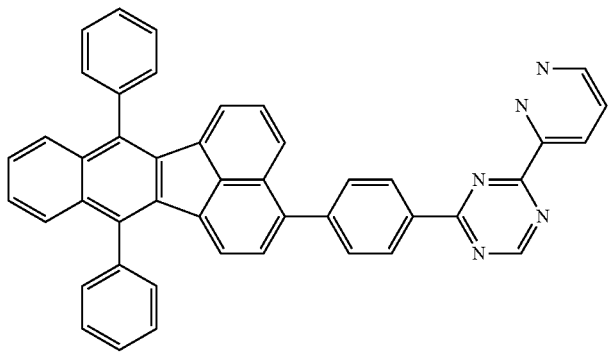
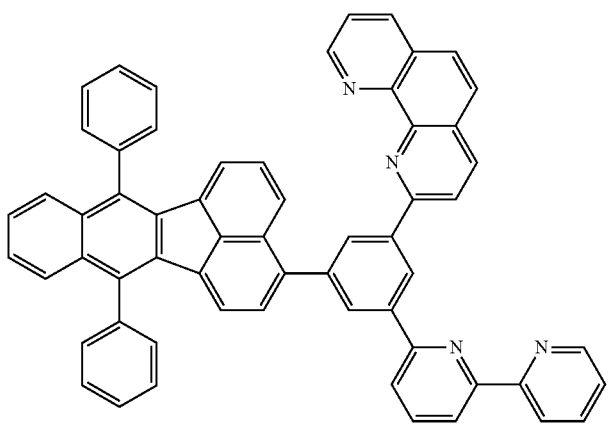

-continued
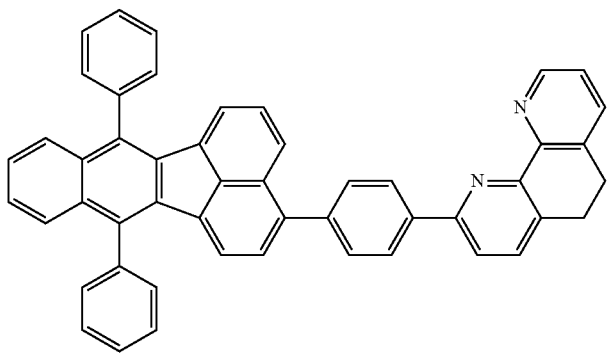
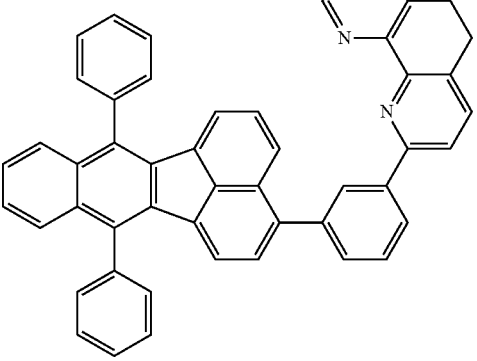
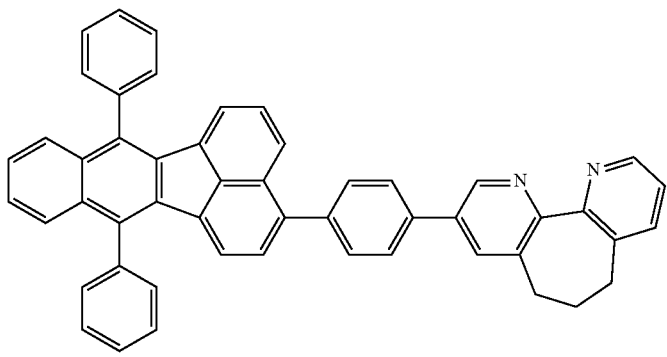
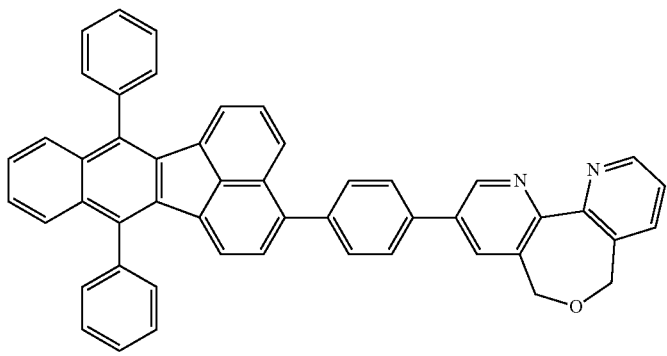
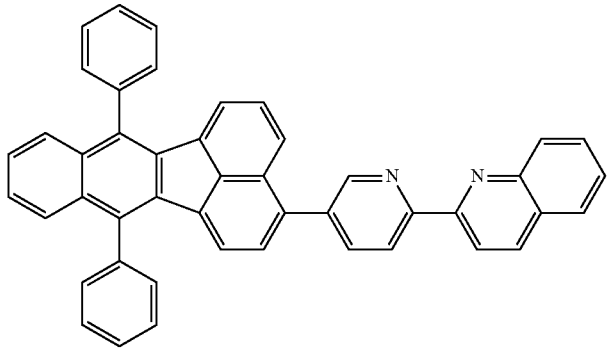

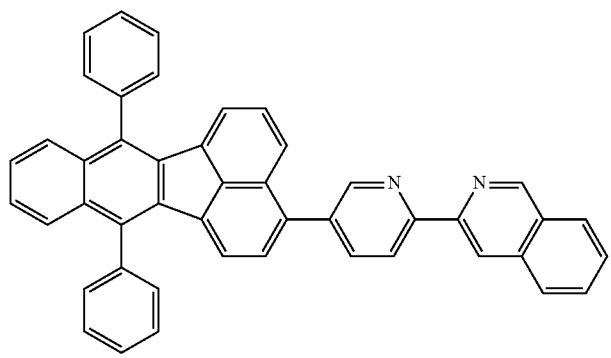
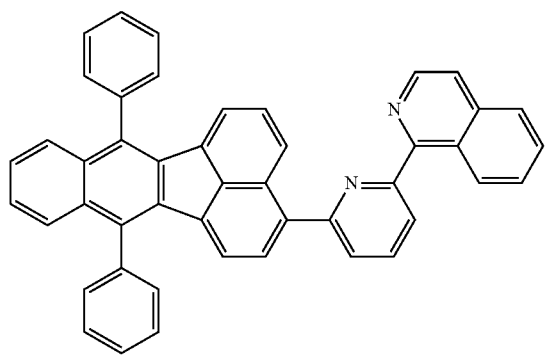
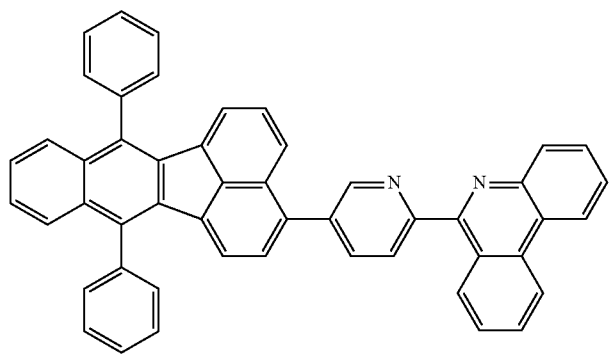
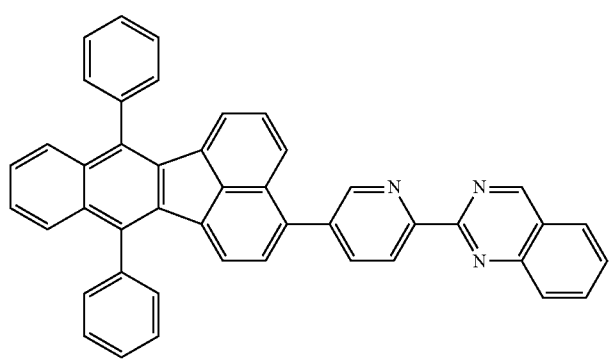

101
102
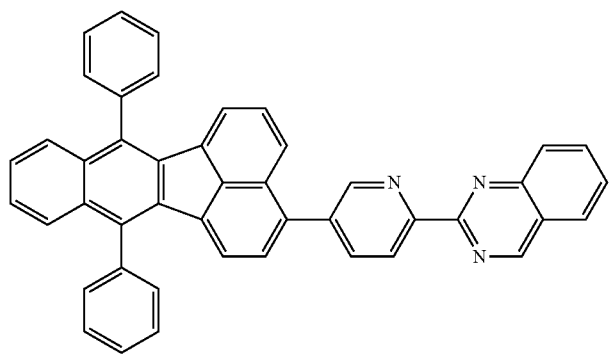
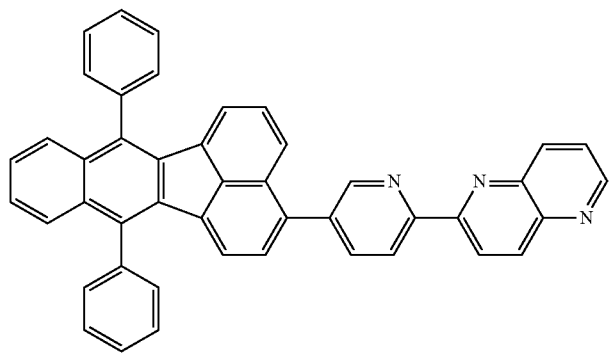
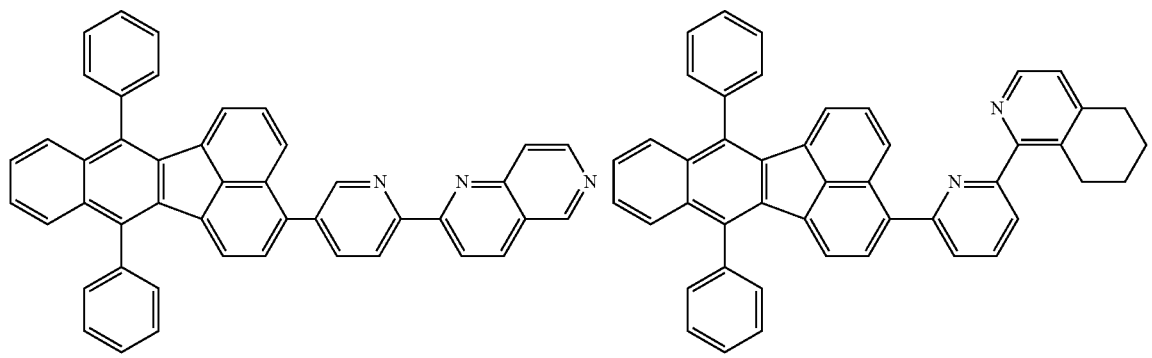
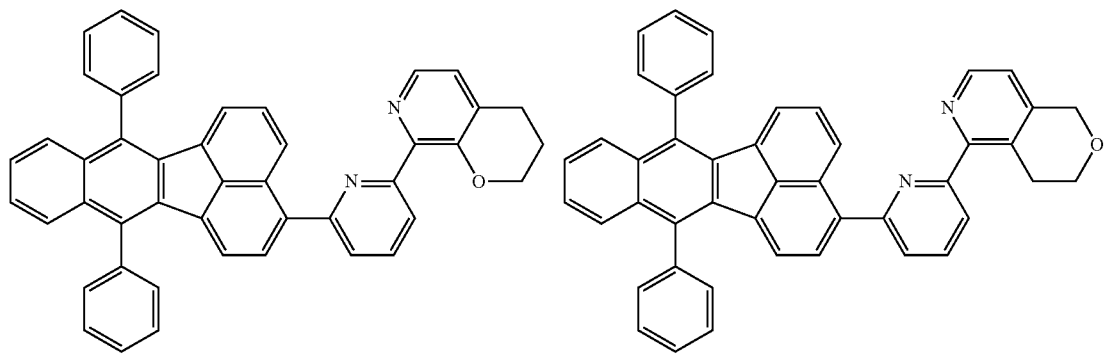

103                                    104
-continued
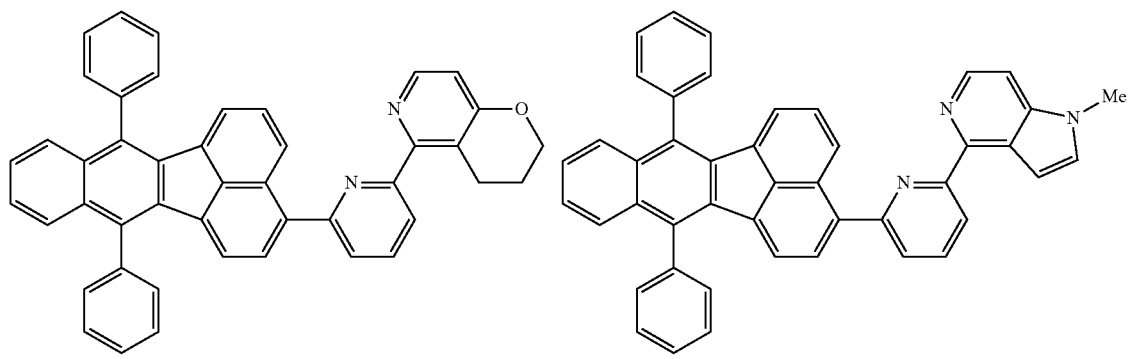
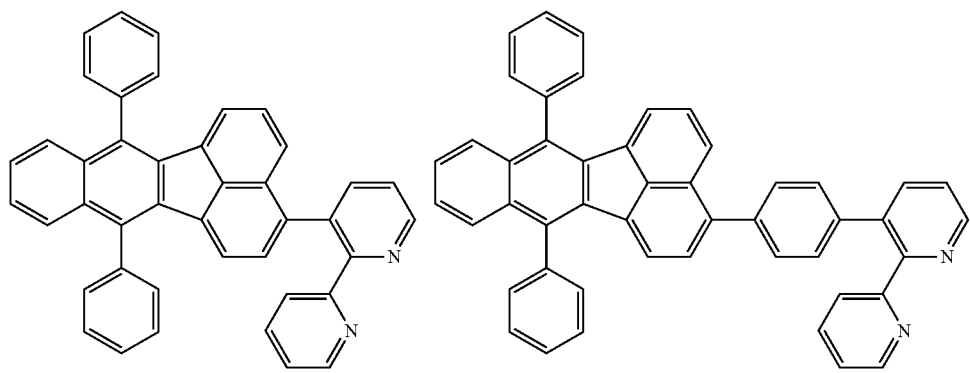
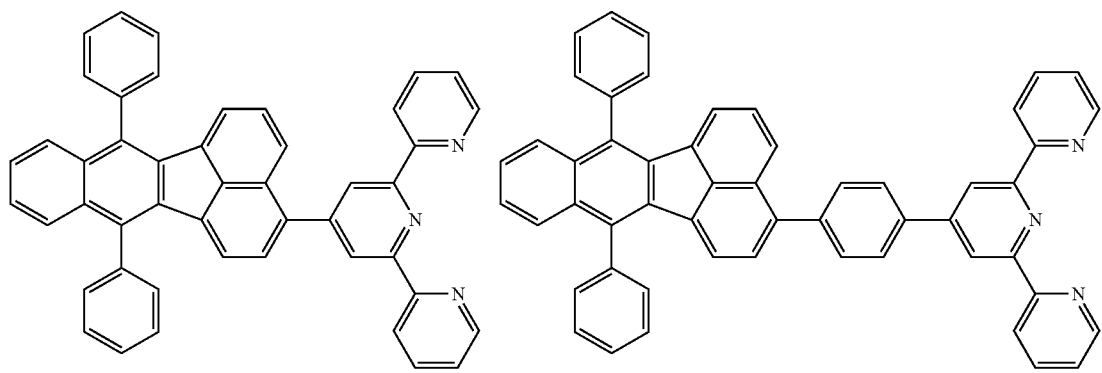
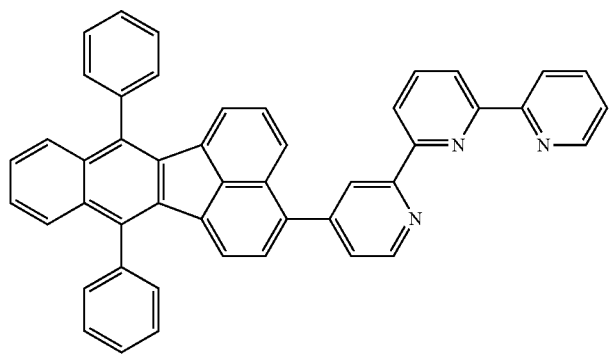

-continued
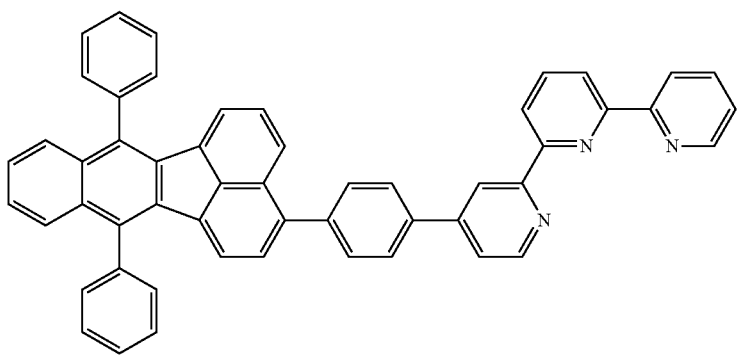
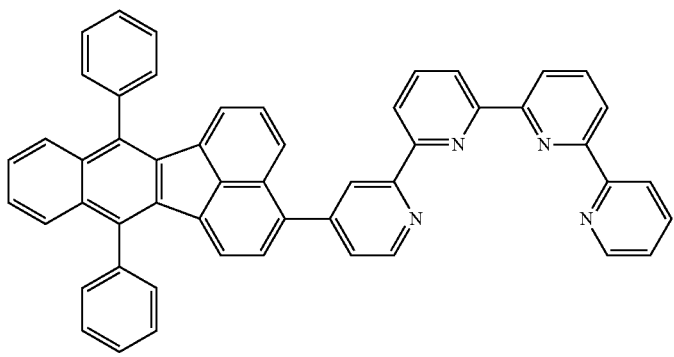
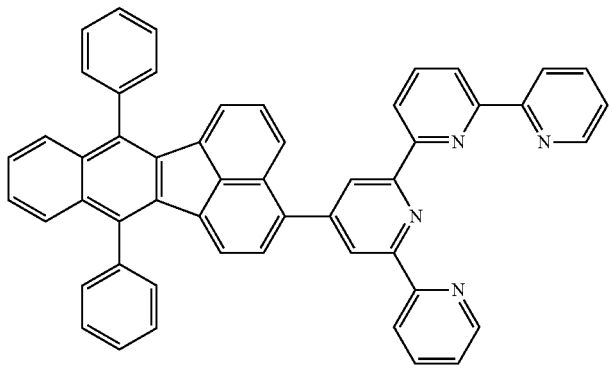
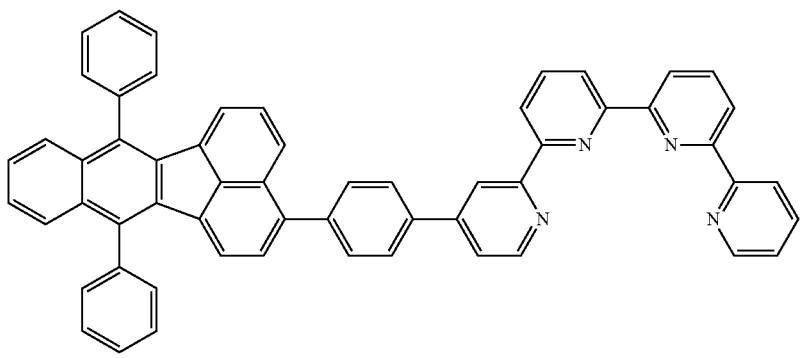

107
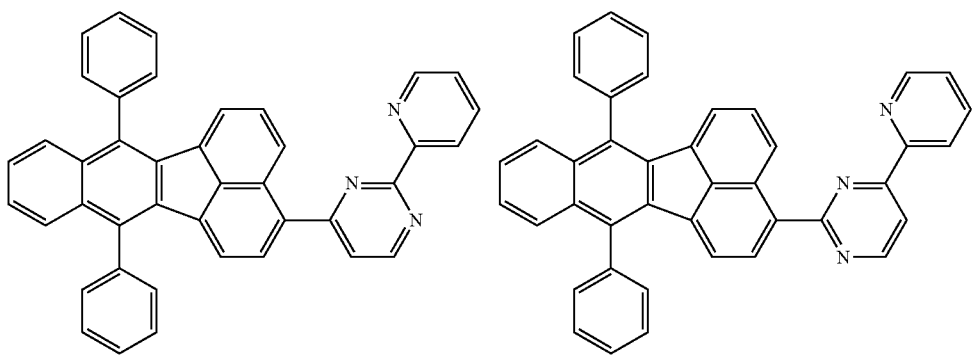
108
-continued
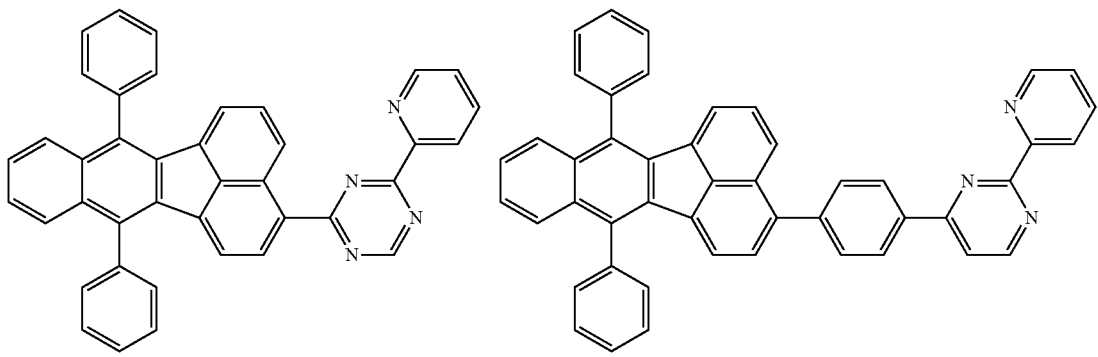
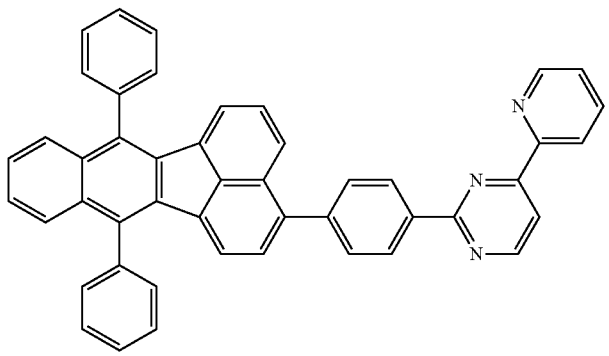
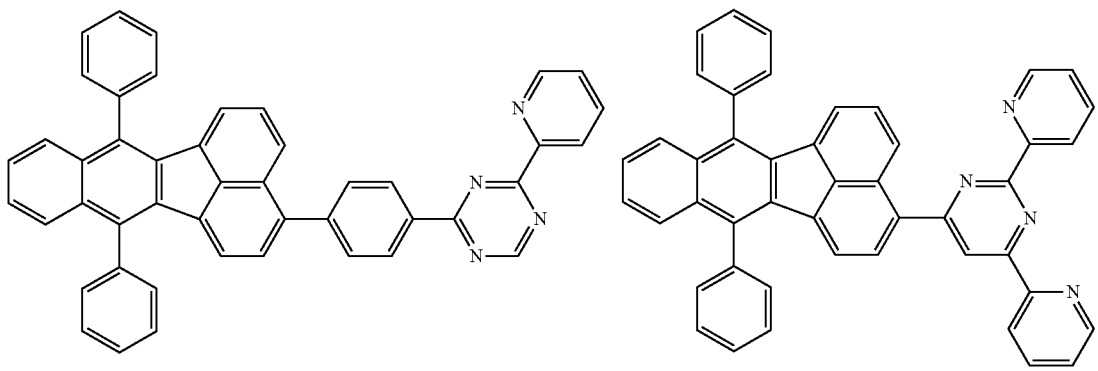

-continued
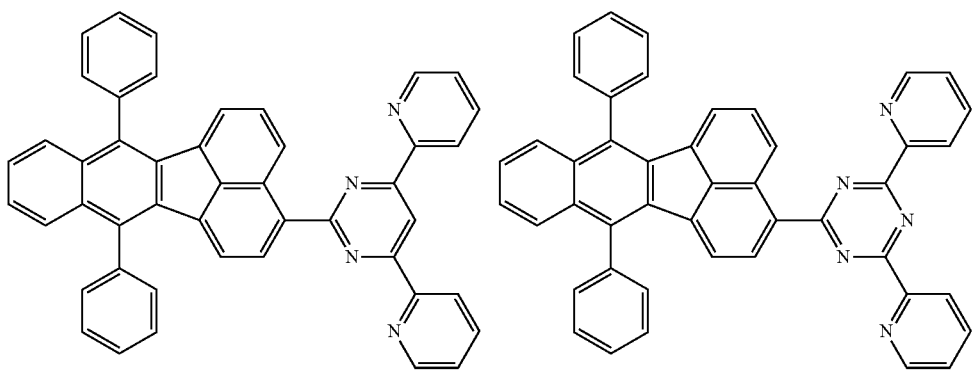
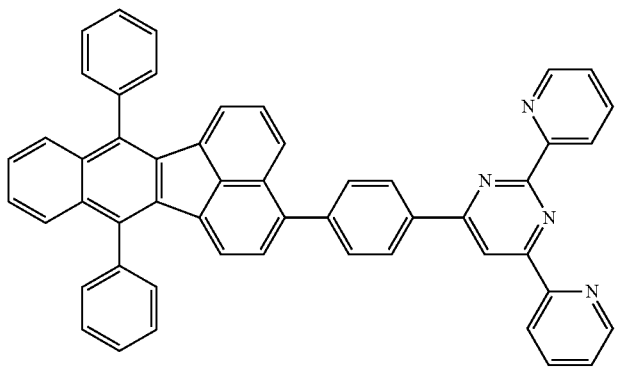
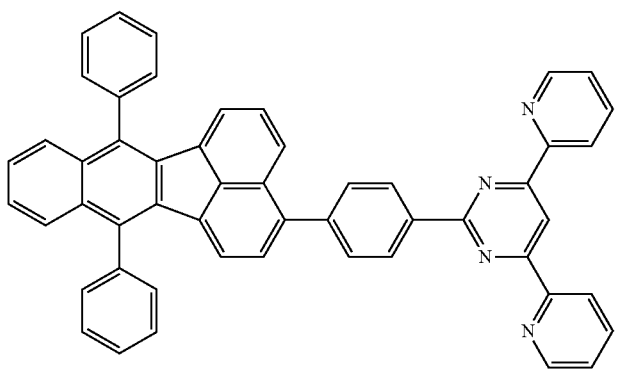
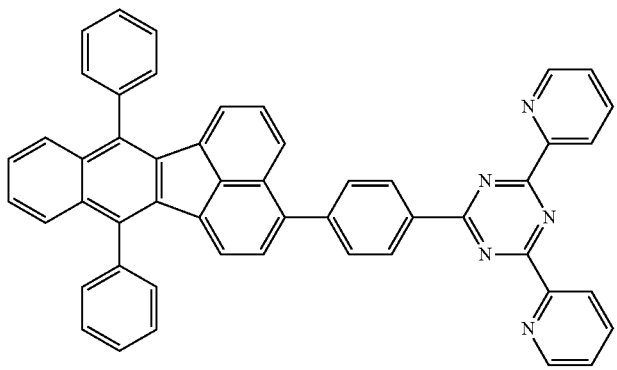

111 112
-continued
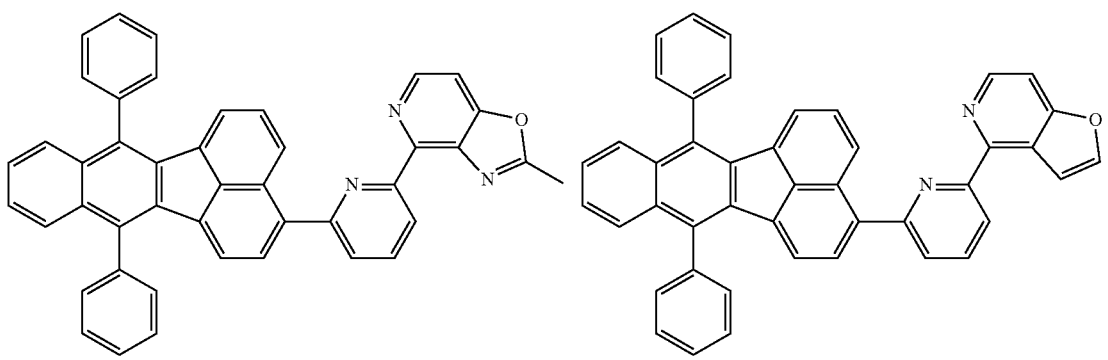
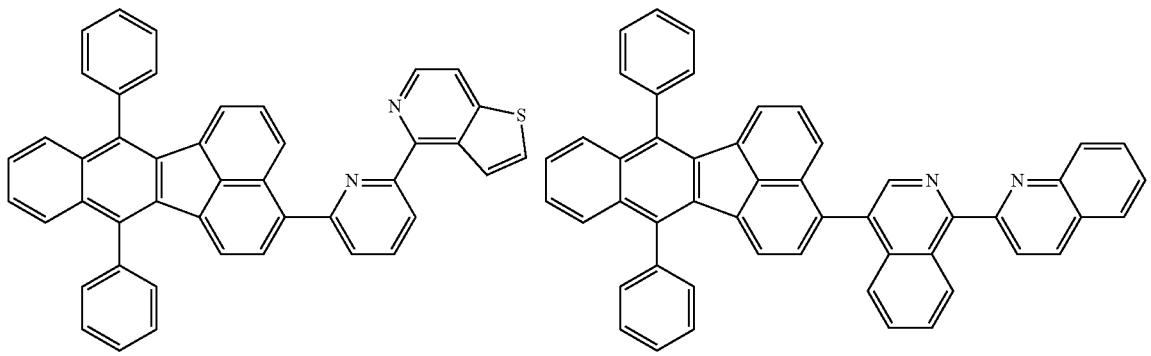
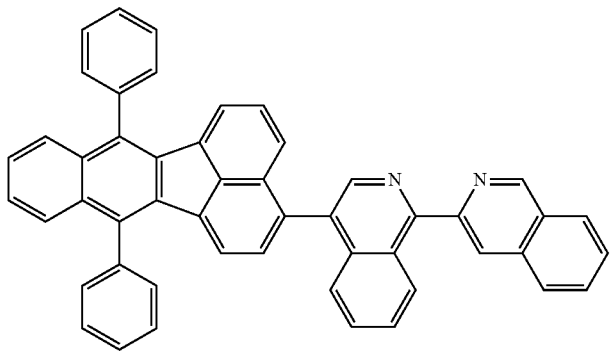
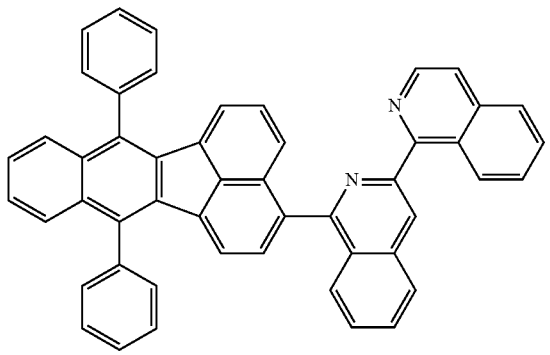

-continued
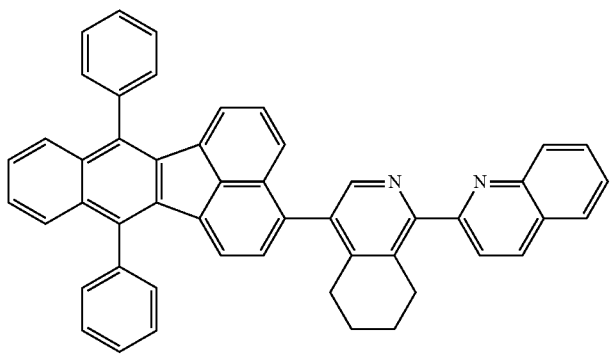
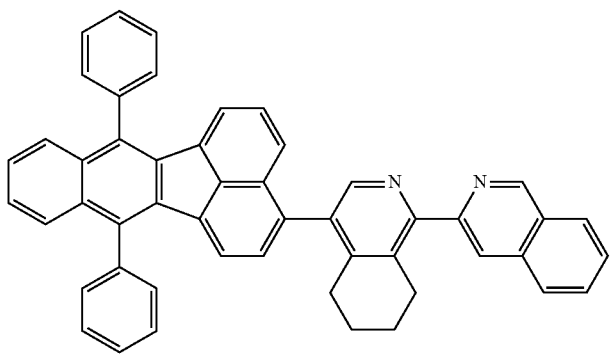
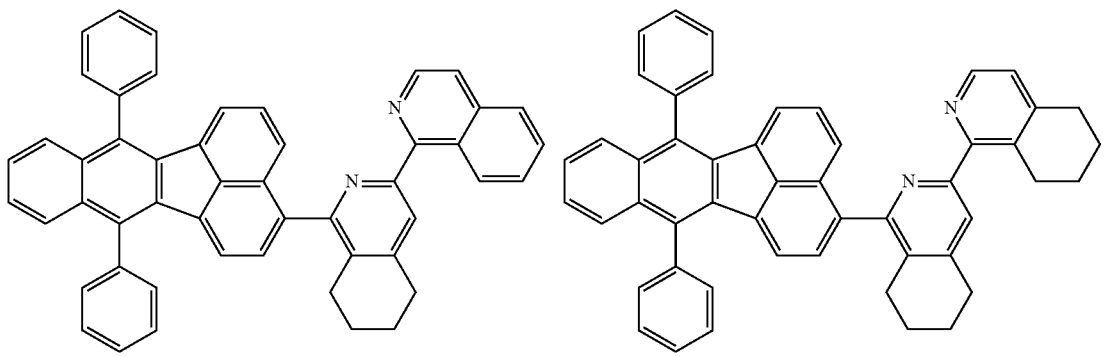
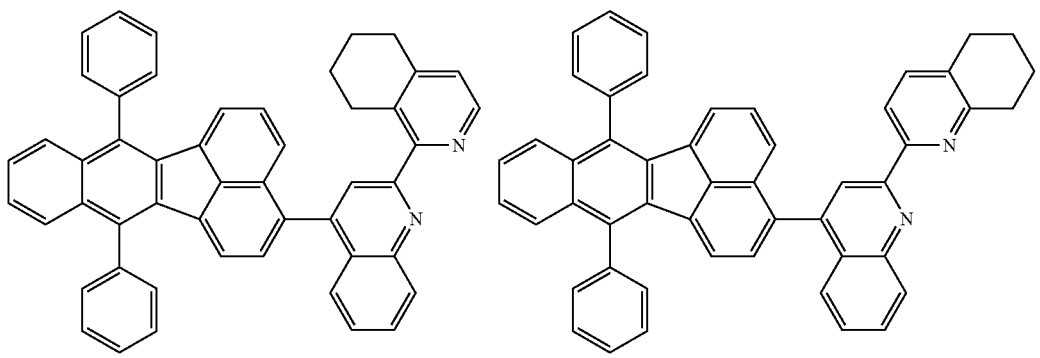

-continued
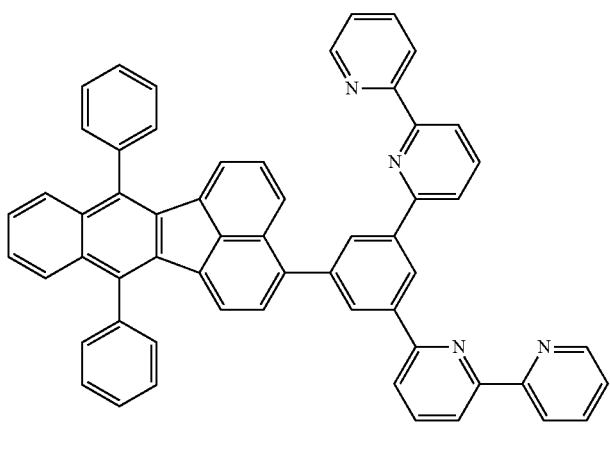
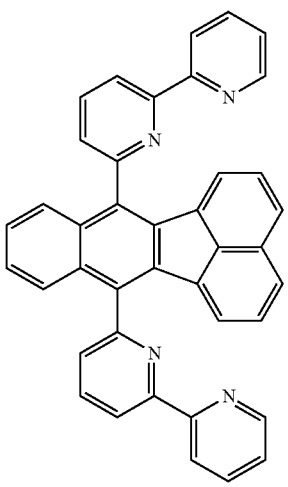
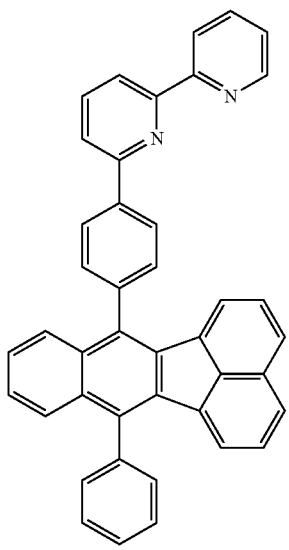
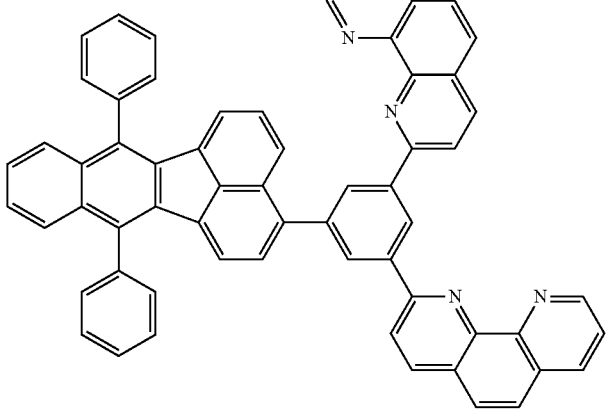
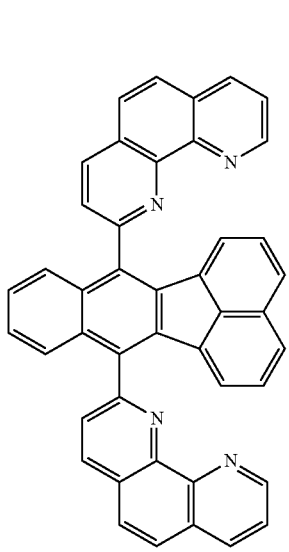
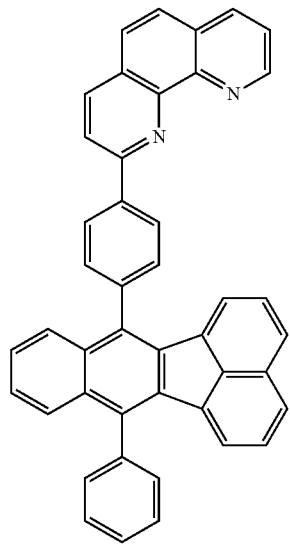

-continued
117
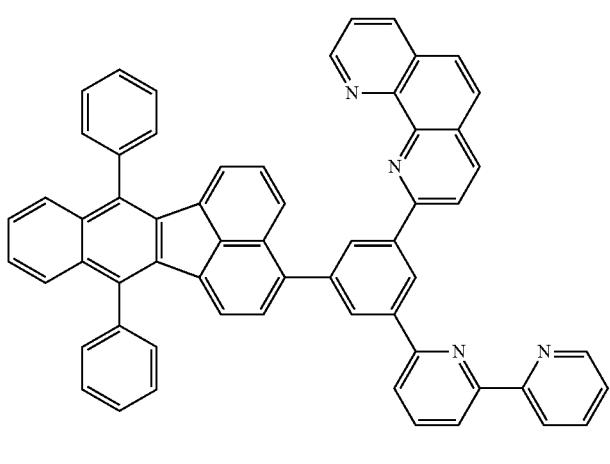
118
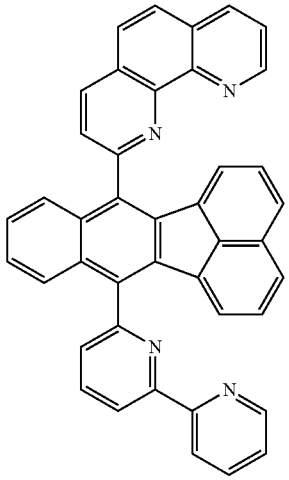
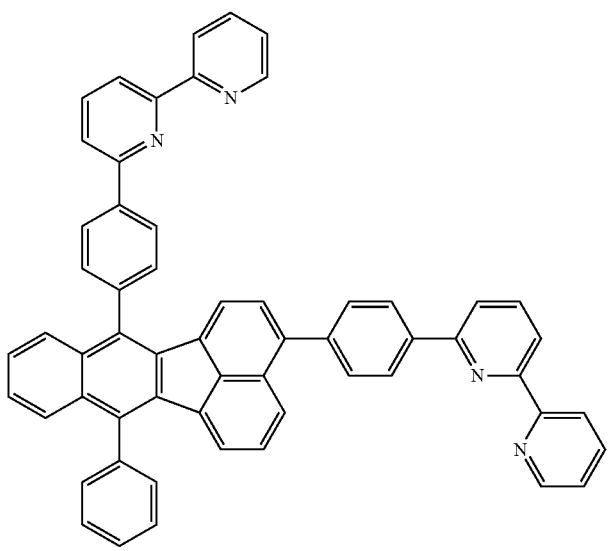
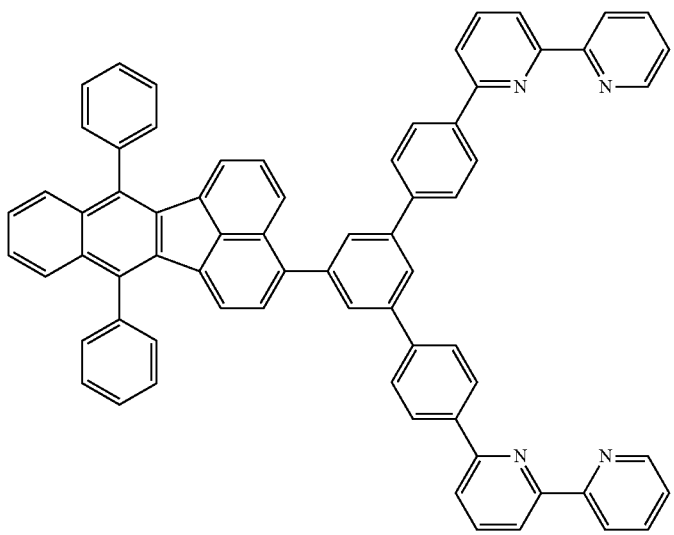

-continued
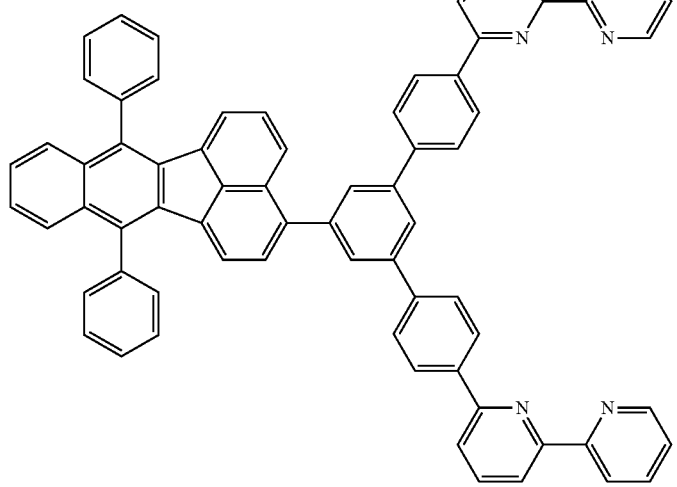
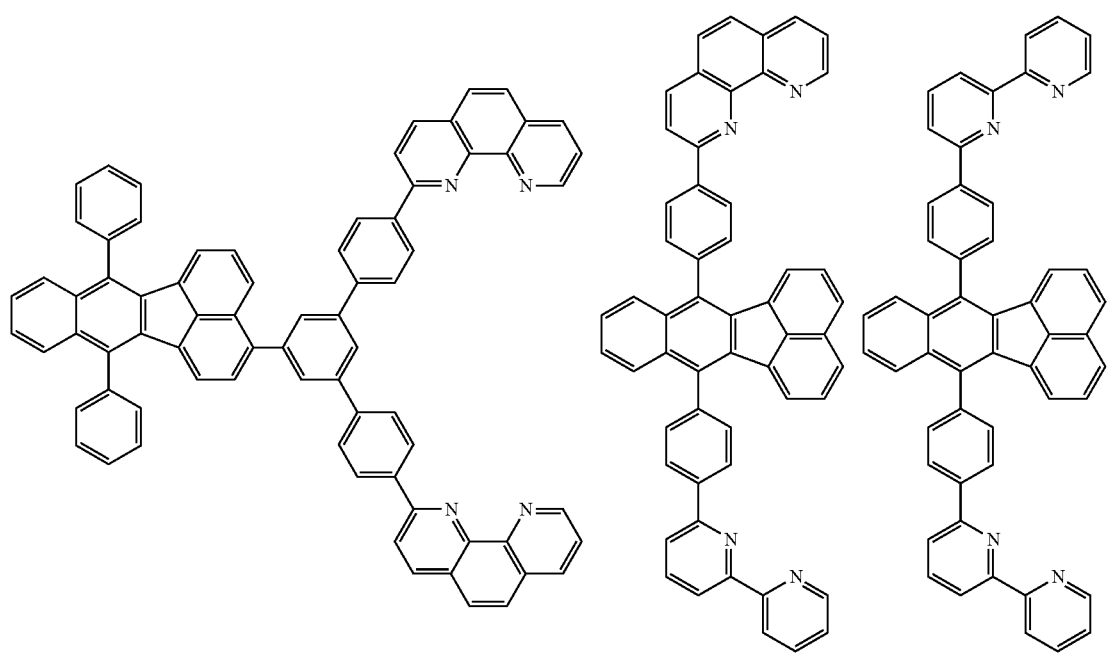

-continued
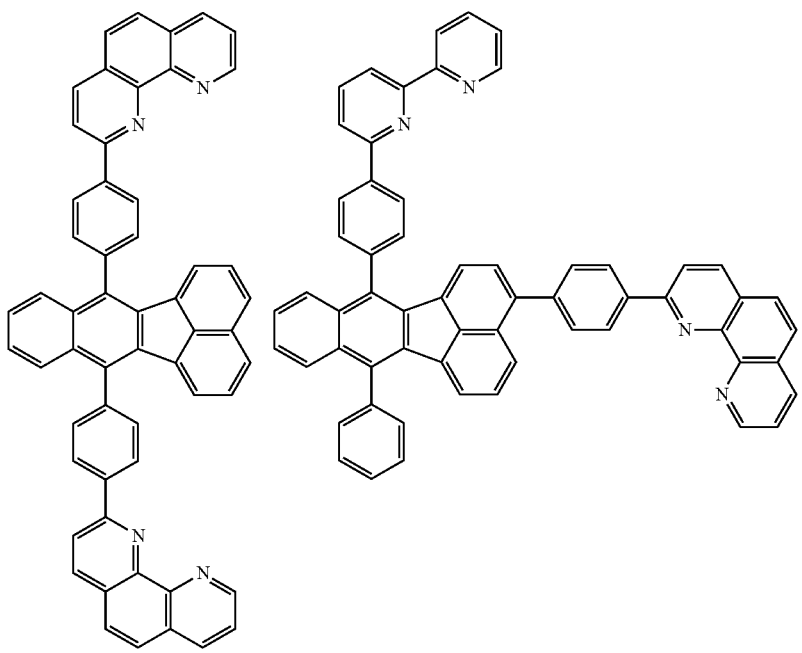
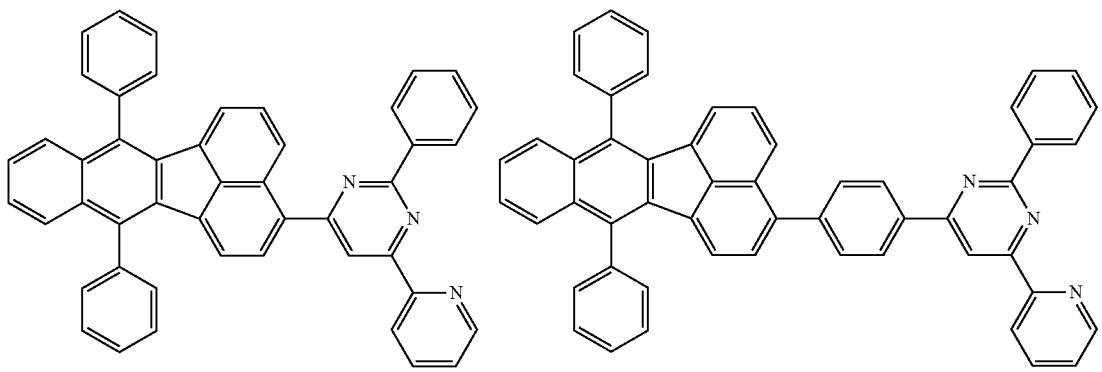
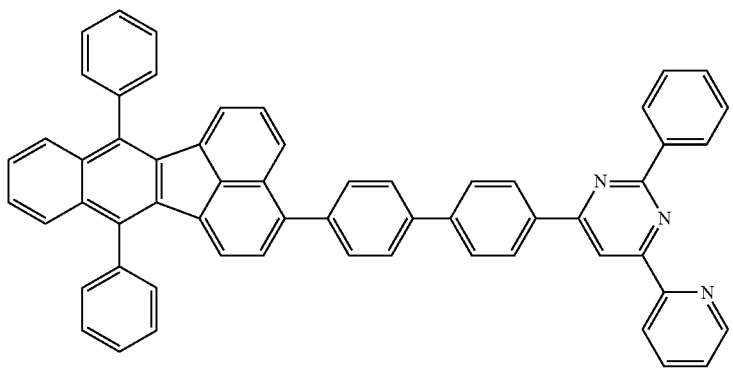

-continued
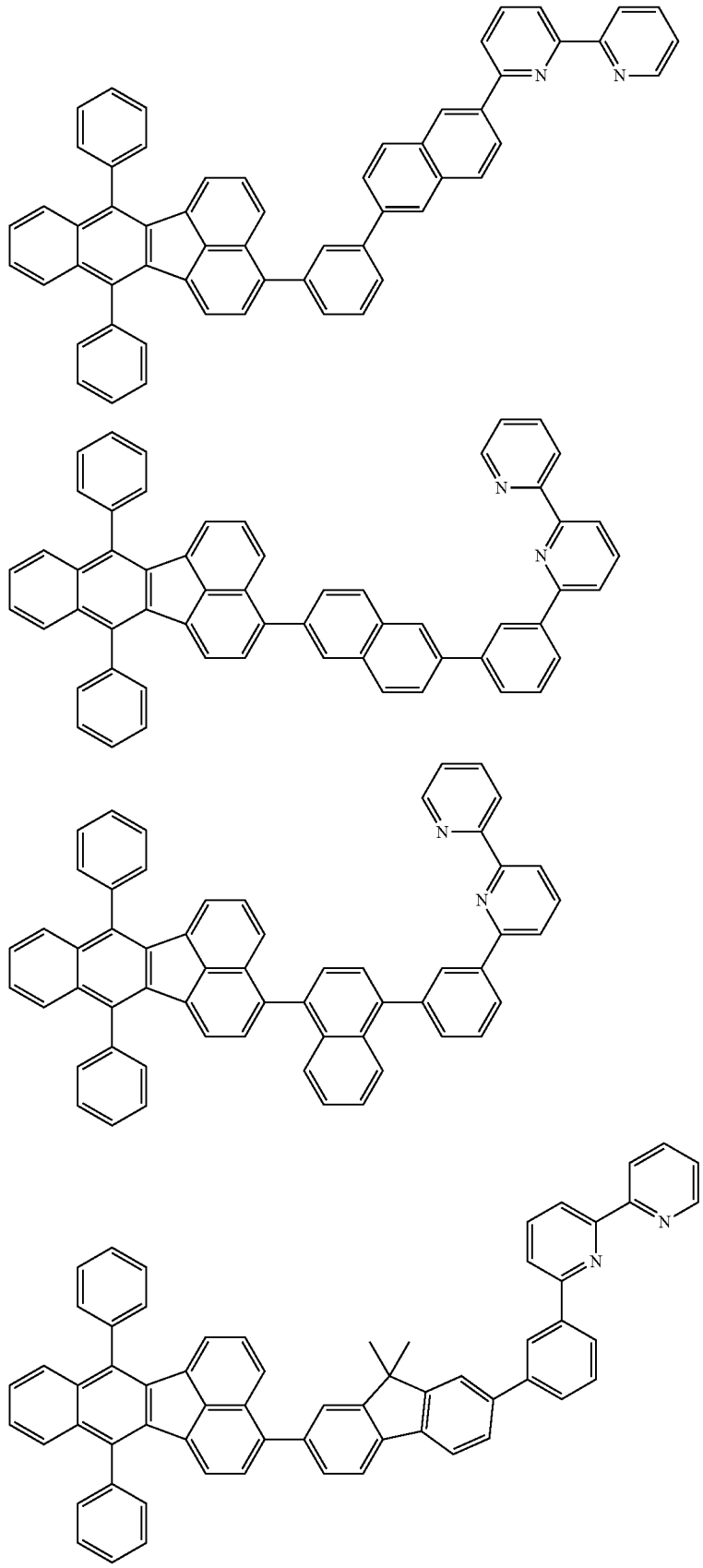

-continued

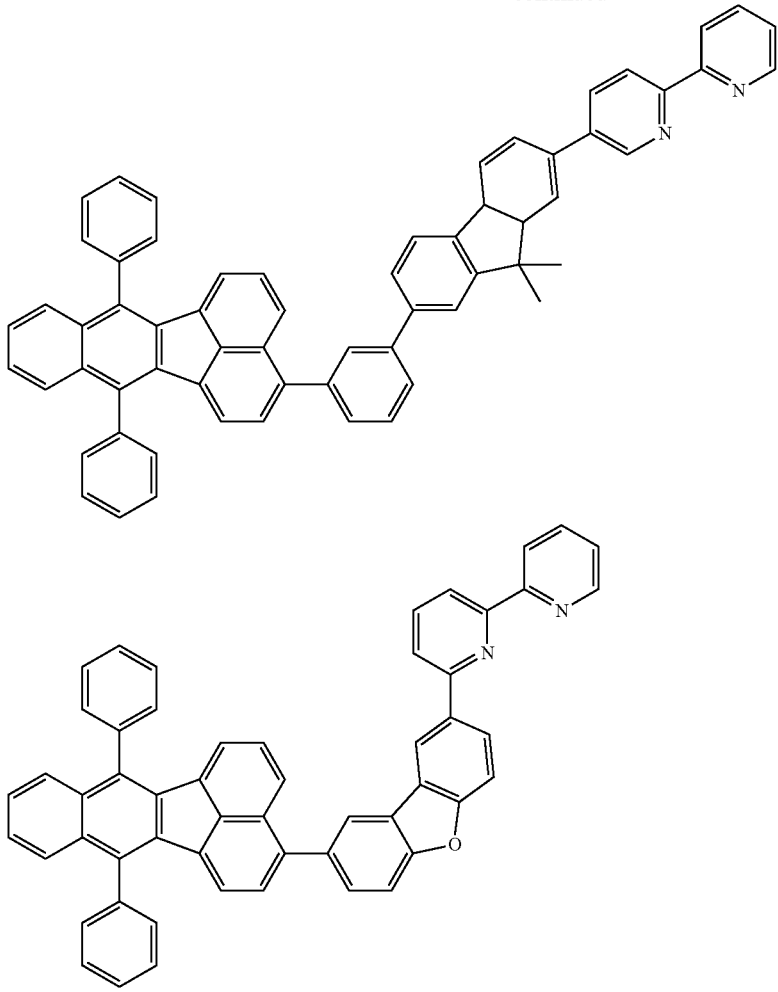

The benzo[k]fluoranthene derivative of the present invention is used preferably as a material for organic EL device, and more preferably as an electron injecting material or electron transporting material of an organic EL device. This is because HAr mediates an electron transfer from the adjoining layer. Also, it may be considered that the benzo[k]fluoranthene derivative of the present invention can be suitably used as a triplet energy blocking material for the reasons as described later.

The benzo[k]fluoranthene skeleton that is a basic skeleton of the benzo[k]fluoranthene derivative of the present invention has high triplet energy and high confinement effect of a triplet exciton, and therefore, it may be considered that for example, by utilizing it as a material of a blocking layer coming into contact with a light emitting layer of an organic EL device, a TTF (triplet-triplet fusion) phenomenon can be promoted. Also, the benzo[k]fluoranthene skeleton that is a basic skeleton of the benzo[k]fluoranthene derivative of the present invention has such a characteristic feature that molecular stacking in a thin film is enhanced due to a height planarity, whereby electron transporting properties become large, and therefore, it may be considered that it is able to promote electron injection into the light emitting layer and enhance recombination efficiency in the light emitting layer, thereby efficiently causing the TTF phenomenon. Furthermore, since the benzo[k]fluoranthene derivative of the present invention contains HAr that is a nitrogen-containing heterocyclic ring with high electron injecting properties from a metal-containing layer, such as an electrode and the like, it may be considered that it is able to realize an organic EL device with a low driving voltage without further laminating an electron injecting layer.

In this way, the benzo[k]fluoranthene derivative of the present invention is a compound provided with both of an electron injection/transport function and a triplet energy blocking function (triplet blocking function).

As described above, the benzo[k]fluoranthene derivative of the present invention is a compound containing a structural site having a triplet blocking functional (triplet blocking structural site) and a structural site having an electron injecting/transporting function. The structural site refers to an individual cyclic structure (single ring or condensed polycyclic ring exclusive of a substituent) which is contained in a compound.

The triplet blocking structural site refers to a structural site having the lowest (smallest) triplet energy among the structural sites contained in a compound. Namely, the triplet blocking structural site is a structural site which determines chiefly the triplet energy of a compound. The triplet energy of the triplet blocking structural site refers to triplet energy of an independent cyclic structure in which hydrogen is substituted at a bonding position of the respective structural sites each other exclusive of a substituent. Furthermore, the triplet blocking structural site must be a condensed polycyclic aromatic hydrocarbon compound. Reasons for this are described below.

The transition state of the condensed ring composed of a hydrocarbon is based on the π-π* transition in which an electron cloud of the cyclic structure participates. An expanse of this π electron cloud is small, and its influences against the excited state of the light emitting layer are small. On the other hand, in the transition state of the case of having a lone pair in the structural site, in view of the fact that the lone pair participates therein, a strong interaction with a triplet exciton produced in the light emitting layer is generated, thereby promoting deactivation of the triplet exciton of a host. As a result, the TTF phenomenon cannot be efficiently caused. In consequence, the triplet blocking structural site of the blocking material must be a condensed ring composed of a hydrocarbon which forms an excited triplet state chiefly on the basis of the π-π* transition.

In the case of using the benzo[k]fluoranthene derivative of the present invention as a blocking material, it is preferable that the triplet energy of the blocking material is larger than the triplet energy of the host of the light emitting layer.

The triplet blocking function of the blocking material is determined chiefly by the triplet blocking structural site. In general, in the case where the triplet exciton produced in the light emitting layer transfer its energy to the adjoining blocking material, the triplet energy is transferred to the structural site having the lowest triplet energy among the respective structural sites of the blocking material. From this matter, in the case where the triplet blocking structural site having the lowest triplet energy among the respective structural sites is a condensed polycyclic aromatic hydrocarbon compound, the blocking material effectively exhibits the triplet blocking function. From the foregoing reasons, in the case where the structural site having the lowest (smallest) triplet energy among the structural sites contained in a compound is not constituted of carbon and hydrogen, the subject compound does not have a triplet blocking structural site.

The TTF phenomenon is hereunder briefly described.

When a voltage is applied to an organic EL device, electrons and holes are injected from an anode and a cathode, and the injected electrons and holes are recombined within a light emitting layer to produce excitons. In its spin state, a singlet exciton accounts for 25%, and a triplet exciton accounts for 75%. In a conventionally known fluorescent device, when the singlet exciton relaxes to the ground state, light is emitted, whereas the remaining triplet exciton returns to the ground state via a thermal deactivation process without emitting light. However, according to S. M. Bachilo, et al. (*J. Phys. Chem. A*, 104, 7711 (2000)), ⅕ of the triplet exciton in a proportion of 75% as produced at the beginning changes to a singlet exciton.

The TTF phenomenon is a phenomenon in which a singlet exciton is produced due to collision and fusion of triplet excitons. By utilizing this TTF phenomenon, not only the singlet exciton in a proportion of 25% produced at the beginning but the singlet exciton produced due to collision and fusion of triplet excitons can be utilized for the light emission, so that the luminous efficiency of the device can be enhanced.

In order to cause the TTF phenomenon efficiently, it is necessary to confine a triplet exciton having a remarkably long exciton lifetime as compared with a single exciton within the light emitting layer.

In the present invention, it is preferable to allow the blocking layer containing the benzo[k]fluoranthene derivative of the present invention to adjoin to a light emitting layer of a fluorescent device. It may be considered that when the blocking layer containing the benzo[k]fluoranthene derivative of the present invention is used for a fluorescent device, the TTF phenomenon is caused, thereby enabling one to realize an organic EL device with high efficiency.

Incidentally, the blocking layer of the present invention is a layer having a blocking function against the triplet energy, and it is different in the function from a hole blocking layer and a charge blocking layer.

It is preferable that the blocking layer containing the benzo[k]fluoranthene derivative of the present invention, the electron injecting layer, or the electron transporting layer further contains a reducing dopant.

Examples of the reducing dopant include a donating metal, a donating metal compound, and a donating metal complex. These reducing dopants may be used singly or in combination of two or more kinds thereof.

Here, the reducing dopant is a material for donating an electron (referred to as "electron donating material"). This electron donating material is a material which interacts with other organic material contained in the blocking layer, the electron injecting layer, or the electron transporting layer together with the electron donating material, or an organic material constituting a layer adjoining to the blocking layer, the electron injecting layer, or the electron transporting layer, thereby producing a radical anion, or a material having an electron donating radical.

The donating metal refers to a metal having a work function of not more than 3.8 eV, and it is preferably an alkali metal, an alkaline earth metal, or a rate earth metal, and more preferably Cs, Li, Na, Sr, K, Mg, Ca, Ba, Yb, Eu, or Ce.

The donating metal compound refers to a compound containing the donating metal, and it is preferably a compound containing an alkali metal, an alkaline earth metal, or a rate earth metal, and more preferably a halide, an oxide, a carbonate, or a borate of such a metal. Examples thereof include compounds represented by $MO_x$ (M is a donating metal, and x is 0.5 to 1.5), $MF_x$ (x is 1 to 3), or $M(CO_3)_x$ (x is 0.5 to 1.5).

The donating metal complex refers to a complex of the donating metal, and it is preferably an organic metal complex of an alkali metal, an alkaline earth metal, or a rare earth metal. Preferably, the donating metal complex is an organometallic complex represented by the following formula (I).

$$M(-Q)_n \quad (I)$$

In the formula, M is a donating metal; Q is a ligand, and preferably a carboxylic acid derivative, a diketone derivative, or a quinoline derivative; and n is an integer of 1 to 4.

Specific examples of the donating metal complex include tungsten paddlewheels described in JP-A-2005-72012, and so on. Furthermore, phthalocyanine compounds having an alkali metal or an alkaline earth metal as a central metal as described in JP-A-11-345687, or the like can also be used as the donating metal complex.

The foregoing reducing dopant is preferably one or more kinds selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex of an alkali metal, an organic complex of an alkaline earth metal, and an organic complex of a rare earth metal, and more preferably an 8-quinolinol complex of an alkali metal.

When the TTF phenomenon is utilized, the triplet energy of a compound constituting the blocking layer composed of the benzo[k]fluoranthene derivative of the present invention must be higher than the triplet energy of a host chiefly constituting the light emitting layer. Preferably, the benzo[k]fluoranthene derivative of the present invention, which is contained in the blocking layer, and the host and the dopant contained in the light emitting layer satisfy the following expressions (1) and (2).

$$E^T b > E^T h \tag{1}$$

$$E^T d > E^T h \tag{2}$$

wherein $E^T h$, $E^T b$, and $E^T d$ represent triplet energies of the host material, the nitrogen-containing heterocyclic derivative of the blocking layer, and the dopant, respectively.

Figure 2:
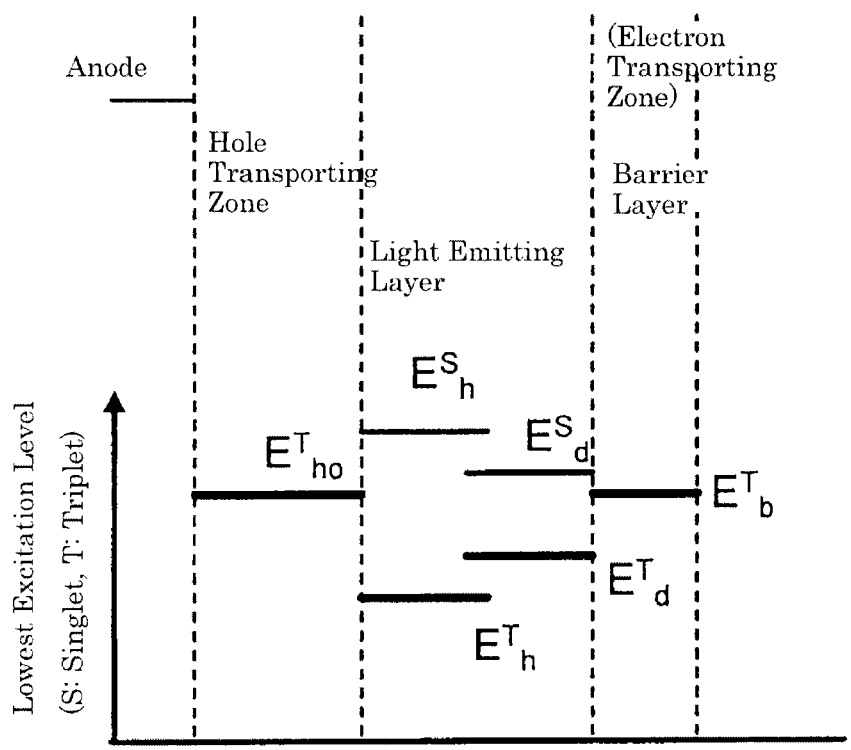
FIG. 2 is a graph showing a relation of an energy gap of each layer of the present invention.

FIG. 1 is a diagrammatic configuration of an organic EL device showing an example of embodiments of the present invention. FIG. 2 schematically expresses the lowest excited singlet energy level and the lowest excited triplet energy level of each layer. Incidentally, in the present invention, the triplet energy refers to a difference between the energy in the lowest excited triplet state and the energy in the ground state, and the singlet energy (also called "energy gap") refers to a difference between the energy in the lowest excited singlet state and the energy in the ground state.

It is enough that the organic EL device of the present invention is a device provided with an anode, a light emitting layer, an electron transporting zone, and a cathode in this order, and in the organic EL device shown in FIG. 1, a hole transporting zone 50, a light emitting layer 20, an electron transporting zone 30, and a cathode 40 are successively laminated in this order from an anode 10. It is preferable that the hole transporting zone 50 is provided between the anode 10 and the light emitting layer 20. In the embodiment shown in FIG. 2, a configuration in which the electron transporting zone is composed of only a blocking layer is shown. But, it is enough that the electron transporting zone includes a blocking layer, and the embodiment of only a blocking layer does not exclude insertion of an electron injecting layer having high injection properties. When an electron injecting layer is formed, general compounds which have been conventionally used for an electron injecting layer can be used, and a heterocyclic ring-containing compound is preferable.

In FIG. 2, a hole injected from the anode is injected into the light emitting layer through the hole transporting zone, and an electron injected from the cathode is injected into the light emitting layer through the electron transporting zone. Thereafter, the hole and the electron are recombined in the light emitting layer, thereby producing a singlet exciton and a triplet exciton. There are two ways of the case where the recombination occurs on the host molecule and the case where the recombination occurs on the dopant molecule. In the present embodiment, as shown in FIG. 2, when the triplet energies of the host and the dopant are defined as $E^T h$ and $E^T d$, respectively, it is preferable that a relation of $E^T h < E^T d$ is satisfied. When this relation is satisfied, as further shown in FIG. 3, the triplet exciton which has been recombined and produced on the host does not transfer to the dopant having higher triplet energy.

The triplet exciton which has been recombined and produced on the dopant molecule rapidly causes energy transfer to the host molecule. That is, the triplet excitons efficiently collide with each other on the host by the TTF phenomenon without causing transfer of the triplet exciton of the host to the dopant, thereby producing a singlet exciton. Furthermore, since a singlet energy $E^S d$ of the dopant is smaller than a singlet energy $E^S h$ of the host, the singlet exciton produced by the TTF phenomenon causes energy transfer from the host to the dopant, thereby contributing to fluorescent light emission of the dopant. Originally, in a dopant to be used for a fluorescent type device, the transition from the excited triplet state to the ground state is forbidden, and in such transition, the triplet exciton did not cause optical energy deactivation but caused thermal deactivation. But, by allowing a relation of the triplet energy between the host and the dopant to satisfy that described above, the triplet exciton efficiently produces a singlet exciton due to mutual collision thereof before causing thermal deactivation, thereby enhancing the luminous efficiency.

In the electron transporting zone, it is preferable to provide a blocking layer in a portion adjoining to the light emitting layer. The blocking layer has such a function that by preventing diffusion of a triplet exciton produced in the light emitting layer into the electron transporting zone and confining the triplet exciton within the light emitting layer, the density of the triplet exciton is increased, thereby efficiently causing the TTF phenomenon.

Figure 3:
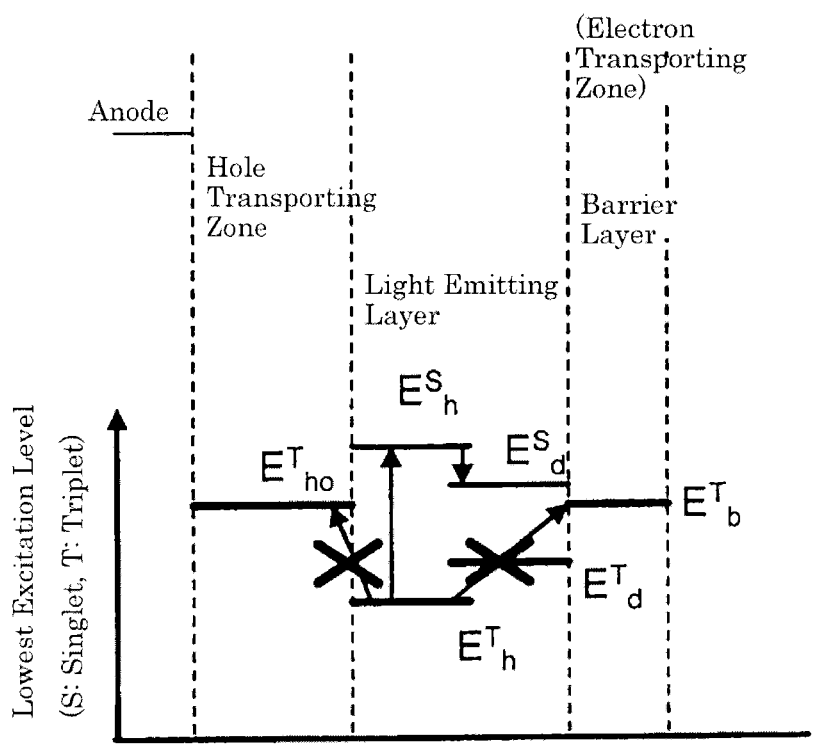
FIG. 3 is a graph showing an action on the basis of a relation of an energy gap of each layer of the present invention.

In order to prevent the diffusion of a triplet exciton, as shown in FIGS. 2 and 3, it is preferable that the triplet energy $E^T b$ of the compound constituting the blocking layer is larger than $E^T h$ and furthermore, larger than $E^T d$. Since the blocking layer prevents the diffusion of the triplet exciton produced in the light emitting layer into the electron transporting zone, the triplet exciton of the host efficiently becomes a singlet exciton within the light emitting layer, and the singlet exciton transfers to the dopant, thereby causing optical energy deactivation. A material which forms the blocking layer is the benzo[k]fluoranthene derivative of the present invention. Since the benzo[k]fluoranthene derivative of the present invention has hole resistance, it is hardly deteriorated, thereby prolonging the lifetime of the device.

Since the blocking layer containing the benzo[k]fluoranthene derivative of the present invention can also play a role as an electron injecting/transporting function, the electron injected in the blocking material more easily donates an electron via an electron transport structural site. That is, in view of the fact that the electron injected in the blocking material transfers to a structural site having a high LUMO level, it contributes to the electron injection into the light emitting layer.

A low-work function metal-containing layer may be provided between the electron transporting zone and the cathode as described above. The low-work function metal-containing layer refers to a layer containing a low-work function metal or a low-work function metal compound. The low-work function metal-containing layer may be formed of only a low-work function metal or a low-work function metal compound, or may be formed by adding, as a donor, a low-work function metal, a low-work function metal compound, or a low-work function metal complex to the material used for the electron transporting layer. The low-work function metal refers to a metal having a work function of not more than 3.8 eV. Examples of the metal having a work function of not more than 3.8 eV include an alkali metal, an alkaline earth metal, and so on. Examples of the alkali metal include Li, Na, K, Cs, and so on. Examples of the alkaline earth metal include Mg, Ca, Sr, Ba, and so on. Other examples include Yb, Eu, Ce, and so on. Also, as the low-work function metal compound, oxides, halides, carbonates or borates of low-work function metal are preferable. Examples of the halide include a fluoride, a chloride, and a bromide, with a fluoride being preferable. For example, LiF is preferably used. Also, the low-work function metal complex is a complex of a low-work function metal, and organometallic complexes of an alkali metal, an alkaline earth metal, or a rare earth metal are preferable.

Incidentally, the enhancement of the efficiency to be brought by utilizing the TTF phenomenon is remarkable in a blue fluorescent layer. However, even in a green fluorescent layer and a red fluorescent layer, the luminous efficiency can be enhanced by confining the triplet energy within the light emitting layer.

The light emitting layer of the organic EL device of the present invention preferably contains at least one kind of an anthracene derivative represented by the following formula (4) or a pyrene derivative represented by the following formula (5) as a host.

Anthracene Derivative

The anthracene derivative is represented by the following formula (4):

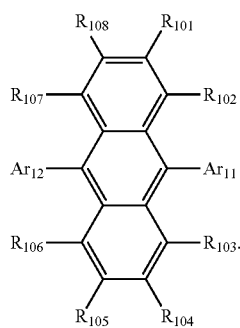

(4)

Each of $Ar_{11}$ and $Ar_{12}$ independently represents a substituted or unsubstituted monocyclic group having 5 to 50 ring atoms, a substituted or unsubstituted condensed ring group having 8 to 50 ring atoms, or a group constituted of a combination of a monocyclic group and a condensed ring group.

Each of $R_{101}$ to $R_{108}$ independently represents a group selected from a hydrogen atom, a substituted or unsubstituted monocyclic group having 5 to 50 ring atoms, a substituted or unsubstituted condensed ring group having 8 to 50 ring atoms; a group constituted of a combination of a monocyclic group and a condensed ring group, a substituted or unsubstituted alkyl group having 1 to 50 carbon atoms; a substituted or unsubstituted cycloalkyl group having 3 to 50 ring carbon atoms; a substituted or unsubstituted alkoxy group having 1 to 50 carbon atoms; a substituted or unsubstituted aralkyl group having 7 to 50 carbon atoms; a substituted or unsubstituted aryloxy group having 6 to 50 ring carbon atoms; a substituted or unsubstituted silyl group, a halogen atom, and a cyano group.

In the formula (4), the monocyclic ring refers to a group constituted of only a non-condensed ring.

Specific examples of the monocyclic group having 5 to 50 (preferably 5 to 30, and more preferably 5 to 20) ring atoms include an aromatic group, such as a phenyl group, a biphenyl group, a terphenyl group, a quaterphenyl group, and the like; and a heterocyclic group, such as a pyridyl group, a pyrazyl group, a pyrimidyl group, a triazinyl group, a furyl group, a thienyl group, and the like, with a phenyl group, a biphenyl group, and a terphenyl group being preferable.

In the formula (4), the condensed ring group refers to a group having two or more ring structures condensed therein.

Specific examples of the foregoing condensed ring group having 8 to 50 (preferably 8 to 30, and more preferably 8 to 20) ring atoms include a condensed aromatic ring group, such as a naphthyl group, a phenanthryl group, an anthryl group, a chrysenyl group, a benzoanthryl group, a benzophenanthryl group, a triphenylenyl group, a benzochrysenyl group, an indenyl group, a fluorenyl group, a 9,9-dimethylfluorenyl group, a benzofluorenyl group, a dibenzofluorenyl group, a fluoranthenyl group, a benzofluoranthenyl group, and the like; and a condensed heterocyclic group, such as a benzofuranyl group, a benzothiophenyl group, an indolyl group, a dibenzofuranyl group, a dibenzothiophenyl group, a carbazolyl group, a quinolyl group, a phenanthrolinyl group, and the like, with a naphthyl group, a phenanthryl group, an anthryl group, a 9,9-dimethylfluorenyl group, a fluoranthenyl group, a benzoanthryl group, a dibenzothiophenyl group, a dibenzofuranyl group, and a carbazolyl group being preferable.

Specific examples of the alkyl group having 1 to 50 carbon atoms, the cycloalkyl group having 3 to 50 ring carbon atoms, the alkoxy group having 1 to 50 carbon atoms, an aryloxy group having 6 to 50 ring carbon atoms, and the substituted or unsubstituted silyl group are the same as those in the formula (1).

The aralkyl group having 7 to 50 carbon atoms is represented by —Y—Z. Examples of Y include an alkylene corresponding to the alkyl as described above; and examples of Z include the aryl as described above. In the aralkyl group having 7 to 50 carbon atoms, the aryl moiety thereof has 6 to 49 (preferably 6 to 30, more preferably 6 to 20, and especially preferably 6 to 12) carbon atoms; the alkyl moiety thereof has 1 to 44 (preferably 1 to 30, more preferably 1 to 20, still more preferably 1 to 10, and especially preferably 1 to 6) carbon atoms; and examples thereof include a benzyl group, a phenylethyl group, and a 2-phenylpropan-2-yl group.

In the formula (4), the optional substituent of the terms "substituted or unsubstituted" in each of $Ar_{11}$, $Ar_{12}$, and $R_{101}$ to $R_{108}$ is preferably a monocyclic group, a condensed ring group, an alkyl group, a cycloalkyl group, a silyl group, an alkoxy group, a cyano group, or a halogen atom (especially fluorine), and especially preferably a monocyclic group or a condensed ring group. Examples of preferred specific substituents are the same as each of the groups in the formula (4) and as each of the groups in the formula (1).

The anthracene derivative represented by the formula (4) is preferably any of the following anthracene derivatives (A), (B) and (C), and it is selected depending upon the constitution of the organic EL device to be applied or the required properties.

Anthracene Derivative (A)

The anthracene derivative is one represented by the formula (4) wherein each of $Ar_{11}$ and $Ar_{12}$ independently represents a substituted or unsubstituted condensed ring group having 8 to 50 ring atoms. The anthracene derivative can be separated into the case where $Ar_{11}$ and $Ar_{12}$ are the same substituted or unsubstituted condensed ring group and the case where $Ar_{11}$ and $Ar_{12}$ are different substituted or unsubstituted condensed ring groups.

The anthracene derivative represented by the formula (4) wherein $Ar_{11}$ and $Ar_{12}$ are different substituted or unsubstituted condensed ring groups (inclusive of position isomers) is especially preferable, and specific examples of the condensed ring are those described above. Above all, a naphthyl group, a phenanthryl group, a benzanthryl group, a 9,9-dimethylfluorenyl group, and a dibenzofuranyl group are preferable.

Anthracene Derivative (B)

The subject anthracene derivative is one represented by the formula (4) wherein one of $Ar_{11}$ and $Ar_{12}$ is a substituted or unsubstituted monocyclic group having 5 to 50 ring atoms and the other is a substituted or unsubstituted condensed ring group having 8 to 50 ring atoms.

A preferred embodiment is one in which $Ar_{12}$ is a naphthyl group, a phenanthryl group, a benzoanthryl group, a 9,9- dimethylfluorenyl group, or a dibenzofuranyl group and $Ar_{11}$ is a phenyl group substituted with a monocyclic group or a condensed ring group.

Specific examples of the preferred monocyclic group and the condensed ring group are those described above.

Another preferred embodiment is one in which $Ar_{12}$ is a condensed ring group and $Ar_{11}$ is an unsubstituted phenyl group. In that case, the condensed ring group is especially preferably a phenanthryl group, a 9,9-dimethylfluorenyl group, a dibenzofuranyl group, or a benzoanthryl group.

Anthracene Derivative (C)

The subject anthracene derivative is one represented by the formula (4) wherein each of $Ar_{11}$ and $Ar_{12}$ independently represents a substituted or unsubstituted monocyclic group having 5 to 50 ring atoms.

A preferred embodiment is one in which both of $Ar_{11}$ and $Ar_{12}$ are substituted or unsubstituted phenyl groups.

As a more preferred embodiment, there are included the case where $Ar_{11}$ is an unsubstituted phenyl group and $Ar_{12}$ is a phenyl group substituted by a monocyclic group or a condensed ring group and the case where each of $Ar_{11}$ and $Ar_{12}$ independently represents a phenyl group substituted by a monocyclic group or a condensed ring group.

Specific examples of the monocyclic group and the condensed ring group which are preferable as the substituent are those described above. More preferably, examples of the monocyclic ring as the substituent include a phenyl group and a biphenyl group; and examples of the condensed ring group as the substituent include a naphthyl group, a phenanthryl group, a 9,9-dimethylfluorenyl group, a dibenzofuranyl group, and a benzoanthryl group.

Pyrene Derivative

The pyrene derivative represented by the formula (5) is the following compound:

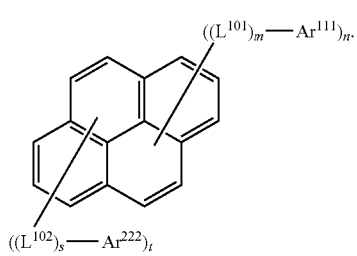

(5)

In the above formula, each of $Ar^{111}$ and $Ar^{222}$ independently represents a substituted or unsubstituted aryl group having 6 to 30 ring carbon atoms.

Each of the $L^{101}$ and $L^{102}$ independently represents a substituted or unsubstituted divalent aryl group having 6 to 30 ring carbon atoms or a heterocyclic group.

Subscript m represents an integer of 0 to 1; n represents an integer of 1 to 4; s represents an integer of 0 to 1; and t represents an integer of 0 to 3.

$L^{101}$ $Ar^{111}$ is bonded at any of 1- to 5-positions of pyrene and $L^{102}$ or $Ar^{222}$ is bonded at any of 6- to 10-positions of pyrene.

In the formula (5), each of $L^{101}$ and $L^{102}$ is preferably a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, or a divalent aryl group composed of a combination of these substituents.

Also, this substituent is the same as the substituent in the "substituted or unsubstituted . . . " in the formula (1). The substituent of each of $L^{101}$ and $L^{102}$ is preferably an alkyl group having 1 to 20 carbon atoms.

In the formula (5), m is preferably an integer of 0 to 1. In the formula (5), n is preferably an integer of 1 to 2. In the formula (5), s is preferably an integer of 0 to 1.

In the formula (5), t is preferably an integer of 0 to 2.

The aryl group of each of $Ar^{111}$ and $Ar^{222}$ is the same as those in the formula (1).

The aryl group is preferably a substituted or unsubstituted aryl group having 6 to 20 ring carbon atoms, and more preferably a substituted or unsubstituted aryl group having 6 to 16 ring carbon atoms. Preferred specific examples of the aryl group include a phenyl group, a naphthyl group, a phenanthryl group, a fluorenyl group, a biphenyl group, an anthryl group, and a pyrenyl group.

The light emitting layer containing the anthracene derivative represented by the formula (4) or the pyrene derivative represented by the formula (5) preferably comes into contact with the blocking layer containing the benzo[k]fluoranthene derivative of the invention, the electron injecting layer, or the electron transporting layer. When the light emitting layer comes into contact with the blocking layer containing the benzo[k]fluoranthene derivative of the invention, the electron injecting layer, or the electron transporting layer, the luminous efficiency can be enhanced utilizing the TTF phenomenon.

In the organic EL device of the present invention, the light emitting layer may contain a light emitting dopant (phosphorescent dopant and/or fluorescent dopant).

The fluorescent dopant is a compound capable of causing light emission from a singlet exciton. The fluorescent dopant is preferably a compound which is selected in conformity with the required luminescent color among an amine based compound, an aromatic compound, a chelate complex, such as a tris(8-quinolinolato)aluminum complex, a coumarin derivative, a tetraphenylbutadiene derivative, a bisstyrylarylene derivative, an oxadiazole derivative, and the like. A styrylamine compound, a styryldiamine compound, an arylamine compound, an aryldiamine compound, and an aromatic compound are more preferable, and a condensed polycyclic amine derivative and an aromatic compound are still more preferable. These fluorescent dopants may be used singly or in combination of plural kinds thereof.

The condensed polycyclic amine derivative is preferably one represented by the following formula (12):

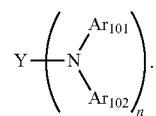

(12)

In the formula, Y represents a substituted or unsubstituted condensed aryl group having 10 to 50 ring carbon atoms.

Each of $Ar_{101}$ and $Ar_{102}$ represents a substituted or unsubstituted aryl group having 6 to 50 ring carbon atoms or a substituted or unsubstituted heterocyclic group having 5 to 50 ring atoms.

Specific examples of Y include those described above regarding the condensed aryl group, and preferred examples thereof include a substituted or unsubstituted anthryl group, a substituted or unsubstituted pyrenyl group, and a substituted or unsubstituted chrysenyl group.

Specific examples of each of $Ar_{101}$ and $Ar_{102}$ include those described above regarding the aryl group or heterocyclic group, and preferred examples thereof include a substituted or unsubstituted phenyl group, a substituted or unsubstituted naphthyl group, a substituted or unsubstituted biphenyl group, a substituted or unsubstituted terphenyl group, and a substituted or unsubstituted dibenzofuranyl group.

Subscript n is an integer of 1 to 4 and preferably an integer of 1 to 2.

In the formula (12), examples of the alkyl group, the alkoxy group, the aryl group, the aryloxy group, and the heterocyclic group include those exemplified above.

The aromatic compound is preferably a benzo[k]fluoranthene compound represented by the following formula (13):

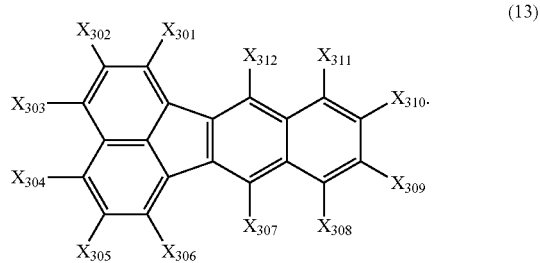

(13)

In the formula, each of $X_{301}$ to $X_{306}$ and $X_{308}$ to $X_{311}$ is independently selected from a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 8 ring carbon atoms, a substituted or unsubstituted alkoxy group having 1 to 20 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, an amino group substituted with a substituted or unsubstituted aryl group having 6 to 30 ring carbon atoms, a halogen atom, a cyano group, a nitro group, a hydroxyl group, and a carboxyl group.

Each of $X_{307}$ and $X_{312}$ is independently selected from a substituted or unsubstituted aryl group having 6 to 30 ring carbon atoms, a substituted or unsubstituted heterocyclic group having 5 to 30 ring atoms, a substituted or unsubstituted alkyl group having 1 to 20 carbon atoms, and a substituted or unsubstituted cycloalkyl group having 3 to 8 ring carbon atoms.

However, $X_{303}$ and $X_{304}$ are different.

Also, in $X_{301}$ to $X_{312}$, the adjoining substituents may be bonded to each other to form a saturated or unsaturated cyclic structure, and such a cyclic structure may be substituted.

$X_{301}$ or $X_{304}$ in the formula (13) is preferably a substituted or unsubstituted aryl group having 6 to 30 ring carbon atoms. Also, the substituent of the terms "substituted or unsubstituted" in the formula (13) is preferably a cyano group or a halogen atom.

In the formula (13), examples of each of the aryl group, the heterocyclic group, the alkyl group, the cycloalkyl group, the alkoxy group, the aralkyl group, the aryloxy group, the arylthio group, the alkoxycarbonyl group, and the halogen atom include those exemplified above.

Incidentally, when the TTF phenomenon is utilized, from the standpoint of efficiency, the dopant is preferably a dopant exhibiting fluorescent light emission, a main peak wavelength of which is not more than 550 nm, and more preferably a blue light emitting dopant.

The main peak wavelength refers to a peak wavelength of light emitting spectrum at which a light emission intensity becomes maximum in the light emitting spectrum, and the main peak wavelength of 550 nm is corresponding to a green light emission. In this wavelength region, an enhancement of the luminous efficiency of a fluorescent light emitting device utilizing the TTF phenomenon is desired. In a fluorescent light emitting device exhibiting blue light emission of not more than 480 nm, a higher enhancement of the luminous efficiency can be expected.

Other parts of the organic EL device of the present invention, such as the substrate, the anode, the cathode, the hole injecting layer, the hole transporting layer, and the like can be properly selected and used among those which are known, as described in WO2008/023759A1, WO2008/023759A1, WO2009/107596A1, WO2009/081857A1, US2009/0243473A1, US2008/0014464A1, US2009/0021160A1, and the like.

EXAMPLES

The present invention is hereunder described with reference to examples, but it should be construed that the present invention is not limited to the following examples.

Synthesis Example 1

(a) Synthesis of 7,12-diphenylbenzo[k]fluoranthen-3-ylboronic acid 7,12-Diphenylbenzo[k]fluoranthen-3-ylboronic acid was synthesized according to the following scheme.

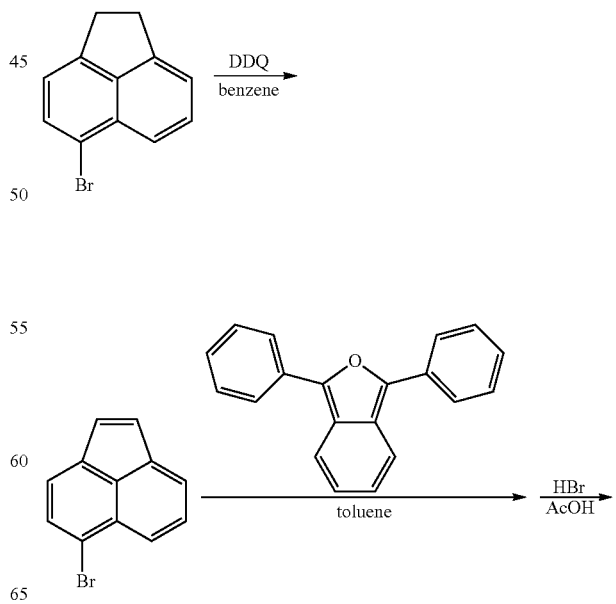

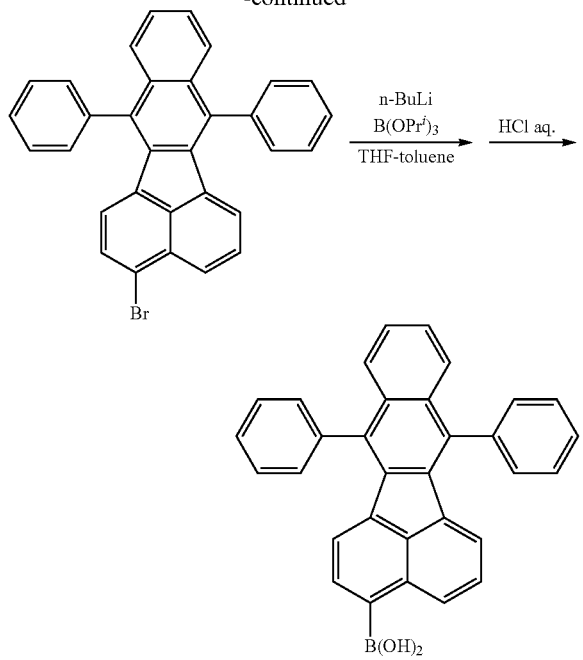

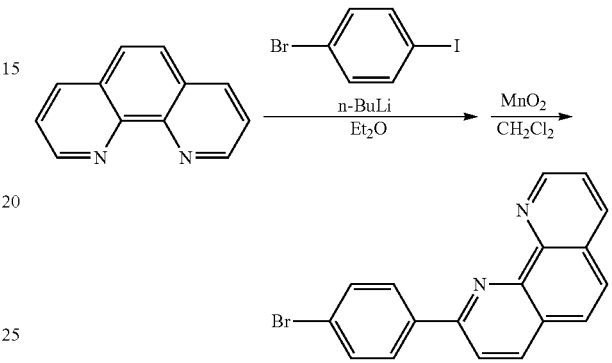

(a-1) Synthesis of 5-bromoacenaphthylene

To 25.4 g (107.3 mmol) of 5-bromoacenaphthene and 500 mL of dehydrated benzene, 29.2 g (128.7 mmol) of 2,3-dichloro-5,6-dicyano-1,4-benzoquinone (DDQ) was added, and the mixture was stirred for 6 hours under heat refluxing. Furthermore, 6.0 g (26.4 mmol) of DDQ was added to the reaction mixture, and the mixture was stirred for 4 hours by heating. After allowing the resultant mixture to stand for cooling, a precipitate was filtered off and washed with chloroform. Filtrates were combined and washed with a 10% sodium hydroxide aqueous solution and water. After liquid separation, an organic phase was dried over anhydrous sodium sulfate, and the solvent was distilled off. The residue was dried under reduced pressure to obtain 13.0 g (yield: 51.6%) of 5-bromoacenaphthylene as a brown solid.

(a-2) Synthesis of 3-bromo-7,12-diphenylbenzo[k]fluoranthene

A mixture of 14.9 g (55.2 mmol) of 1,3-diphenylisobenzofuran, 12.8 g (55.2 mmol) of 5-bromoacenaphthylene, and 50 mL of toluene was stirred for 16 hours under heat refluxing. After distilling off the solvent, 1,200 mL of acetic acid was added, and the mixture was heated at 80° C. To this mixture, 150 mL of a 48% HBr aqueous solution was added, and the mixture was stirred at 80° C. for one hour. After cooling the resultant mixture to room temperature, a precipitate was collected by filtration and washed with methanol. The resulting yellow solid was recrystallized from 200 mL of toluene. A crystal was collected by filtration to obtain 19.8 g (yield: 74%) of 3-bromo-7,12-diphenylbenzo[k]fluoranthene as a yellow solid.

(a-3) Synthesis of 7,12-diphenylbenzo[k]fluoranthen-3-ylboronic acid

A solution of 30.8 g (64.0 mmol) of 3-bromo-7,12-diphenylbenzo[k]fluoranthene in 400 mL of dehydrated tetrahydrofuran and 300 mL of dehydrated toluene was cooled to −70° C., added with 44.6 mL (70.4 mmol) of n-butyllithium dropwise, and then stirred for one hour. After adding 44.0 mL (192 mmol) of triisopropyl borate to the solution, the temperature was elevated to room temperature over 2 hours. After adding 200 mL of 10% hydrochloric acid, the mixture was stirred for 2 hours. A precipitate was collected by filtration, washed with toluene, and then dried under reduced pressure to obtain 25.14 g (yield: 88%) of 7,12-diphenylbenzo[k]fluoranthen-3-ylboronic acid as a yellow solid.

Synthesis Example 2

(b) Synthesis of 2-(4'-bromophenyl)-1,10-phenanthroline

A solution of 6.79 g (24 mmol) of 4-bromoiodobenzene in 100 mL of diethyl ether was cooled to −70° C., added with 14 mL (23.4 mmol) of n-butyllithium dropwise, and stirred for 30 min and further for 30 min after elevating the temperature to 0° C. The resulting solution was added dropwise to 100 mL of a diethyl ether solution of 3.60 g (20 mmol) of 1,10-phenanthroline at 0° C., and the mixture was stirred for 3 h. Ice water was added, an organic layer was separated, and an aqueous layer was extracted with dichloromethane (100 mL×2). The obtained organic layers were combined and dried over anhydrous sodium sulfate, followed by filtration. To a filtrate, 20 g of manganese dioxide was added, and the mixture was stirred for 30 min. Thereafter, 20 g of manganese dioxide was further added, and the mixture was stirred for one hour and allowed to stand at room temperature overnight. The reaction solution was filtered, and a filtrate was concentrated under reduced pressure and then purified by silica gel column chromatography to obtain 2.50 g (yield: 37%) of 2-(4'-bromophenyl)-1,10-phenanthroline as a yellow solid.

Synthesis Example 3

(c) Synthesis of 4-(4-bromophenyl)-2-phenyl-6-(2-pyridyl)pyrimidine 4-(4-Bromophenyl)-2-phenyl-6-(2-pyridyl)pyrimidine was synthesized according to the following scheme.

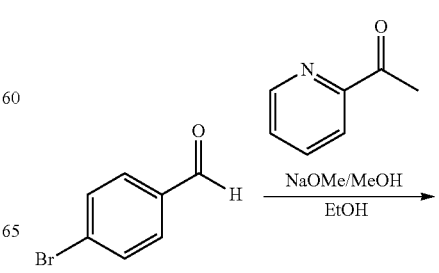

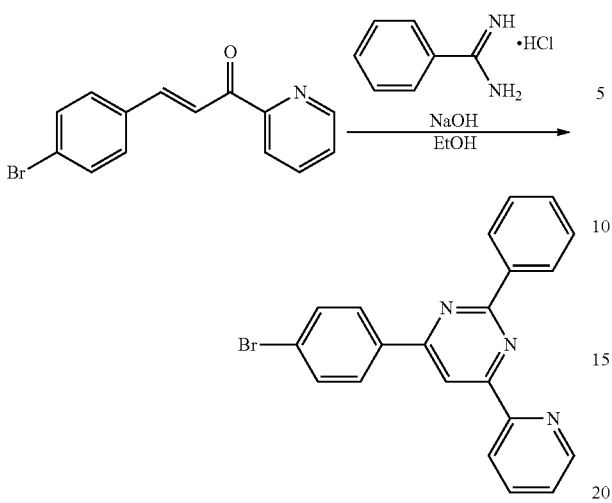

(c-1) Synthesis of (E)-3-(4-bromophenyl)-1-(2-pyridyl)-2-propen-1-one

To an ethanol (500 mL) solution of 25.3 g (137 mmol) of 4-bromobenzaldehyde, 15.6 mL (139 mmol) of 2-acetylpyridine and 25.3 g of sodium methoxide (28% methanol solution, 131 mmol) were added under argon atmosphere, and the mixture was stirred at room temperature for 8 h. A formed solid was collected by filtration and washed with methanol to obtain 13.1 g (yield: 33%) of (E)-3-(4-bromophenyl)-1(2-pyridyl)-2-propen-1-one as a white solid.

(c-2) Synthesis of 4-(4-bromophenyl)-2-phenyl-6-(2-pyridyl)pyrimidine

To 160 mL of an ethanol solution of 13.0 g (45.1 mmol) of (E)-3-(4-bromophenyl)-1-(2-pyridyl)-2-propen-1-one, 7.3 g (46.6 mmol) of benzamidine hydrochloride and 3.6 g (90 mmol) of sodium hydroxide were added under argon atmosphere, and the mixture was stirred for 16 h under heat refluxing. After cooling the reaction mixture to room temperature, a formed solid was collected by filtration and washed with water and methanol to obtain 4.31 g (yield: 25%) of 4-(4-bromophenyl)-2-phenyl-6-(2-pyridyl)pyrimidine as a pale brown solid.

Example 1

Synthesis of benzo[k]fluoranthene derivative (Compound 1)

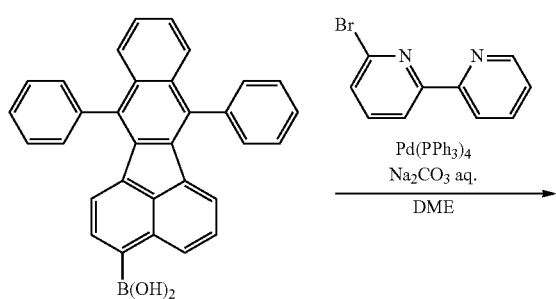

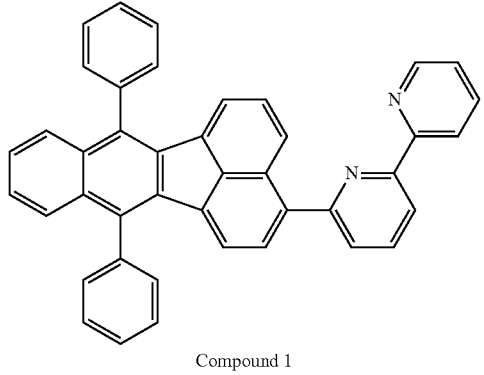

Compound 1

Under an argon atmosphere, a mixture of 1.88 g (4.2 mmol) of 7,12-diphenylbenzo[k]fluoranthen-3-ylboronic acid, 0.94 g (4.0 mmol) of 6-bromo-2,2'-bipyridine, 0.14 g (0.12 mmol) of tetrakistriphenylphosphine palladium(0), 12 mL of 1,2-dimethoxyethane, and 6 mL of a 2 M sodium hydrogencarbonate aqueous solution was stirred for 5 h under heat refluxing. The reaction mixture was cooled to room temperature and added with water, and the mixture was stirred for one hour. A formed solid was collected by filtration, washed with water and methanol, and then dried under reduced pressure. The resulting solid was purified by silica gel chromatography to obtain 1.98 g of a yellow solid. As a result of mass spectral analysis, the obtained compound was identified to Compound 1 (m/e=558 to the molecular weight of 558.21). The yield was 89%.

Example 2

Synthesis of benzo[k]fluoranthene derivative (Compound 2)

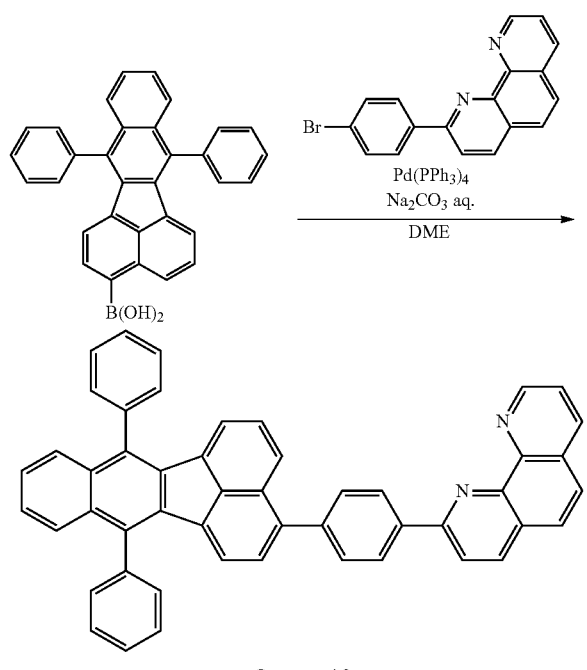

Compound 2

A compound was synthesized in the same manner as in Example 1, except for using 2-(4'-bromophenyl)-1,10- phenanthroline in place of 6-bromo-2,2'-bipyridine. As a result of mass spectral analysis, the obtained compound was identified to Compound 2 (m/e=658 to the molecular weight of 658.24). The yield was 94%.

Example 3

Synthesis of benzo[k]fluoranthene derivative (Compound 3)

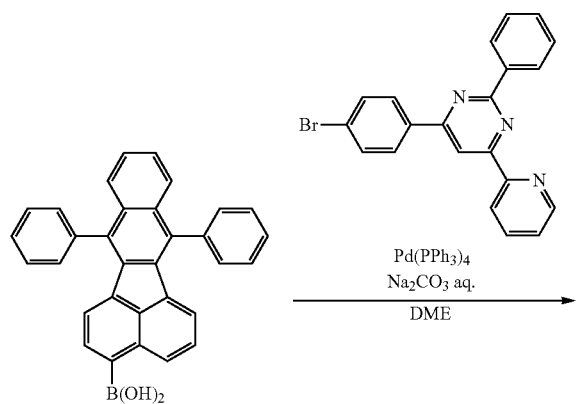

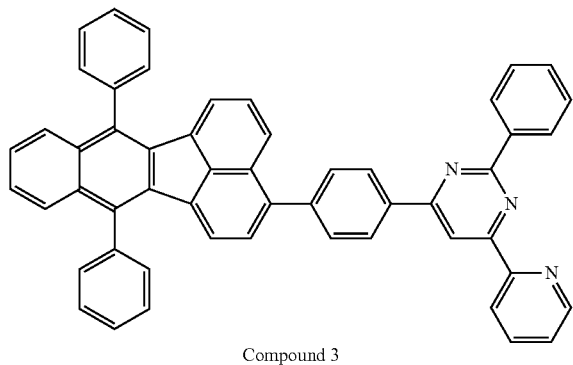

Compound 3

A compound was synthesized in the same manner as in Example 1, except for using 4-(4-bromophenyl)-2-phenyl-6-(2-pyridyl)pyrimidine in place of 6-bromo-2,2'-bipyridine. As a result of mass spectral analysis, the obtained compound was identified to be Compound 3 (m/e=711 to the molecular weight of 711.27). The yield was 74%.

Measurement of Physical Properties

The following physical properties of Compounds 1 and 2 were measured by the following methods. The measurement results are shown in Table 1.

(1) Triplet energy (ET)

The triplet energy was measured using a commercially available apparatus: F-4500 (manufactured by Hitachi, Ltd.). The expression for converting to ET is as follows.

$ET(eV) = 1239.85/\lambda \text{edge}$

In a phosphorescent spectrum in which a phosphorescence intensity is the vertical axis, and a wavelength is the horizontal axis, the "λedge" means a wavelength value at the point of intersection of a tangent line with the horizontal axis, the tangent line being drawn in a rising portion on the short wavelength side of the phosphorescent spectrum. Unit: nm.

(2) Ionization Potential

The ionization potential was measured under the surrounding atmosphere using a photoelectron spectrometer (AC-3, manufactured by Riken Keiki Co., Ltd.). Specifically, light was irradiated on the material, and on that occasion, a quantity of electron generated by charge separation was measured, thereby determining the ionization potential.

(3) Affinity

The affinity was calculated from the measured values of ionization potential and energy gap. The energy gap was measured from an absorption end of the absorption spectrum of a toluene solution of Compound 1 or 2. Specifically, an absorption spectrum was measured using a commercially available visible light/ultraviolet spectrophotometer, and the affinity was calculated from a wavelength (absorption end) at which the spectrum started to rise up.

TABLE 1

| | Triplet energy (eV) | Ionization potential (eV) | Affinity (eV) |
|---|---|---|---|
| Compound 1 | 2.1 | 6.0 | 3.2 |
| Compound 2 | 2.1 | 6.0 | 3.2 |
| Compound 3 | 2.1 | 6.0 | 3.2 |

Example 4

(1) Manufacture of Organic EL Device

A glass substrate provided with an ITO transparent electrode (anode) having a size of 25 mm×75 mm and a thickness of 1.1 mm (manufactured by Geomatic Inc.) was subjected to ultrasonic cleaning in isopropyl alcohol for 5 min and then subjected to UV ozone cleaning for 30 min.

The thus cleaned transparent electrode line-provided glass substrate was installed in a substrate holder of a vacuum vapor deposition apparatus, and Compound HT-1 was deposited so as to cover the transparent electrode line to form a film having a thickness of 50 nm. The HT-1 film functions as a hole injecting layer. Subsequently, Compound HT-2 was vapor deposited, thereby forming an HT-2 film having a thickness of 45 nm on the HT-1 film. The HT-2 film functions as a hole transporting layer.

Compound BH-1 (host material) and Compound BD-1 (dopant material) were vapor deposited in a film thickness ratio of 20:1 on the HT-2 film, thereby forming an organic layer having a thickness of 25 nm. This organic layer functions as a light emitting layer. Compound 1 was vapor deposited on the light emitting layer, thereby forming an electron transporting layer having a film thickness of 25 nm. Thereafter, LiF was deposited in a film thickness of 1 nm. Metallic Al was vapor deposited in a thickness of 80 nm on this LiF film to form a metal cathode, thereby fabricating an organic EL light emitting device.

HT-1

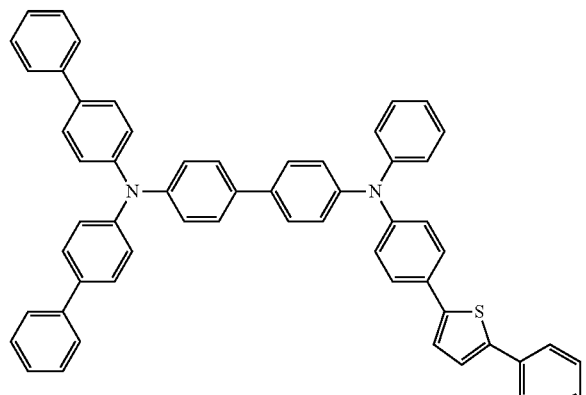

HT-2

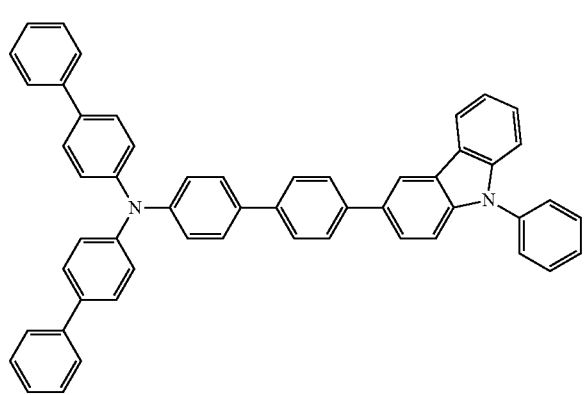

BH-1

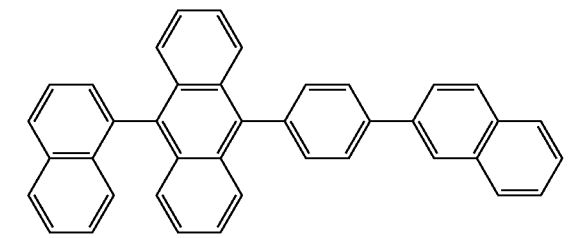

BD-1

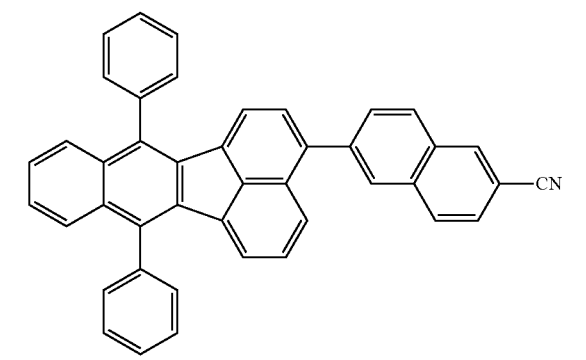

(2) Evaluation of Organic EL Device

With respect to the fabricated organic EL device, device performances (driving voltage, luminous efficiency, and luminescent color) when driving at a current density of 10 mA/cm² and a time until a luminance was reduced by 5% when driving at a current density of 8 mA/cm² (lifetime of 95% luminance) were measured. The results are shown in Table 2.

Example 5 and Comparative Examples 1 to 2

Manufacture and Evaluation of Organic EL Devices

Organic EL devices were fabricated and evaluated in the same manners as in Example 3, except for forming an electron transporting layer using Compound 2 (Example 5), ET-1 (Comparative Example 1), and ET-2 (Comparative Example 2), respectively in place of Compound 1. The results are shown in Table 2.

ET-1

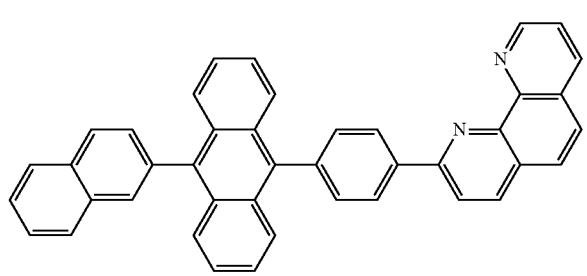

ET-2

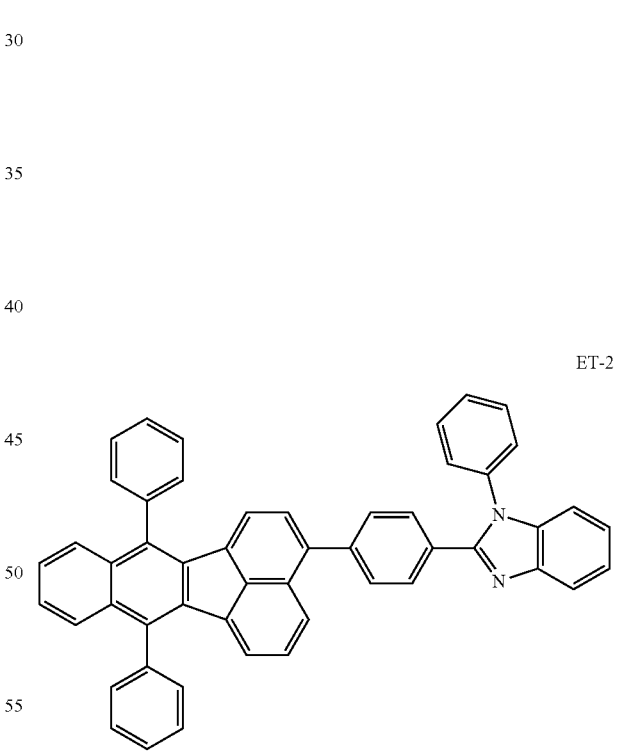

Example 6

Manufacture and Evaluation of Organic EL Device

An organic EL device was fabricated and evaluated in the same manners as in Example 5, except for forming a light emitting layer using BD-2 in place of BD-1. The results are shown in Table 2.

BD-2

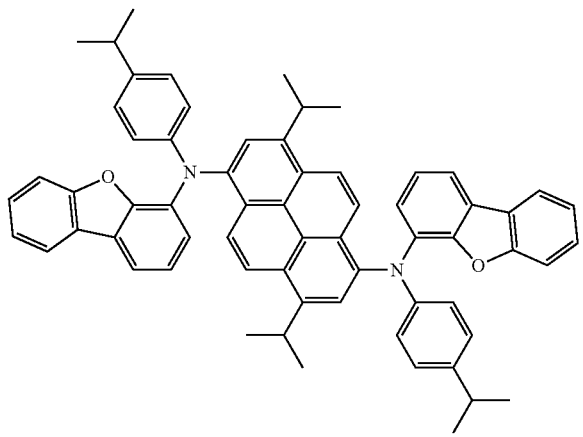

ratio of 20:1 on the HT-2 film, thereby forming a light emitting layer having a thickness of 25 nm. Compound 1 and lithium quinolinolate (Liq) were vapor deposited in a film thickness ratio of 1:1 on the light emitting layer, thereby forming an electron transporting layer in a film thickness of 25 nm on the light emitting layer. Metallic Al was vapor deposited in a thickness of 80 nm on this electron transporting layer to form a metal cathode, thereby fabricating an organic EL device.

The resulting organic EL device was evaluated in the same manners as in Example 3. The results are shown in Table 3.

Examples 8 to 9 and Comparative Examples 3 to 4

Manufacture and Evaluation of Organic EL Devices

Organic EL devices were fabricated and evaluated in the same manners as in Example 7, except for forming an electron transporting layer using Compound 2 (Example 8), Compound 3 (Example 9), ET-1 (Comparative Example 3), and ET-2 (Comparative Example 4), respectively in place of Compound 1. The results are shown in Table 3.

TABLE 2

| | Electron transporting layer | Dopant | Driving voltage (V) | Luminous efficiency (Cd/A) | Luminescent color | Lifetime of 95% luminance (h) |
|---|---|---|---|---|---|---|
| Example 4 | Compound 1 | BD-1 | 3.3 | 8.5 | Blue | 750 |
| Example 5 | Compound 2 | BD-1 | 3.3 | 8.6 | Blue | 550 |
| Example 6 | Compound 2 | BD-2 | 3.4 | 8.2 | Blue | 200 |
| Comparative Example 1 | ET-1 | BD-1 | 3.2 | 7.4 | Blue | 170 |
| Comparative Example 2 | ET-2 | BD-1 | 5.8 | 6.8 | Blue | 450 |

Example 7

A glass substrate provided with an ITO transparent electrode (anode) having a size of 25 mm×75 mm and a thickness of 1.1 mm (manufactured by Geomatic Inc.) was subjected to ultrasonic cleaning in isopropyl alcohol for 5 min and then subjected to UV ozone cleaning for 30 min.

The thus cleaned transparent electrode line-provided glass substrate was installed in a substrate holder of a vacuum vapor deposition apparatus, and Compound HT-1 was deposited so as to cover the transparent electrode line, thereby forming a film having a thickness of 50 nm. The HT-1 film functions as a hole injecting layer. Subsequently, Compound HT-2 was vapor deposited, thereby forming an HT-2 film having a thickness of 45 nm on the HT-1 film. The HT-2 film functions as a hole transporting layer.

Compound BH-1 (host material) and Compound BD-1 (dopant material) were vapor deposited in a film thickness Example 10

Manufacture and Evaluation of Organic EL Device

An organic EL device was fabricated and evaluated in the same manners as in Example 7, except for forming a light emitting layer using BD-2 in place of BD-1. The results are shown in Table 3.

TABLE 3

| | Electron transporting layer | Dopant | Driving voltage (V) | Luminous efficiency (Cd/A) | Luminescent color | Lifetime of 95% luminance (h) |
|---|---|---|---|---|---|---|
| Example 7 | Compound 1 + Liq | BD-1 | 3.5 | 8.8 | Blue | 750 |
| Example 8 | Compound 2 + Liq | BD-1 | 3.3 | 8.1 | Blue | 250 |
| Example 9 | Compound 3 + Liq | BD-1 | 3.6 | 8.2 | Blue | 200 |
| Example 10 | Compound 1 + Liq | BD-2 | 3.6 | 7.7 | Blue | 190 |
| Comparative Example 3 | ET-1 + Liq | BD-1 | 3.7 | 8.3 | Blue | 70 |
| Comparative Example 4 | ET-2 + Liq | BD-1 | 4.6 | 7.7 | Blue | 40 |

From the results of Table 2 to 3, it is noted that by using each of Compounds 1 to 3, an organic EL device having a low driving voltage and exhibiting high efficiency and long lifetime is obtained. It may be considered that a low voltage was realized by introducing a bipyridine structure (Compound 1), a phenanthroline structure (Compound 2), or a 2-phenyl-4-(2-pyridyl)pyrimidine structure (Compound 3), each enhancing the electron injecting properties, and that the deterioration of the device by the hole entering into the electron transporting layer was reduced because the benzo[k]fluoranthene ring has high hole resistance, whereby high efficiency of the device and prolonged light emission lifetime were realized at the same time.

Though it is technologically difficult to achieve efficiency, lifetime and low voltage at the same time, from the results of Examples of the present invention, the problem which had been conventionally difficulty achieved could be solved by using each of Compounds 1 to 3.

Since the affinity (Af) of the benzofluoranthene ring is large, the driving voltage is low even when the electron transporting layer is a co-vapor deposited layer with lithium quinolate.

It is suggested that the effect of a blocking material may be attributable to the high luminous efficiency achieved by each of Compounds 1 to 3. The triplet energy of the host material BH-1 is 1.8 eV when calculated in the same manner as in each of Compounds 1 to 3. Since the triplet energies of Compounds 1 to 3 is a sufficiently large as compared with that of BH-1, it can be considered that the triplet exciton is effectively confined within the light emitting layer.

Industrial Applicabilty

The organic EL device containing the benzo[k]fluoranthene derivative of the present invention can be used for display panels for large-sized television, illumination panels, and the like, which are desired to reduce the electric power consumption.

What is claimed is:

1. A benzo[k]fluoranthene derivative of formula (1):

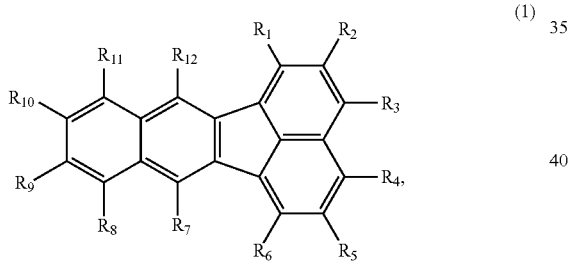

(1)

wherein:
$R_1$ to $R_{12}$ are each independently a hydrogen atom, a halogen atom, an optionally substituted alkyl group comprising 1 to 10 carbon atoms, an optionally substituted cycloalkyl group comprising 3 to 8 ring carbon atoms, a substituted silyl group comprising 3 to 30 carbon atoms, a cyano group, an optionally substituted alkoxy group comprising 1 to 20 carbon atoms, an optionally substituted aryloxy group comprising 6 to 20 ring carbon atoms, an optionally substituted aryl group comprising 6 to 30 ring carbon atoms, or an optionally substituted heterocyclic group comprising 5 to 30 ring atoms;
provided that at least one of $R_1$ to $R_{12}$ is a group of formula (1a):

(1a), wherein L is a single bond, a divalent to tetravalent residue of an optionally substituted aromatic hydrocarbon ring selected from benzene, naphthalene, biphenyl, pyrene, phenanthrene, chrysene, p-terphenyl, m-terphenyl, and 9,9-dimethylfluorene, a divalent to tetravalent residue of an optionally substituted heterocyclic ring comprising 5 to 30 ring atoms, or a divalent to tetravalent residue of a ring formed by bonding 2 to 3 rings selected from the aromatic hydrocarbon ring and the heterocyclic ring via a single bond;
n is an integer from 1 to 3; and
HAr is a nitrogen comprising heterocyclic ring selected from the group consisting of formulae (3) to (7):

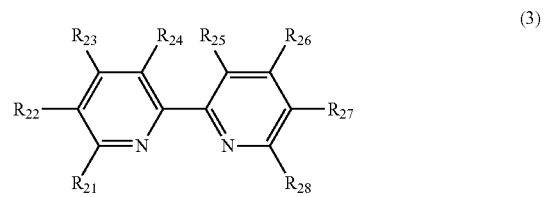

(3)

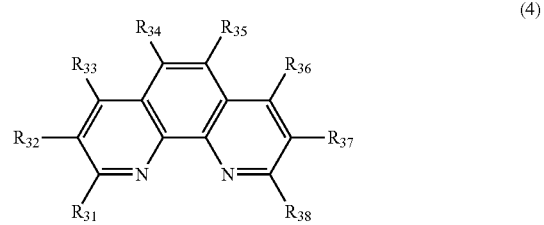

(4)

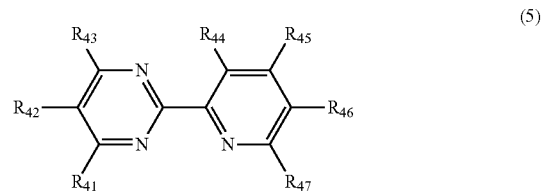

(5)

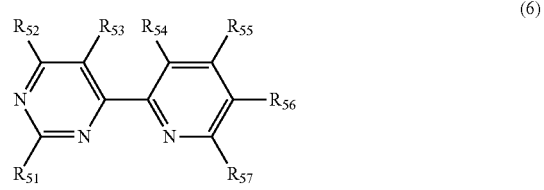

(6)

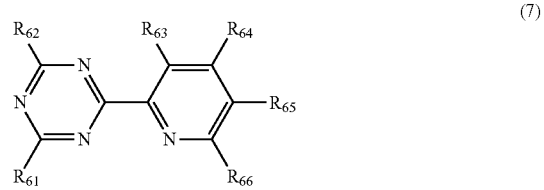

(7)

wherein:
$R_{21}$ to $R_{66}$ are each independently a hydrogen atom, a halogen atom, an optionally substituted alkyl group comprising 1 to 10 carbon atoms, an optionally substituted cycloalkyl group comprising 3 to 8 ring carbon atoms, a substituted silyl group comprising 3 to 30 carbon atoms, a cyano group, an optionally substituted alkoxy group comprising 1 to 20 carbon atoms, an optionally substituted aryloxy group comprising 6 to 20 ring carbon atoms, an optionally substituted alkylthio group comprising 1 to 20 carbon atoms, an optionally substituted mono- or dialkylamino group comprising 1 to 20 carbon atoms, an optionally substituted aryl group having comprising 6 to 30 ring carbon atoms, an optionally substituted heterocyclic group comprising 5 to 30 ring atoms, an optionally substituted arylthio group comprising 6 to 20 ring carbon atoms, or an optionally substituted mono- or diarylamino group comprising 6 to 40 ring carbon atoms;

in the formula (3), two or more of $R_{21}$ to $R_{28}$ may be bonded to each other to form a ring-forming optionally substituted, saturated or unsaturated group, provided that any one of $R_{21}$ to $R_{28}$ is a single bond and is bonded to L, and the case where $R_{24}$ and $R_{25}$ are bonded to each other to form an optionally substituted methylene group is excluded;

in the formula (4), two or more of $R_{31}$ to $R_{38}$ may be bonded to each other to form a ring-forming optionally substituted, saturated or unsaturated group, provided that $R_{31}$ to $R_{38}$ is a single bond and is bonded to L;

in the formula (5), two or more of $R_{41}$ to $R_{47}$ may be bonded to each other to form a ring-forming optionally substituted, saturated or unsaturated group, provided that any one of $R_{41}$ to $R_{47}$ is a single bond and is bonded to L;

in the formula (6), two or more of $R_{51}$ to $R_{57}$ may be bonded to each other to form a ring-forming optionally substituted, saturated or unsaturated group, provided that any one of $R_{51}$ to $R_{57}$ is a single bond and is bonded to L, and the case where $R_{53}$ and $R_{54}$ are bonded to each other to form an optionally substituted methylene group is excluded; and in the formula (7), two or more of $R_{61}$ to $R_{66}$ may be bonded to each other to form a ring-forming optionally substituted, saturated or unsaturated group, provided that any one of $R_{61}$ to $R_{66}$ is a single bond and is bonded to L, and wherein when a groups substituted the substituted (s) is/are independently selected from a halogen atom, a substituted or unsubstituted alkyl group having 1 to 10 carbon atoms, substituted or unsubstituted, substituted cycloalkyl group having 3 to 8 ring carbon atoms, a substituted or unsubstituted, substituted silyl group having 3 to 30 carbon atoms, a cyano group, substituted or unsubstituted alkoxy group having 1 to 20 carbon atoms, a substituted or unsubstituted aryloxy group having 6 to 20 ring carbon atoms, a substituted or unsubstituted alkylthio group having 1 to 20 carbon atoms, substituted or unsubstituted mono- or dialkylamino group having 1 to 20 carbon atoms, a substituted or unsubstituted aryl group having 6 to 30 ring carbon atoms, and a substituted or unsubstituted heterocyclic group having 5 to 30 ring atoms.

2. The benzo[k]fluoranthene derivative of claim 1, having a formula (8):

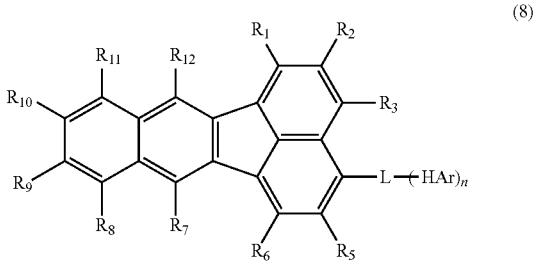

(8)

wherein $R_1$ to $R_3$, $R_5$ to $R_{12}$, HAr, L, and n are as defined in formula (1).

3. The benzo[k]fluoranthene derivative of claim 1, wherein n is 1.

4. A material, comprising a benzo[k]fluoranthene derivative of claim 1.

5. The material of claim 4, being an electron injecting material or an electron transporting material.

6. An organic electroluminescence device, comprising:
an organic thin film layer comprising a light emitting layer;
a cathode; and
an anode,
wherein the organic thin film layer is interposed between the cathode and the anode, and
wherein the organic thin film layer comprises a benzo[k]fluoranthene derivative of claim 1.

7. The device of claim 6, wherein the organic thin film layer comprises an electron injecting layer or an electron transporting layer, and the electron injecting layer or electron transporting layer comprises the benzo[k]fluoranthene derivative.

8. The device of claim 7, wherein the electron injecting layer or electron transporting layer comprising the benzo[k]fluoranthene derivative further comprises a reducing dopant.

9. The device of claim 8, wherein the reducing dopant is at least one selected from the group consisting of an alkali metal, an alkaline earth metal, a rare earth metal, an alkaline metal oxide, an alkali metal halide, an alkaline earth metal oxide, an alkaline earth metal halide, a rare earth metal oxide, a rare earth metal halide, an organic complex of an alkali metal, an organic complex of an alkaline earth metal, and an organic complex of a rare earth metal.

10. The material of claim 5, being an electron injection material.

11. The material of claim 5, being an electron transporting material.

12. The device of claim 7, wherein the organic thin film layer comprises an electron injection layer comprising the benzo[k]fluoranthene derivative.

13. The device of claim 7, wherein the organic thin film layer comprises an electron transporting layer comprising the benzo[k]fluoranthene derivative.

14. The device of claim 12, wherein the electron injecting layer further comprises at least one reducing dopant selected from the group consisting of an alkali metal, an alkaline earth metal, a rare earth metal, an alkaline metal oxide, an alkali metal halide, an alkaline earth metal oxide, an alkaline earth metal halide, a rare earth metal oxide, a rare earth metal halide, an organic complex of an alkali metal, an organic complex of an alkaline earth metal, and an organic complex of a rare earth metal.

15. The device of claim 13, wherein the electron transporting layer further comprises at least one reducing dopant selected from the group consisting of an alkali metal, an alkaline earth metal, a rare earth metal, an alkaline metal oxide, an alkali metal halide, an alkaline earth metal oxide, an alkaline earth metal halide, a rare earth metal oxide, a rare earth metal halide, an organic complex of an alkali metal, an organic complex of an alkaline earth metal, and an organic complex of a rare earth metal.

16. The benzo[k]fluoranthene derivative of claim 1, wherein one of $R_{21}$, $R_{22}$, $R_{27}$, and $R_{28}$ of formula (3) is a single bond and is bonded to L.

17. The benzo[k]fluoranthene derivative of claim 1, wherein one of $R_{41}$, $R_{43}$ and $R_{47}$ of formula (5) is a single bond and is bonded to L.

18. The benzo[k]fluoranthene derivative of claim 1, wherein one of $R_{51}$, $R_{52}$ and $R_{57}$ of formula (6) is a single bond and is bonded to L.

19. The benzo[k]fluoranthene derivative of claim 1, wherein one of $R_{61}$, $R_{62}$ and $R_{66}$ of formula (7) is a single bond and is bonded to L.

* * * * *